US008979872B2

(12) United States Patent
Harris et al.

(10) Patent No.: US 8,979,872 B2
(45) Date of Patent: Mar. 17, 2015

(54) DEVICES FOR ENGAGING, APPROXIMATING AND FASTENING TISSUE

(75) Inventors: Peter S. Harris, Bellevue, WA (US); Barry Hal Rabin, Idaho Falls, ID (US)

(73) Assignee: Longevity Surgical, Inc., Idaho Falls, ID (US)

( * ) Notice: Subject to any disclaimer, the term of this patent is extended or adjusted under 35 U.S.C. 154(b) by 1011 days.

(21) Appl. No.: 12/184,173

(22) Filed: Jul. 31, 2008

(65) Prior Publication Data

US 2008/0319455 A1 Dec. 25, 2008

Related U.S. Application Data

(63) Continuation-in-part of application No. 12/048,206, filed on Mar. 13, 2008, now Pat. No. 8,142,450.

(60) Provisional application No. 60/894,626, filed on Mar. 13, 2007, provisional application No. 60/952,871, filed on Jul. 31, 2007, provisional application No. 60/990,968, filed on Nov. 29, 2007.

(51) Int. Cl.
*A61B 17/10* (2006.01)
*A61B 17/08* (2006.01)
(Continued)

(52) U.S. Cl.
CPC ........... *A61B 17/0684* (2013.01); *A61B 17/083* (2013.01); *A61B 17/10* (2013.01); *A61B 17/0644* (2013.01); *A61B 2017/00818* (2013.01); *A61B 2017/081* (2013.01)
USPC .......................... 606/139; 606/153; 227/175.1

(58) Field of Classification Search
CPC ............... A61B 17/0684; A61B 17/10; A61B 17/0057; A61B 17/0644; A61B 17/083; A61B 2017/00818; A61B 2017/081; A61B 17/0643; A61B 2017/00349; A61B 2017/00637; A61B 2017/00668; A61F 5/0086
USPC ................. 606/139, 158, 219, 142, 151, 153; 600/217; 227/175.1
See application file for complete search history.

(56) References Cited

U.S. PATENT DOCUMENTS 2,808,055 A 10/1957 Thayer
4,165,747 A 8/1979 Bermant
(Continued)

FOREIGN PATENT DOCUMENTS

WO WO 2007/089843 * 1/2007

OTHER PUBLICATIONS

Fusco, Pedro E.B. MD, et al., "Comparison of Anterior Gastric Wall and Greater Gastric Curvature Invaginations for Weight Loss in Rats," Obesity Surgery, vol. 17, No. 10, pp. 1340-1345 (Feb. 2007).
(Continued)

*Primary Examiner* — Julian W Woo
(74) *Attorney, Agent, or Firm* — Ann W. Speckman; Speckman Law Group PLLC

(57) ABSTRACT

New interventional methods and devices for reducing gastric volume, and thereby treating obesity, are disclosed. The procedures are generally performed laparoscopically and may generally be described as laparoscopic plication gastroplasty (LPG) in which, after obtaining abdominal access, spaced apart sites on a gastric wall are engaged and approximated to create one or more tissue folds that are then secured by placing one or more tissue fasteners to produce one or more plications projecting into the gastrointestinal space. These procedures are preferably carried out entirely extragastrically (i.e. without penetrating through the gastrointestinal wall), thereby minimizing the risks of serious complications. Minimally invasive devices for engaging, approximating and fastening soft tissues are disclosed that enable these new interventional methods to be carried out safely, efficiently and quickly.

38 Claims, 55 Drawing Sheets

(51) Int. Cl.
*A61B 17/04* (2006.01)
*A61B 17/068* (2006.01)
*A61B 17/064* (2006.01)
*A61B 17/00* (2006.01)

(56) References Cited

U.S. PATENT DOCUMENTS

| | | | |
|---|---|---|---|
| 4,603,693 A * | 8/1986 | Conta et al. | 227/179.1 |
| 4,724,840 A | 2/1988 | McVay et al. | |
| 5,292,326 A | 3/1994 | Green et al. | |
| 5,332,142 A | 7/1994 | Robinson | |
| 5,345,949 A | 9/1994 | Shlain | |
| 5,355,897 A | 10/1994 | Pietrafitta et al. | |
| 5,389,102 A | 2/1995 | Green et al. | |
| 5,470,010 A | 11/1995 | Rothfuss et al. | |
| 5,480,406 A | 1/1996 | Nolan et al. | |
| 5,485,952 A | 1/1996 | Fontayne | |
| 5,565,004 A | 10/1996 | Christoudias | |
| 5,643,295 A | 7/1997 | Yoon | |
| 5,662,258 A | 9/1997 | Knodel et al. | |
| 5,662,700 A * | 9/1997 | Lazarus | 606/194 |
| 5,700,275 A | 12/1997 | Bell et al. | |
| 5,709,224 A * | 1/1998 | Behl et al. | 128/898 |
| 5,725,554 A * | 3/1998 | Simon et al. | 606/219 |
| 5,865,791 A * | 2/1999 | Whayne et al. | 604/500 |
| 5,972,021 A | 10/1999 | Huttner et al. | |
| 6,042,599 A | 3/2000 | Huttner et al. | |
| 6,086,600 A | 7/2000 | Kortenbach | |
| 6,102,922 A | 8/2000 | Jakobsson et al. | |
| 6,179,195 B1 * | 1/2001 | Adams et al. | 227/180.1 |
| 6,273,903 B1 | 8/2001 | Wilk | |
| 6,436,088 B2 * | 8/2002 | Frazier et al. | 604/508 |
| 6,478,791 B1 | 11/2002 | Carter et al. | |
| 6,544,253 B1 * | 4/2003 | Tanner | 623/1.23 |
| 6,558,400 B2 | 5/2003 | Deem et al. | |
| 6,602,286 B1 * | 8/2003 | Strecker | 623/1.24 |
| 6,679,895 B1 | 1/2004 | Sancoff et al. | |
| 6,913,607 B2 | 7/2005 | Ainsworth et al. | |
| 6,986,451 B1 | 1/2006 | Mastri et al. | |
| 7,001,399 B2 | 2/2006 | Damarati | |
| 7,097,650 B2 | 8/2006 | Weller et al. | |
| 7,211,094 B2 | 5/2007 | Gannoe et al. | |
| 7,288,101 B2 | 10/2007 | Deem et al. | |
| 7,458,978 B1 | 12/2008 | Bender et al. | |
| 7,473,258 B2 | 1/2009 | Clauson et al. | |
| 7,556,647 B2 | 7/2009 | Drews et al. | |
| 7,618,426 B2 * | 11/2009 | Ewers et al. | 606/139 |
| 7,736,372 B2 | 6/2010 | Reydel et al. | |
| 7,862,574 B2 * | 1/2011 | Deem et al. | 606/153 |
| 8,057,490 B2 | 11/2011 | Harris et al. | |
| 8,100,921 B2 | 1/2012 | Harris et al. | |
| 8,142,450 B2 | 3/2012 | Harris et al. | |
| 8,414,600 B2 | 4/2013 | Harris et al. | |
| 8,469,972 B2 | 6/2013 | Harris et al. | |
| 8,500,777 B2 | 8/2013 | Harris et al. | |
| 2002/0082621 A1 * | 6/2002 | Schurr et al. | 606/151 |
| 2002/0091395 A1 | 7/2002 | Gabbay | |
| 2002/0165561 A1 | 11/2002 | Ainsworth et al. | |
| 2002/0173803 A1 | 11/2002 | Ainsworth et al. | |
| 2003/0088270 A1 | 5/2003 | Lubbers et al. | |
| 2004/0030351 A1 * | 2/2004 | Goldberg | 606/192 |
| 2004/0093023 A1 * | 5/2004 | Allen et al. | 606/213 |
| 2004/0116949 A1 * | 6/2004 | Ewers et al. | 606/167 |
| 2004/0215216 A1 | 10/2004 | Gannoe et al. | |
| 2004/0225183 A1 | 11/2004 | Michlitsch et al. | |
| 2004/0225305 A1 | 11/2004 | Ewers et al. | |
| 2004/0267312 A1 * | 12/2004 | Kanner et al. | 606/219 |
| 2005/0038449 A1 | 2/2005 | Sancoff et al. | |
| 2005/0065397 A1 * | 3/2005 | Saadat et al. | 600/104 |
| 2005/0080438 A1 | 4/2005 | Weller et al. | |
| 2005/0096673 A1 | 5/2005 | Stack et al. | |
| 2005/0159769 A1 | 7/2005 | Alverdy | |
| 2005/0177176 A1 | 8/2005 | Gerbi et al. | |
| 2005/0192601 A1 | 9/2005 | Demarais | |
| 2005/0203568 A1 * | 9/2005 | Burg et al. | 606/200 |
| 2005/0216042 A1 | 9/2005 | Gertner | |
| 2005/0228415 A1 | 10/2005 | Gertner | |
| 2005/0234294 A1 | 10/2005 | Saadat et al. | |
| 2005/0234512 A1 | 10/2005 | Nakao | |
| 2005/0247320 A1 | 11/2005 | Stack et al. | |
| 2005/0250980 A1 | 11/2005 | Swanstrom et al. | |
| 2005/0251160 A1 | 11/2005 | Saadat et al. | |
| 2005/0251161 A1 | 11/2005 | Saadat et al. | |
| 2005/0251162 A1 | 11/2005 | Rothe et al. | |
| 2005/0251177 A1 * | 11/2005 | Saadat et al. | 606/153 |
| 2005/0256533 A1 | 11/2005 | Roth et al. | |
| 2005/0267529 A1 | 12/2005 | Crockett et al. | |
| 2005/0283190 A1 * | 12/2005 | Huitema et al. | 606/219 |
| 2006/0020275 A1 | 1/2006 | Goldfarb et al. | |
| 2006/0020276 A1 | 1/2006 | Saadat et al. | |
| 2006/0036267 A1 | 2/2006 | Saadat et al. | |
| 2006/0106288 A1 | 5/2006 | Roth et al. | |
| 2006/0106405 A1 | 5/2006 | Fann et al. | |
| 2006/0157067 A1 | 7/2006 | Saadat et al. | |
| 2006/0271076 A1 | 11/2006 | Weller et al. | |
| 2006/0276810 A1 | 12/2006 | Kelleher et al. | |
| 2006/0293701 A1 | 12/2006 | Ainsworth et al. | |
| 2007/0021760 A1 | 1/2007 | Kelleher | |
| 2007/0043384 A1 | 2/2007 | Ortiz et al. | |
| 2007/0060932 A1 | 3/2007 | Stack et al. | |
| 2007/0112338 A1 | 5/2007 | Cohen et al. | |
| 2007/0112364 A1 | 5/2007 | Gerbi et al. | |
| 2007/0173888 A1 | 7/2007 | Gertner et al. | |
| 2007/0179335 A1 | 8/2007 | Gertner et al. | |
| 2007/0276413 A1 | 11/2007 | Nobles | |
| 2007/0276432 A1 | 11/2007 | Stack et al. | |
| 2008/0033241 A1 * | 2/2008 | Peh et al. | 600/109 |
| 2008/0234705 A1 | 9/2008 | Cropper et al. | |
| 2008/0249539 A1 | 10/2008 | Stokes et al. | |
| 2008/0249541 A1 | 10/2008 | Stokes et al. | |
| 2008/0249542 A1 | 10/2008 | Stokes et al. | |
| 2008/0249561 A1 | 10/2008 | Stokes | |
| 2009/0024144 A1 | 1/2009 | Zeiner et al. | |
| 2009/0024148 A1 | 1/2009 | Zeiner et al. | |
| 2009/0024163 A1 | 1/2009 | Zeiner et al. | |
| 2009/0112232 A1 | 4/2009 | Crainich et al. | |
| 2009/0112234 A1 | 4/2009 | Crainich et al. | |
| 2009/0118762 A1 | 5/2009 | Crainich et al. | |
| 2009/0275961 A1 | 11/2009 | Harris et al. | |
| 2009/0275962 A1 | 11/2009 | Zeiner et al. | |
| 2009/0275980 A1 | 11/2009 | Zeiner et al. | |
| 2009/0276055 A1 | 11/2009 | Harris et al. | |
| 2009/0306681 A1 * | 12/2009 | Del Nido et al. | 606/139 |
| 2010/0023022 A1 | 1/2010 | Zeiner et al. | |
| 2010/0023024 A1 | 1/2010 | Zeiner et al. | |
| 2010/0023025 A1 | 1/2010 | Zeiner et al. | |
| 2010/0023026 A1 | 1/2010 | Zeiner et al. | |
| 2010/0174299 A1 | 7/2010 | Viola et al. | |
| 2010/0187283 A1 | 7/2010 | Crainich et al. | |
| 2010/0187285 A1 | 7/2010 | Harris et al. | |
| 2010/0191255 A1 | 7/2010 | Crainich et al. | |
| 2010/0191258 A1 | 7/2010 | Harris et al. | |
| 2010/0191262 A1 | 7/2010 | Harris et al. | |
| 2010/0191282 A1 | 7/2010 | Harris et al. | |
| 2013/0317543 A1 | 11/2013 | Rabin et al. | |
| 2013/0338680 A1 | 12/2013 | Harris et al. | |

OTHER PUBLICATIONS

Fusco, Pedro E.B. MD, et al., "Evaluation of Gastric Greater Curvature Invaginations for Weight Loss in Rats," Obesity Surgery, vol. 16, No. 2, pp. 172-177 (Feb. 2006).

Puccini, Carlos Elias Sales MD, "Surset Gastric Sales: An Alternative for Restrictive Bariatric Surgery," Revista Colombiana de Cirugia, vol. 23, No. 3 (Jul.-Sep. 2008).

Skrekas, George MD, "Laparoscopic Gastric Fold. Without Sleeve Gastrectomy for Obesity," http://www.skrekas.net/surg_faq.htm (Jul. 2008).

Ethicon Endo-Surgery, "Assessment of Gastric Volume reduction in Surgical Weight Loss Candidate," ClinicalTrials.gov, NCT00721227 (Jul. 9, 2008).

(56) References Cited

OTHER PUBLICATIONS

Talebpour, Mohammad M.D. et al., "Laparoscopic Total Gastric Vertical Plication in Morbid Obesity," Journal of Laparoendoscopic & Advanced Surgical Techniques, vol. 17, No. 6, pp. 793-798 (2007).

Harris, Peter S.; "Non-Final Office Action,", US Patent and Trademark Office, U.S. Appl. No. 12/949,725, filed Nov. 18, 2010, 18 pgs. (Mar. 23, 2011).

Harris, Peter S.; "Non-Final Office Action," US Patent and Trademark Office, U.S. Appl. No. 12/876,051, filed Sep. 3, 2010, 17 pgs. (Feb. 10, 2011).

Harris, Peter S.; "Non-Final Office Action,"US Patent and Trademark Office, U.S. Appl. No. 13/923,281, filed Jun. 20, 2013, 33 pgs. (Nov. 8, 2013).

Harris, Peter S.; "Final Office Action,"US Patent and Trademark Office, U.S. Appl. No. 13/923,281, filed Jun. 20, 2013, 18 pgs. (Apr. 2, 2014).

\* cited by examiner

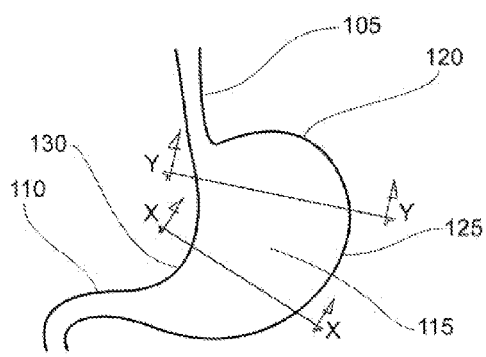
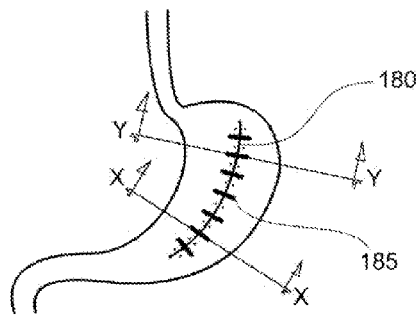
FIG. 1A
FIG. 1B
FIG. 1A1  FIG. 1A2
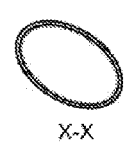
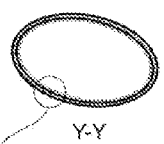
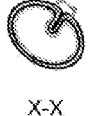
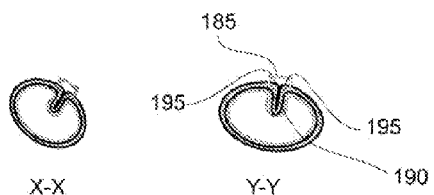
FIG. 1B1  FIG. 1B2
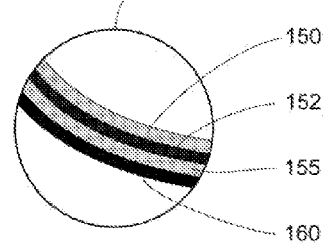
FIG. 1A3

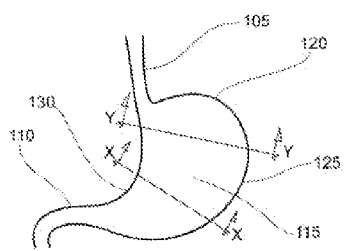
FIG. 2A
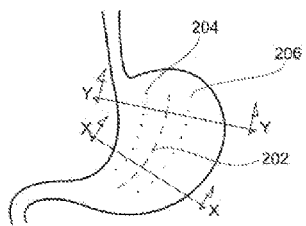
FIG. 2B
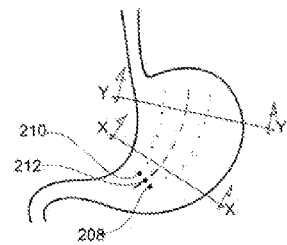
FIG. 2C
 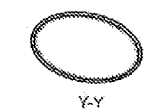
FIG. 2A1  FIG. 2A2
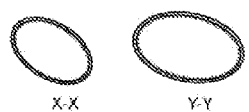
FIG. 2B1  FIG. 2B2
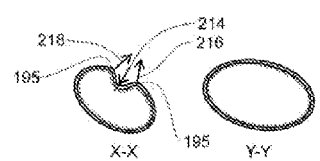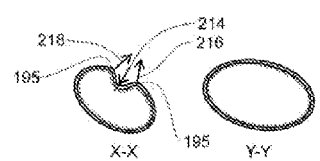
FIG. 2C1  FIG. 2C2
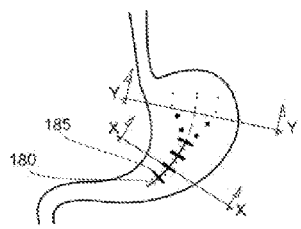
FIG. 2D
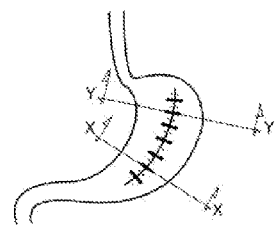
FIG. 2E
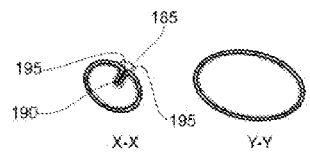
FIG. 2D1  FIG. 2D2
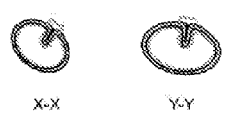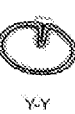
FIG. 2E1  FIG. 2E2

X-X (2x)

X-X (2x)

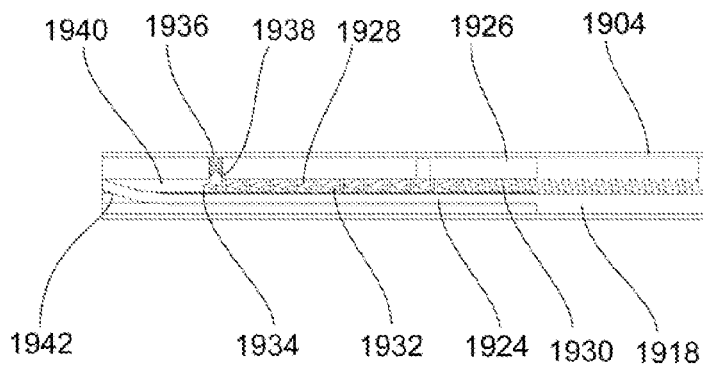
FIG. 21A
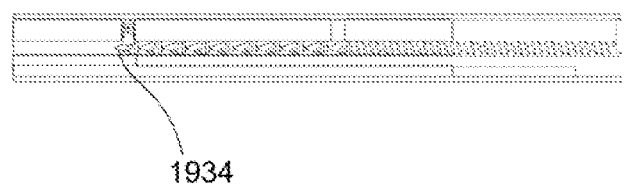
FIG. 21B
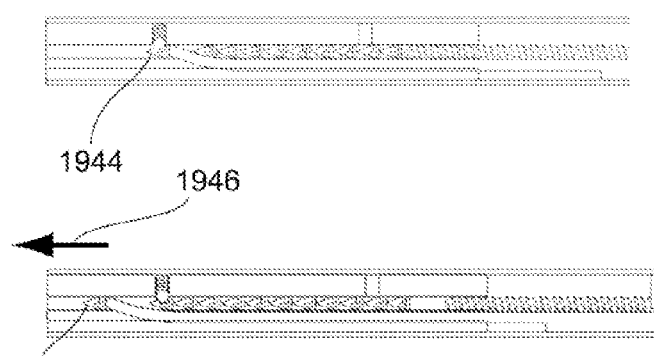
FIG. 21C
FIG. 21D
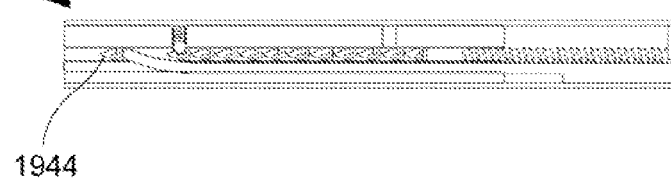
FIG. 21E
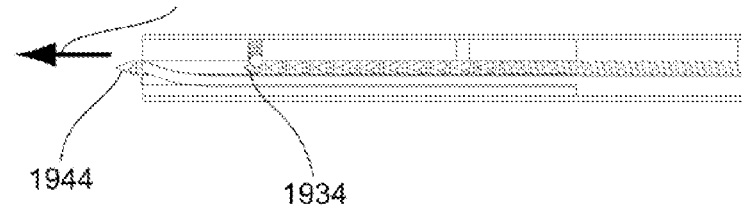

DEVICES FOR ENGAGING, APPROXIMATING AND FASTENING TISSUE

REFERENCE TO PRIORITY APPLICATIONS

This application claims priority to U.S. International Patent Application No. PCT/US08/56921 filed Mar. 13, 2008 and is a continuation-in-part of U.S. patent application Ser. No. 12/048,206, filed Mar. 13, 2008, now U.S. Pat. No. 8,142, 450, which claims priority to U.S. Provisional Patent Application No. 60/894,626 filed Mar. 13, 2007; and, this application claims priority under 35 U.S.C. §119(e) to U.S. Provisional Patent Application No. 60/952,871 filed Jul. 31, 2007 and to U.S. Provisional Patent Application No. 60/990, 968 filed Nov. 29, 2007. These patent applications are incorporated herein by reference in their entireties.

FIELD OF THE INVENTION

The present invention relates generally to methods and devices for reducing the volume of a hollow body organ, such as gastric volume. One application of methods and devices of the present invention is treating obesity in a patient by effectively reducing the functional volume of the stomach.

BACKGROUND AND DESCRIPTION OF THE PRIOR ART

Obesity is rapidly reaching epidemic proportions in developed societies worldwide. There are currently over 1 billion overweight people globally, with 300 million of these people considered clinically obese. In the United States alone there are more than 50 million obese adults, and the numbers are expected to increase by more than 50% in the next decade. Morbid obesity (i.e. obesity in which there are secondary complications such as hypertension, diabetes, coronary artery disease, stroke, congestive heart failure, orthopedic problems and pulmonary insufficiency) not only affects quality of life, but also shortens life expectancy and costs the health care industry billions of dollars annually.

Interventional procedures and associated medical devices for treating morbid obesity in patients are well known in the art. In general, these interventional procedures promote weight loss by either (a) gastric restriction or volume reduction, (b) malabsorption, or (c) a combination of the foregoing. Gastric restriction or volume reduction methods promote weight loss by limiting the amount of food intake (i.e. the patient eats less), either due to physical space limitation or by inducing a feeling of early satiety in the patient. Malabsorption methods promote weight loss by limiting the uptake of nutrients (i.e. the patient digests less of what is eaten), usually by removing or bypassing a portion of the gastrointestinal (GI) tract.

Among the earliest interventional procedures directed at promoting weight loss were variations of the jejuno-ileal bypass developed in the 1950s. This surgery effectively bypasses the small intestine and is therefore a strictly malabsorption procedure, which poses serious risks. The bilopancreatic diversion procedure, which combines bypass of most of the small intestine with a partial gastrectomy, is a combined volume reduction and malabsorption procedure that was developed in effort to reduce these risks, but it too had complications and its success was limited.

Roux-en-Y gastric bypass surgery is a commonly performed bariatric procedure, especially in the US. It was originally performed as an open interventional procedure, but it is now routinely performed laparoscopically. This procedure utilizes interventional stapling and cutting devices to form a small stomach pouch, bypassing the lower part of the stomach, and creates a Roux-en-Y limb to attach the jejunum to the pouch. The Roux-en-Y procedure is predominantly a volume reduction method (the stomach pouch is typically ~25 cc in volume), although there is a significant malabsorption component.

Despite the proven efficacy of the Roux-en-Y procedure in terms of achieving weight loss, and the recent laparoscopic improvements that have reduced the associated interventional risks, it remains a highly invasive procedure with substantial rates of morbidity. The rate of interventional mortality may be as high as 1%, and known complications include frequent pulmonary morbidity and anastomotic leaks that can be life threatening. Furthermore, the malabsorption component of the Roux-en-Y procedure can negatively affect health because of reduced vitamin uptake, and the long-term consequences of malabsorption are not yet fully understood.

A variety of other interventional procedures have also been developed involving the use of interventional stapling to bring together and fasten opposing walls of the stomach in order to reduce its volume. Most involve malabsorption to a greater or lesser extent, depending on the procedure. Examples of such procedures include the horizontal gastroplasty (HG) and vertical banded gastroplasty (VBG), as well as more recent variations such as the Magenstrasse and Mill (M&M) and laparoscopic sleeve gastrectomy (LSG) procedures that involve not only stapling, but cutting away and removal of the unused stomach portion, leaving behind a reduced volume tube or sleeve running more or less parallel to the lesser curvature between the esophagus and the pylorus. Surgically inserted artificial sleeves that longitudinally traverse the stomach may achieve similar effective volume reductions while significantly increasing malabsorption. In any case, weight loss results achieved with these procedures may sometimes approach those of the Roux-en-Y, however these procedures are not easily performed, are difficult if not impossible to reverse, and still suffer from risks of serious complications, most frequently related to failure or leakage of the staples, which can lead to dangerous infections and even death.

An alternative minimally invasive procedure recently growing in popularity involves the laparoscopic placement of an adjustable silicone ring around the upper portion of the stomach, thereby creating a small (e.g. 50-120 cc) pouch. The LAP-BAND® is one such commercially available restrictive device that, after placement, induces a feeling of early satiety in the patient. Although considerably less invasive than the Roux-en-Y procedure, and potentially reversible, significantly less weight loss has been observed with laparoscopic banding. This procedure also suffers from a variety of limitations and shortcomings. For example, because the laparoscopic band does not actually reduce the volume of the stomach, some patients report a feeling of nearly constant hunger. Additionally, long-term complications of the laparoscopic banding procedure may include tissue erosion, slippage of the band, infection, or lack of effectiveness, frequently requiring removal of the band after a period of time.

Another less invasive alternative to the above-mentioned procedures is the intragastric balloon. The intragastric balloon is an inflatable device that is deployed within the stomach, thereby displacing a known internal volume. The advantages of this method are that it is minimally invasive, involves no malabsorption component, and requires no stapling, permanent reconfiguration or removal of tissue. While the correlation between apparent stomach volume reduction and weight loss is well established by the intragastric balloon method, the weight loss achieved is typically considerably less than with Roux-en-Y. Furthermore, unless it is surgically fastened to the stomach wall, the balloon is free floating and frequent complications such as obstruction, mucosal erosion, nausea, vomiting and pain have been documented, with the result that intragastric balloons are usually removed within 6 months after initial placement.

In effort to develop even less invasive devices and procedures, more recently there has been considerable interest in various transoral (or transesophageal) endoscopic approaches for reducing stomach volume entirely from within the gastrointestinal lumen, without the need for abdominal incisions. In general, these approaches involve advancing an endoscope down the patient's esophagus and into the stomach, whereby various tools are then used to manipulate and reconfigure the stomach tissue in order to create one or more divisions or internal folds (also known as plications) within the stomach wall. To securely hold the divisions or plications so formed, some form of sutures, staples, anchors, or other similar securing means are placed transesophageally through the stomach walls, and sophisticated endoscopic tools have been developed for such purposes. Tissue approximation and fixation devices for use in endoscopic procedures are described, for example, in U.S. Patent Publications 2004/0215216, 2007/0112364, 2005/0080438. Many other types of endoscopic tissue approximation and fixation devices and fasteners are also known in the art.

While quite promising, endoscopic approaches for reducing stomach have various limitations and shortcomings. For example, they must be performed by highly skilled endoscopic surgeons and involve the use of large, complicated endoscopic devices that require specialized training to deal with the restricted access and small working space. In order to access the stomach internally, devices must be passed down the patient's esophagus, accruing a substantial risk of perforating the esophagus and injuring adjacent organs. In addition, capturing and manipulating the tissue layers and accurately applying the securing means during a transesophageal procedure is not only difficult but also hazardous, due to the significant risk of accidental injury to other organs, bleeding, etc., when piercing (intentionally or accidentally) the stomach wall. Because there is no extragastric visualization in these procedures, there is no advance warning of a developing life threatening situation that may require a rescue operation.

The stomach wall is comprised of four main tissue layers. The mucosal layer is the innermost tissue layer, adjacent a submucosal connective tissue layer. The submucosal connective tissue layer interfaces with the muscularis layer, and the serosal layer covers the exterior (extragastric) surface. Prior art gastric reduction procedures involving tissue reconfiguration from inside the stomach require the placement of sutures, staples, or anchors during surgery to hold the reconfigured tissue in place strongly enough to sustain the tensile loads imposed by normal movement of the stomach wall during ingestion and processing of food. Because the mucosal and submucosal connective tissue layers are relatively weak and prone to elastic stretching during digestion, the securing means generally penetrate the stomach wall to engage at least the muscularis layer. For this reason, the prior art securing means are generally transgastric, passing one or more times completely through the stomach wall.

Proper use and placement of fasteners that penetrate the gastric wall is challenging and concentrates significant forces over a small surface area of mucosal tissue, thereby potentially causing the suture, staple or anchor to leak or tear through the tissue, with potentially disastrous consequences. It is well known that the fasteners used in these procedures frequently migrate, dislodge or even completely disappear over time, resulting in partial or complete failure to maintain the gastrointestinal volume reduction, as well as possible complications. These are significant limitations and shortcomings of prior art bariatric procedures involving tissue reconfiguration.

Previously known interventional procedures for treating obesity through gastrointestinal volume reduction or malabsorption thus involve numerous risks, including life-threatening post-operative complications (e.g. internal bleeding, infection), and long-term problems such as diarrhea, vitamin deficiency, electrolytic imbalance, unpredictable or insufficient weight loss, and gastrointestinal reflux disease (GERD). Given the above noted shortcomings, limitations and risks of prior art procedures, it is apparent there remains a need for safe, easy-to-perform and effective interventional procedures for reducing gastric volume, as well as for devices enabling such procedures.

SUMMARY OF THE INVENTION

The methods and devices of the present invention represent a new approach for reducing gastric volume, and thereby treating obesity and other disorders of the gastrointestinal tract, that is safe, effective, and overcomes many shortcomings and limitations of prior art procedures. In general, methods of the present invention involve reconfiguring a portion of the gastrointestinal tract (e.g., stomach wall) from the abdominal space, by contacting external tissue surfaces and drawing them toward one another to form one or more tissue invaginations, then approximating the shoulders of the extragastric tissue forming the invagination to form a tissue fold or plication, and then securing the shoulders of the extragastric tissue forming the plication to maintain a permanent plication. In preferred embodiments, the extragastric tissue is approximated such that external tissue surfaces abut one another to form the tissue plication, which extends into the internal gastric space. One or more plications may be formed to effectively reduce the circumference, and thereby cross-sectional area and volume, of the gastrointestinal lumen. One of the advantages of this procedure is that the gastric volume is reduced without reducing the mucosal surface area involved in digestive absorption. In a preferred embodiment of the present invention, the portion of the gastric tissue that is reconfigured, according to the procedure described above, is the anterior surface or anterior wall of the stomach, which is readily accessible from the intra-abdominal space. In another preferred embodiment of the present invention, which may allow for even greater gastric volume reduction, the portion of the gastric tissue that is reconfigured includes both the anterior surface and posterior surface of the stomach.

The methods of the present invention may be carried out using open interventional procedures, which are useful, for example, to penetrate the abdominal space and obtain access to difficult or remote regions of the abdomen and gastrointestinal tract, such as the stomach. Alternatively, however, abdominal access to the gastrointestinal tract (e.g., stomach) is provided using conventional laparoscopic procedures that involve relatively minimal penetration of the abdominal space. Minimally invasive non-laparoscopic methods may also be used (i.e. wherein access to the abdominal cavity is achieved without establishing a pneumoperitoneum via insufflation) to access the external surface(s) of the gastrointestinal tract. Numerous methods for accessing the internal abdominal space, and for monitoring intra-abdominal interventions (e.g., imaging and visualizing the intra-abdominal space and intervention) are known and may be used in conjunction with methods of the present invention.

According to one embodiment of the present invention, a method for reducing gastric volume comprises obtaining access to an external surface of the gastrointestinal tract (e.g. stomach); invaginating and approximating the wall of the gastrointestinal tract from its external surface to create at least one plication therein; and fastening surfaces of the approximated gastrointestinal wall to one another to secure the plication(s). According to another embodiment, a method for reducing gastric volume comprises obtaining access to an external surface of the gastrointestinal tract (e.g., stomach); invaginating and approximating the wall of the gastrointestinal tract from its external surface by drawing external surfaces of the gastrointestinal tract toward one another to form a plication extending into the interior space of the gastrointestinal tract; and fastening the approximated surfaces of the gastrointestinal wall to one another to secure the plication(s). This methodology provides a significant reduction in the internal volume of the gastrointestinal tract (e.g., stomach) without reducing the interior wall surface available for digestion and nutrient absorption.

The exterior serosal layer and adjacent muscularis layers of the gastrointestinal tract have relatively more strength than the submucosal and mucosal layers. In certain embodiments of methods of the present invention wherein external surfaces of the gastrointestinal wall are approximated to form a plication projecting into the internal space of the gastrointestinal tract, fastening of the approximated portions of the gastrointestinal wall is accomplished by penetrating fewer than all of the layers of the gastric wall. In preferred embodiments, fastening of the approximated portions of the gastric wall is accomplished by penetrating at least the thin, tough serosal layer covering the exterior of the gastrointestinal lumen and, optionally, the serosal and muscularis layers, without penetrating the submucosal and mucosal layers of the gastric wall. In these embodiments, the intragastric space is not breached during the procedure, and the mucosal layer of the gastrointestinal tract remains intact. This is advantageous not only because it simplifies the procedure, but also because it avoids a variety of known complications arising from prior art procedures that may result when transgastric methods are employed that puncture, damage or otherwise compromise the mucosa during the intervention. Thus, according to another embodiment, a method for reducing gastric volume comprises obtaining access to an external surface of the gastrointestinal tract (e.g. stomach); invaginating and approximating the wall of the gastrointestinal tract from its external surface to form a plication extending into the interior space of the gastrointestinal tract; and fastening approximated surfaces of the gastrointestinal wall to one another without penetrating all layers of the gastric wall to secure the plication(s). In one embodiment, the surfaces of the gastrointestinal wall are fastened to one another using fasteners that penetrate at least the serosal layer, and preferably the serosal and muscularis layers of portions of the gastrointestinal wall forming the plication.

Additional embodiments of methods of the present invention, disclosed in detail below, incorporate additional features for the purpose of improving the safety and effectiveness and/or reducing the complexity and cost of the procedure. For example, in one embodiment of methods of the present invention, immediately prior to, or contemporaneously with the above mentioned invaginating and approximating steps, serosal tissue on surfaces of the gastrointestinal wall that adjoin to form the plication is treated to promote bonding or adhesion of adjoining tissue layers within the plication. In one embodiment, bonding of adjoining tissue layers within the plication is accomplished by disrupting the serosal tissue and promoting a healing response therein. In one preferred embodiment, a serosal tissue treatment that involves serosal tissue disruption and/or promotion of the formation of a serosal-to-serosal bond is provided over substantially the gastrointestinal surface area involved in forming the one or more tissue folds.

It is known that serosal tissue is capable forming strong adhesions to itself, or adjacent tissues, following inadvertent disruption of or damage to the serosal tissue that occurs during surgery. Typically, such adhesions are considered an undesirable and sometimes dangerous complication of abdominal surgery, and avoiding inadvertent damage to the serosa to minimize the formation of adhesions is an important goal during abdominal interventions. In contrast, in methods of the present invention, serosal tissue disruption and formation of the consequent adhesions may be optionally and intentionally promoted on targeted surface areas of the gastrointestinal lumen. When combined with the invaginating and approximating methods of the present invention, it has unexpectedly been discovered that serosal adhesions can be used beneficially for the purpose of providing a supplementary or even primary securing means for the gastrointestinal reconfiguration. According to the present invention therefore, serosal tissue on surfaces of the gastrointestinal wall that form the plication may be treated to disrupt the serosal tissue and promote a healing response for the purpose of selectively promoting the formation of a serosa-to-serosa bond across the approximated tissue boundary within the gastrointestinal plication.

A strong serosa-to-serosa bond is typically formed after a relatively brief period of time (e.g. approximately 7 days after surgery). Once formed, this serosa-to-serosa bond is sufficiently strong to substantially resist the separation forces generated by the stomach during ingestion and digestion, and ensures the long-term integrity of the plication. The formation of a strong serosa-to-serosa bond in the gastric plication of the present invention significantly improves the durability and lifespan of the plication, and consequently of the gastric reduction, and offers a significant improvement compared to the (solely) mechanical fastening methods used in tissue approximation and plication in the prior art. Thus, in the present invention, the fasteners used during the intervention to initially secure the tissue fold serve as the sole structural support for securing the plication only during the brief healing phase following surgery. Following its formation, the serosa-to-serosa bond may provide the primary structural support for securing the plication, and the fasteners initially placed to secure the plication may be removed, absorbed or, more typically, left in place within the patient to provide additional support for the plication.

In contrast to Roux-en-Y or other gastrectomy procedures involving stapling, it should be pointed out that the method of the present invention does not require cutting, transection, anastomosis, or removal of any gastrointestinal tissues from the body. It is therefore possible that the gastric reduction accomplished during this procedure is interventionally reversible. For example, if at a later date the surgeon/patient elects to reverse the gastric reduction, it is possible to substantially restore the original gastrointestinal configuration using a simple and safe procedure wherein the plication is substantially eliminated by removal of any remaining implanted securing means, followed by dissection of the serosa-to-serosa bond along the original line of tissue approximation, and subsequent localized treatment to prevent further formation of adhesions during post-operative healing.

A variety of novel devices, tools and systems are provided herein that enable a medical professional to engage and approximate soft body tissues during an interventional procedure, more safely and conveniently than possible using the prior art instruments. These inventive devices, tools and systems are useful for, among a variety of other possible interventional purposes, performing gastric reduction procedures by invaginating and approximating the wall of the gastrointestinal tract from its external surface to create at least one plication therein; and fastening surfaces of the approximated gastrointestinal wall to one another to secure the plication(s).

Gastric reduction methods of the present invention are performed in the abdominal cavity and involve contacting and manipulating the gastrointestinal tract from its external surface. The methods are typically accomplished using minimally invasive laparoscopic techniques, and the devices and systems of the present invention are therefore generally intended to be used in connection with laparoscopic techniques. However, any technique that provides access to the intra-abdominal space and, particularly, the exterior surface of the gastrointestinal tract may be used, including natural orifice transluminal endoscopic surgery (NOTES) techniques and other minimally invasive non-laparoscopic techniques. For example, smaller diameter, flexible embodiments of the tissue approximation and fastening devices described in detail below can be deployed through a flexible endoscope that may be inserted into the patient's gastrointestinal tract orally, anally or vaginally, after which access to the intra-abdominal space and, particularly, the exterior surface of the gastrointestinal tract may be obtained transluminally. Such flexible, endoscopic tissue approximation and fastening devices are considered within the scope of the present invention.

In one embodiment, a specialized device is provided for carrying out the tissue invagination and approximation steps; another device may optionally be provided for disrupting and/or promoting the bonding of serosal tissue, and yet another device may be provided for securing the tissue plication(s). A device for invaginating and approximating gastric tissue of the present invention preferably comprises a tool having an actuation mechanism (generally on or in proximity to a handle) manipulable by an operator, at least one extendible member, and at least two tissue engagement mechanisms. Tissue engagement mechanisms are generally provided at or in proximity to the distal end(s) of the device or extendible member(s), but may be provided at other locations. In one embodiment, the approximation device comprises at least one tissue engagement mechanism provided in association with a device shaft that is inserted at the site of the intervention, and another tissue engagement mechanism provided in association with an extendible member. In this embodiment, tissue is approximated by engaging tissue at two spaced apart locations using the tissue engagement mechanisms and then moving the extendible member and the device shaft relative to one another to approximate the engaged tissue.

According to another embodiment, the approximation device of the present invention comprises at least one tissue engagement mechanism provided in association with each of at least two extendible members. The extendible members are adjustable by the operator between an insertion (collapsed, pre-deployed) condition, in which they may be inserted into the abdominal space, and an expanded (extended, deployed) condition, in which the associated tissue engagement mechanisms are separated and positioned to engage two portions of tissue spaced apart from one another. The extendible member(s) are also adjustable by the operator, by means of an actuation mechanism, following engagement of the two portions of tissue to draw together, or approximate, the two portions of tissue engaged by the tissue engagement mechanisms. The tissue engagement mechanisms are furthermore manipulable to release engaged tissue, and the extendible members are manipulable to reposition the members in a low profile, collapsed condition for withdrawal of the device from the abdominal space. Thus, in operation, the distal portion of the tissue invagination and approximation device is positioned in the abdominal space; a control feature is actuated by the operator to adjust the extendible members from a low-profile, collapsed condition to a desired extended condition; and the tissue engagement mechanisms are positioned to engage the exterior surface of spaced-apart portions of the gastrointestinal tract (e.g., stomach); a control feature is actuated by the operator to draw the tissue engagement mechanisms together and approximate the two engaged portions of tissue; the engagement mechanisms are disengaged from the tissue; and after repeating the above steps any desired number of times, the extendible members are collapsed and the device is withdrawn from the abdominal cavity.

In one embodiment, the device for invaginating and approximating gastrointestinal tissue has a selection feature that allows the medical professional to select the degree of separation of the extendible members in the expanded condition, and thereby select and control placement of the tissue engagement mechanisms and the overall size of the one or more tissue folds to provide a desired degree of gastric reduction. In another embodiment, a variety of interchangeable tools may be provided, allowing the operator to select approximation tools providing the desired placement of tissue engagement mechanisms and, consequently, the overall size of the tissue fold(s).

Another tissue invagination and approximation device of the present invention comprises a tool having at least two extendible members adjustable between a collapsed insertion condition and an extended operating condition, and additionally comprising at least one tissue invagination structure arranged and adjustable along an axis to contact and invaginate tissue located generally at a midline between the tissue portions engaged by the tissue engagement mechanisms. The tissue invagination structure is preferably axially adjustable between a withdrawn insertion condition in which it does not extend substantially beyond the terminal ends of the extendible members and an invaginating, projected condition, in which the tissue invagination structure projects toward the midline of the tissue surface engaged by the tissue engagement mechanisms. In one embodiment, the axial movement of the tissue invagination structure may be coordinated with the extension of the tissue engagement mechanisms such that, following engagement of two spaced apart portions of tissue, the tissue invagination structure is extended to contact and invaginate tissue as the approximation members are drawn together to approximate the two spaced apart tissue portions. A selection feature may allow the medical professional to select the degree of extension of the invagination structure, thereby controlling the overall size of the tissue invagination and plication, and providing a desired degree of gastric reduction.

In yet another embodiment, a serosal treatment device may be provided and used separately from or in coordination with the tissue approximation and invagination device. A serosal tissue treatment device, in one embodiment, is adapted to disrupt serosal tissue lying between spaced apart tissue surfaces engaged by the approximating members to promote healing and formation of a serosal-to-serosal bond between serosal tissue surfaces contacting one another in the plication formed during the tissue approximation. The serosal treatment device may utilize one or more mechanical structures, such as a discontinuous or a non-smooth surface structure, to disrupt serosal tissue and thereby promote serosal tissue adhesion. Additionally or alternatively, the serosal treatment device may be operated to facilitate application or administration of an agent that promotes serosal tissue disruption and/or healing in serosal-to-serosal bonds, or to administer a tissue bonding agent that promotes serosal-to-serosal tissue bonds. The serosal treatment device may incorporate an alternative modality for serosal tissue treatment, e.g., by application of heat, RF radiation, ultrasound, electromagnetic radiation, or other types of radiating energy. In one embodiment, the serosal tissue treatment device may be integrated with the approximating members and/or the tissue invagination structure, as described more fully below.

A separate tissue securing or fastening device may be provided for fastening the two adjacent portions of approximated tissue to one another to secure the plication. Suitable devices, such as suturing, stapling and other types of mechanical tissue fastening devices are well known in the art. The tissue fastening device, in one embodiment, is a multi-fire device that is capable of administering multiple fasteners, in multiple positions along a line of approximated tissue, without requiring removal from the abdominal space. Various types of fasteners and fastening devices may be used, as described more fully below.

In another embodiment, an integrated device may be provided for carrying out the tissue invagination and approximation steps, and for optionally treating serosal tissue in the invaginated tissue, while a separate device may be provided for securing the tissue plication. This beneficially eliminates the need for at least one laparoscopic incision and trocar during the procedure. In yet another embodiment, a single multi-functional device is provided that comprises tools capable of invaginating and approximating tissue, optionally treating the serosal tissue to promote a healing response, and for securing the tissue fold to produce the plication. In this embodiment, a single minimally invasive laparoscopic device is provided, thereby minimizing the number of trocars needed to complete the procedure. For example, assuming one access port is needed for the video camera and one is needed for a grasper, liver/organ manipulator, dissector, or other tissue manipulation device, the procedure may be completed using only 3 trocars. In another embodiment, the single integrated minimally invasive laparoscopic device may be optionally configured having one or more extra service channels through which the camera and other tissue manipulation devices may be inserted, thereby allowing the entire gastric reduction intervention to be completed using only a single access port. In comparison, 5 or more laparoscopic incisions are commonly needed for the Roux-en-Y procedure. Using a multi-functional tool of the present invention, the gastric reduction procedure is less invasive, requires less time to complete and therefore reduces the risks attendant any intervention, speeds patient recovery, and reduces the overall cost of treatment.

Other embodiments of medical devices of the present invention further incorporate novel tool configurations, detailed below, that enable and simplify the steps of securing the one or more tissue folds created in order to produce the one or more plications in the wall of the gastrointestinal tract. In one embodiment, means are provided for delivering individual tissue anchors comprising a securing assembly. In yet another embodiment, individual tissue anchors are reconfigured from a first state (e.g. a configuration used for delivery) to a second state (e.g. a deployed configuration). In yet another embodiment, the deployed securing assembly is configured to penetrate only the serosal and muscularis tissue layers, without penetrating completely through the wall of the gastrointestinal tract.

According to the brief summary provided above, it is apparent that methods and devices of the present invention offer several advantages over the prior art. For example, because the one or more gastric tissue plications produced may achieve substantial therapeutic gastric reductions, it is possible to obtain weight loss results comparable to prior art procedures using an interventional alternative that may be performed using minimally invasive laparoscopic or non-laparoscopic abdominal access procedures, while at the same time avoiding a variety of complications associated with malabsorption, the long-term presence of restrictive devices within the body, leakage or failure at transgastric anastomosis or anchoring sites, permanent restructuring of the gastrointestinal tract, and the like. Gastric reduction procedures of the present invention are therefore simpler, easier to perform, and safer that prior art interventional methods. In addition, the methods of the present invention, which may optionally be performed substantially or entirely extragastrically, may be carried out by conventionally skilled laparoscopic surgeons, requiring minimal specialized training to achieve substantial gastric volume reduction and effective weight loss results, while significantly reducing the risk of injury or damage to neighboring organs and other complications. This is a significant advantage compared to prior art transesophageal endoluminal interventional methods.

While the present invention will be described more fully hereinafter with reference to the accompanying drawings, in which particular embodiments are shown and explained, it is to be understood that persons skilled in the art may modify the embodiments herein described while achieving the same methods, functions and results. Accordingly, the descriptions that follow are to be understood as illustrative and exemplary of specific structures, aspects and features within the broad scope of the present invention and not as limiting of such broad scope.

BRIEF DESCRIPTION OF THE FIGURES

FIGS. 1A-1B2 schematically illustrate an interventional method according to one embodiment of the present invention, wherein FIGS. 1A-1A3 shows the pre-procedure tissue configuration; and FIGS. 1B-1B2 show the post procedure tissue configuration.

FIGS. 2A-2E2 schematically illustrate an exemplary interventional gastric reduction method according to one embodiment of the present invention.

FIGS. 5A-5F illustrate operation of a medical device according to one embodiment of the present invention, wherein FIG. 5A shows an overview; FIG. 5B shows a close-up, distal end of the device in a collapsed state; FIG. 5C shows a close-up, distal end of the device in an extended state; FIG. 5D shows the device in an extended state following tissue engagement; FIG. 5E illustrates partial retraction of the extendible members and tissue engagement mechanisms and actuation of a projecting serosal tissue treatment member during invagination and approximation; and FIG. 5F illustrates complete retraction of the extendible members and full extension of the projecting serosal tissue treatment member to form the plication.

FIGS. 6A-6D illustrate a medical device system according to one embodiment of the present invention, wherein FIG. 6A shows separate tools positioning; FIG. 6B shows the tissue fold created; FIG. 6C shows the fasteners applied; and FIG. 6D shows a plurality of fasteners.

FIGS. 7A-7H illustrate a medical device according to one embodiment of the present invention, wherein FIG. 7A shows an overview; FIG. 7B shows the distal end in collapsed state; FIG. 7C shows the distal end in expanded state; FIG. 7D shows the tissue engagement; FIG. 7E shows the tissue invagination and approximation; FIG. 7F shows the tissue fold created; FIG. 7G shows the securing means applied, with the distal end retracted to collapsed state; and FIG. 7H shows a plurality of securing means.

FIGS. 8A and 8B illustrate a device for approximating tissue according to one embodiment of the present invention, wherein FIG. 8A shows the pre-deployed configuration and FIG. 8B shows the deployed configuration.

FIGS. 9A and 9B show a cross sectional view of the proximal end of a device for approximating tissue according to one embodiment of the present invention, wherein FIG. 9A shows the pre-deployed configuration and FIG. 9B shows the deployed configuration.

FIGS. 11A and 11B show a cross sectional view of the distal end of a device for approximating tissue according to one embodiment of the present invention, wherein FIG. 11A shows the pre-deployed configuration and FIG. 11B shows the deployed configuration.

FIGS. 12A-12C illustrate operation of a device for approximating tissue according to one embodiment of the present invention, wherein FIG. 12A shows close-up views of the proximal and distal ends in the deployed configuration and engaging tissue; FIG. 12B shows partial retraction of the device to approximate tissue and create an invaginated tissue fold; and FIG. 12C shows complete retraction of the device, complete invaginated tissue fold created.

FIGS. 20A and 20B show cross sectional views of a fastener applicator according to one embodiment of the present invention, wherein FIG. 20A shows the proximal end; and FIG. 20B shows the distal end.

FIGS. 21A-21E show cross sectional views of the distal end a fastener applicator according to one embodiment of the present invention illustrating the firing sequence, wherein FIG. 21A shows the pre-fired configuration; FIG. 21B shows the trigger retracted with the fastener being loaded; FIG. 21C shows the device fully cocked and ready to fire; FIG. 21D shows the device firing with the fastener being propelled out of device; and FIG. 21E shows the firing complete with the fastener propelled beyond the distal end of the device, and device returned to its pre-fired configuration.

FIGS. 22A-22C illustrate the combined operation of a device for approximating tissue and a fastener applicator according to one embodiment of the present invention, wherein FIG. 22A shows the device invaginating tissue, immediately prior to tissue engagement; FIG. 22B shows a close up of the distal end of the devices after tissue engagement and during creation of an invaginated tissue fold; and FIG. 22C shows multiple fasteners inserted to secure the tissue fold, thereby producing a plication.

FIGS. 23A-23D show cross sectional views of the distal end of a tissue approximating device that articulates by pivot means, wherein FIG. 23A shows the linear, retracted configuration; FIG. 23B shows the linear deployed configuration; FIG. 23C shows the bent, retracted configuration; and FIG. 23D shows the bent, deployed configuration.

FIGS. 24A and 24B illustrate the distal end of a tissue approximating device that articulates by flexible member means, wherein FIG. 24A shows the linear, retracted configuration; and FIG. 24B shows the bent, deployed configuration.

FIGS. 25A and 25B illustrate the distal end of an alternative tissue approximating device that articulates by flexible member means, wherein FIG. 25A shows the linear, retracted configuration; and FIG. 25B shows the bent, deployed configuration.

FIGS. 26A and 26B illustrate an embodiment of a fastener of the present invention, wherein FIG. 26A shows the deployed configuration; and FIG. 26B shows the pre-deployed configuration.

FIGS. 27A-27C illustrate deployment of a fastener of the present invention, wherein FIG. 27A shows the fastener penetrating the tissue surface; FIG. 27B shows fastener self-reconfiguration during deployment; and FIG. 27C shows the fastener fully deployed in tissue.

FIGS. 28A and 28B illustrate two different fastener placements for securing a tissue fold to produce a plication according to the present invention, wherein FIG. 28A shows the fastener penetrating completely through the tissue; and FIG. 28B shows the fastener not penetrating completely through the tissue.

FIGS. 29A and 29B illustrate alternative embodiments for fastener applicators according to the present invention, wherein FIG. 29A shows the fastener being deployed directly from a central channel; and FIG. 29B shows the fastener being deployed with the aid of insertion guides.

FIGS. 30A and 30B illustrate one embodiment of an integrated all-in-one device for approximating and fastening tissue, wherein FIG. 30A shows an overview; and FIG. 30B shows a close up of the distal end.

FIGS. 31A-31C illustrate use of a device according to one embodiment of the present invention for performing the surgical procedure of the present invention, wherein FIG. 31A shows formation of an invaginated tissue fold; FIG. 31B shows deployment of a fastener into the approximated shoulders of the invaginated tissue fold; and FIG. 31C shows the fastener securing the tissue fold to produce a plication.

FIGS. 32A-32C illustrate use of a device according to another embodiment of the present invention for performing the surgical procedure of the present invention, wherein FIG. 31A shows formation of an invaginated tissue fold; FIG. 31B shows deployment of a fastener into the approximated shoulders of the invaginated tissue fold with the aid of insertion guides; and FIG. 31C shows the fastener securing the tissue fold to produce a plication.

FIGS. 33A and 33B illustrate an embodiment of a fastener of the present invention, wherein FIG. 33A shows the deployed configuration; and FIG. 33B shows the pre-deployed configuration.

FIGS. 34A-34C illustrate deployment of a fastener of the present invention, wherein FIG. 34A shows the fastener penetrating the tissue surface; FIG. 34B shows fastener self-reconfiguration during deployment; and FIG. 34C shows the fastener fully deployed in tissue.

FIGS. 35A-35C illustrate use of a device according to one embodiment of the present invention for performing the surgical procedure of the present invention, wherein FIG. 35A shows formation of an invaginated tissue fold; FIG. 35B shows deployment of a fastener into the approximated shoulders of the invaginated tissue fold; and FIG. 35C shows the fastener securing the tissue fold to produce a plication.

DETAILED DESCRIPTION OF THE INVENTION

Figure 3A:
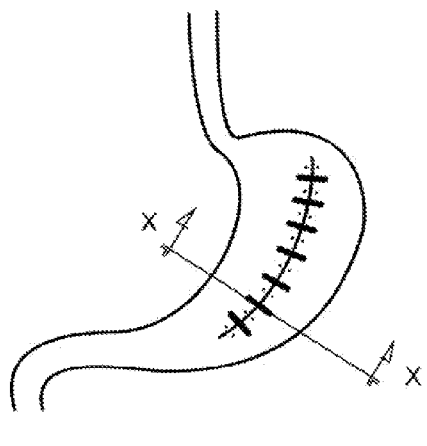
FIGS. 3A and 3B show an organ having a plication and a cross sectional view of a plication, illustrating securing means applied according to one embodiment of the present invention.

Methods of the present invention provide effective reduction of the functional volume of the gastrointestinal tract (e.g., stomach) using an extragastric gastroplasty procedure. In this procedure, a portion of the gastrointestinal tract is reconfigured by invaginating and approximating tissue to form one or more tissue folds, and then securing the one or more tissue folds in order to produce one or more plications. While the following detailed descriptions refer in general to reducing the functional volume of the gastrointestinal tract, the stomach in particular, it should be recognized that the invaginaton, approximation and securing methods of the present invention may be used on other body tissues and for other interventional purposes, within the scope of the present invention.

Gastric reduction procedures of the present invention generally access the gastrointestinal tract via the abdominal cavity. This is most typically accomplished using conventional laparoscopic techniques wherein the patient is anesthestetized, one or more small incisions are made through the abdominal wall, and a pneumoperitoneum is established by insufflation, thereby allowing the insertion of imaging devices and one or more interventional instruments through laparoscopic ports, also known as trocars. Alternatively, methods of the present invention may also be carried out when access to the abdominal cavity and gastrointestinal tract is obtained using even less invasive, non-laparoscopic techniques. A variety of such non-laparoscopic techniques may be utilized within the scope of the present invention, typically involving grasping and lifting, or otherwise retracting the abdominal wall to create sufficient working space within the abdominal cavity, without the need for insufflation. Alternatively, the methods and devices of the present invention may also be adapted for flexible endoscopic use, allowing access to the abdominal cavity and external surface of the gastrointestinal tract to be obtained by first entering the body through a natural orifice (e.g esophagus, anus or vagina), then penetrating through the wall of an anatomical lumen into the abdominal cavity.

Once abdominal access has been obtained, the medical professional employs one or more cameras or other imaging devices, along with a variety of tools known in the art, to manipulate the internal organs and/or tissues to expose the region of the gastrointestinal tract of interest. In preferred embodiments of the present invention, at least the anterior portion of the stomach is exposed sufficiently to allow for its reconfiguration. This may require dissection and/or removal of at least a portion of the omentum, and it may require lifting and/or partial retraction of the liver, both of which are relatively simple interventional steps that are well known in the art. The subsequent reconfiguration and gastric reduction may then be performed, preferably using the devices and systems of the present invention, which are described in detail below.

FIG. 1 schematically illustrates the relevant portion of the gastrointestinal tract (anterior view), both pre-procedure (FIG. 1A) and post-procedure (FIG. 1B). To aid in the following discussion, it is helpful to first distinguish the various anatomical structures in FIG. 1A. The stomach itself lies between the esophagus 105 and pylorus 110. The anterior wall 115 of the stomach is shown, along with the fundus 120, the greater curvature 125, and lesser curvature 130. Two cross-sectional views of the stomach are shown in FIG. 1A1 at X-X and in FIG. 1A2 at Y-Y. It is helpful to point out the major tissue layers of the stomach wall, as illustrated in FIG. 1A3. Starting intragastrically and moving outward, the innermost tissue layer is the mucosal tissue layer 150, then there is a submucosal connective tissue layer 152, the muscularis tissue layer 155, and the exterior serosal tissue layer 160 that covers the extragastric surface of the stomach.

FIG. 1B illustrates a stomach following gastric reduction according to methods of the present invention. As shown in FIGS. 1B1 and 1B2, the stomach now exhibits a significantly reduced cross sectional area (e.g. at X-X and Y-Y) and the functional volume of the stomach has been decreased approximately 50% as a result of single fold 180 being placed in the anterior wall 115 of the stomach. As shown, fold 180 is located approximately midway between the greater curvature 125 and lesser curvature 130, and extends approximately longitudinally from near fundus 120 to near pylorus 110. As can be seen in sections X-X and Y-Y of FIGS. 1B1 and 1B2, fold 180 was created by invaginating and approximating the tissue of the anterior wall 115 of the stomach so as to bring the serosal tissue layer 160 into contact with itself. Fasteners are then applied to the tissue brought together to produce the plication in the wall of the stomach.

In a preferred embodiment of the present invention, a single fold and plication is produced in the above described manner and location, as illustrated in FIG. 1B; however, in other embodiments, two or more such plications may be produced. Although the plication is illustrated as being formed approximately midway between the greater and lesser curvatures of the stomach, it will be appreciated that other areas of the stomach or gastrointestinal wall may be used, as may be necessary based on individual anatomy and the surgeon's desire to achieve the targeted functional gastric reduction, while minimizing the overall invasiveness of the procedure. According to the present invention the functional volume of the stomach is preferably decreased at least 20%, is more preferably decreased at least 30%, and is most preferably decreased at least 40%. In morbidly obese patients, a functional volume reduction of 50% or more may be achieved in order the promote the desired excessive weight loss. In one live animal surgery where the devices described below have been tested in a clinical setting, it has unexpectedly been found that volume reductions exceeding 80% are possible by exposing and plicating along substantially the full length of the greater curvature of the stomach.

In FIG. 1B, securing means comprising a row of individual staples 185 are placed substantially along the length of fold 180. As shown in FIG. 1B2 at section Y-Y, staples 185 grasp tissue shoulders 195 that are formed where the opposing tissue layers of the tissue fold intersect the circumference of the stomach. As can also be seen in section Y-Y, according to a preferred embodiment of the present invention, staples 185 engage tissue shoulders 195 by penetrating only through serosal tissue layer 160 and underlying muscularis tissue layer 155, without penetrating completely through the stomach wall to breach or otherwise compromise mucosal tissue layer 150. As can also be seen in section Y-Y, according to another preferred embodiment of the present invention, the approximated tissue surfaces within the tissue fold are configured such that there is substantially intimate serosal-to-serosa contact within the plication 190.

FIG. 2 illustrates in greater detail the intermediate steps of the procedure, according to one embodiment of the present invention. FIG. 2A and FIG. 2E are identical to FIG. 1A and FIG. 1B, respectively, and are repeated for completeness. FIG. 2B, FIG. 2C and FIG. 2D are helpful to explain other aspects of the intermediate steps. In FIG. 2B, for example, prior to commencing with the reconfiguration portion of the procedure, the region of interest on anterior wall 115 may be visually identified, marked or mapped out to aid subsequent steps of the procedure. For example, it may be desirable to identify and/or indicate the target position and length of the fold centerline 202, as well as the bounding lines 204 and 206 where the tissue will be contacted, engaged and/or secured. The location of bounding lines 204 and 206 define the depth of the tissue fold to be created, as well as the surface area of tissue that will be approximated during creation of the tissue fold. Identification, marking and/or mapping of the tissue structures and/or locations can be carried out according to methods well known in the art, for example, inks, dyes, adhesives, implantable tags, clips, fasteners, radio-opaque markers, fluorescent markers, cauterizing marks, and the like, may be used.

FIG. 2C schematically illustrates the early steps in the procedure, starting at one end of the target area (e.g. near the pylorus) and working progressively in one direction (e.g. toward the fundus). It should be recognized, however, that this progression is optional, and that it is just as feasible to start near the fundus and work toward the pylorus, to start anywhere along the length of the intended fold and work in both directions, or any combination of the foregoing. To form a tissue fold, the tissue is contacted and/or engaged at two or more locations, and various combinations of relative motions are then used to ensure the tissue is invaginated as the opposing tissue surfaces are approximated. Examples of such combinations of relative motions include one or more motions selected from the group consisting of pushing motions, pulling motions, twisting motions, and shearing motions.

In FIG. 2C, for example, tissue is contacted and engaged at locations 208 and 210 on opposite sides of a fold centerline location 212. Relative motion between central location 212 and the tissue contact and engagement locations 208 and 210, is represented in FIG. 2C1 by pushing force vector 214 and pulling force vectors 216 and 218, respectively. These motions invaginate the tissue and approximate the opposing tissue surfaces, while bringing tissue shoulders 195 toward each other for subsequent securing. The relative motion illustrated may be achieved, for example, by holding central location 212 substantially stationary and pulling the tissue engagement points 208 and 210, or by holding the tissue engagement points 208 and 210 substantially stationary and pushing on the central location 212, or alternatively, any combination of pushing and pulling may be used to achieve the same effect.

After the tissue has been approximated to create the tissue fold 180 as described above, and tissue shoulders 195 have been brought together into proximity of one another, a tissue fastener 185 is then applied at that location to secure the plication 190, as shown in FIG. 2D. In FIG. 2D, exemplary tissue fastener 185 is schematically shown as a box-type of interventional staple, similar in form and function to a box-type staple known in the art of interventional skin stapling for use in wound closure applications. However, it should be obvious to those skilled in the art that, within the scope of the present invention, a wide variety of mechanical elements may be used as tissue fasteners 185 for the purpose of anchoring, fastening, holding, attaching, or otherwise securing tissue surfaces 180 to produce plication 190. Examples of suitable tissue fasteners that may be used include but are not limited to sutures, staples, screws, tacks (e.g. U-shaped, circular and helical fasteners), clips, hooks, clamps, t-tags, and the like. In a preferred embodiment of the present invention, tissue fasteners 185 are preferably applied at least directly across tissue shoulders 195 at more than one location along the length of tissue fold 180, more preferably at several relatively closely spaced locations to secure the plication.

The tissue engagement, approximation and fastening steps are repeated any number of times as is necessary to completely form and secure the one or more tissue plications. In the example provided herein, the final result is shown schematically in FIG. 2E.

For convenience, the procedure may progress sequentially in one direction along the length of the intended fold, as illustrated in FIG. 2D, effectively producing the plication in a manner similar to closing a zipper. However, sequential advancement is not required, and the surgeon may use discretion in deciding where to begin and how to advance the procedure.

At each of one or more locations along the length of the intended fold, the tissue is invaginated, approximated and secured with one or more tissue fasteners before moving to the next location. In one embodiment, a device may be provided that allows simultaneous or sequential placement of multiple tissue fasteners while the invaginating and approximating tool is placed and held at one location. Alternatively, in another embodiment, a device may be provided that allows placement of a single tissue fastener along a substantial length, or even along the complete length, of the tissue fold, while the invaginating and approximating tool is held at one location.

According to one embodiment of the present invention, prior to securing the approximated tissue to produce the one or more plications, at least a portion of the surface area of the serosal tissue enfolded by the one or more plications is selectively treated to promote serosal-to-serosal tissue bonding. There is a considerable body of clinical knowledge regarding the mechanisms of abdominal adhesion formation, and a variety of methods known to those skilled in the art may be used to selectively treat the serosal tissue surfaces to promote tissue adhesion of the serosal tissue layers adjoining one another inside the tissue fold forming the plication. Examples of such tissue treatments include but are not limited to mechanical disruption methods (e.g. abrasion), energy deposition methods (e.g. RF, ultrasonic, electromagnetic, and the like), methods involving treatment using liquids (e.g. chemicals, pharmaceuticals, adhesives, etc.) and methods involving treatment using solids (e.g. powders, films, etc.). Regardless of the tissue treatment method used, an important aspect of this embodiment is that serosal tissue bonding or adhesion is promoted over a sufficiently large interfacial surface area across the approximated tissue boundary within the plication to achieve a strong and durable serosa-to-serosa bond postoperatively.

Figure 3B:
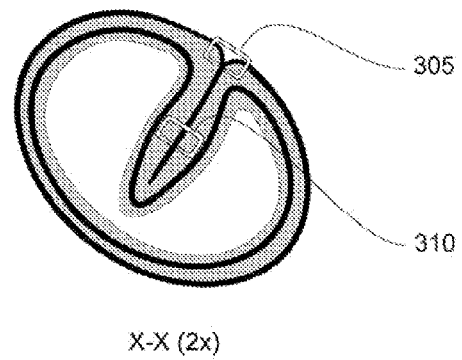

In yet another embodiment of the present invention, additional tissue fasteners may also be optionally applied while the tissues are being approximated to aid in forming, stabilizing and/or providing additional strength to the resulting tissue plication, as well as to further promote the formation of a strong serosa-to-serosa bond inside the plication. For example, as illustrated in the enlarged cross sectional view X-X shown in FIG. 3B, in addition to outer tissue fastener 305 (similar to the tissue fastener 185 described previously), one or more additional internal tissue fastener 310 may be applied across the contact area of the approximated tissue surfaces within the fold while it is being formed, such that after the plication is completed, the one or more additional internal tissue fasteners 310 are located inside the plication for the purpose of better securing the tissue across the approximated tissue surfaces. Additional internal tissue fastener 310 may be identical to outer tissue fastener 305, being placed by the same device, or in an alternative embodiment, additional internal tissue fastener 310 may have a different design and/or be placed using additional devices. Note that additional internal tissue fastener 310 also preferably penetrates only the serosal and muscularis tissue layers. Although FIG. 3 illustrates the use of a box-type staple, as in the case of tissue fastener 185 described previously, this embodiment is merely illustrative and a wide variety of alternative fasteners exist that may be used for the outer tissue fastener 305 and additional internal tissue fastener 310, within the scope of the present invention.

Figure 4A:
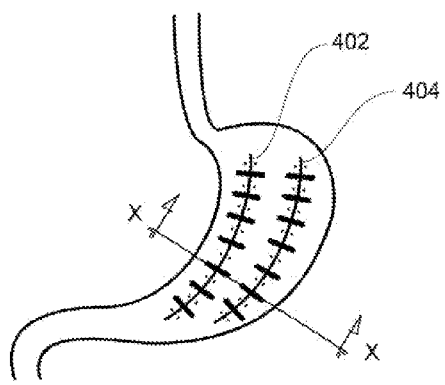
FIGS. 4A and 4B show an organ having two plications and a cross sectional view of the multiple plications according to one embodiment of the present invention.
Figure 4B:
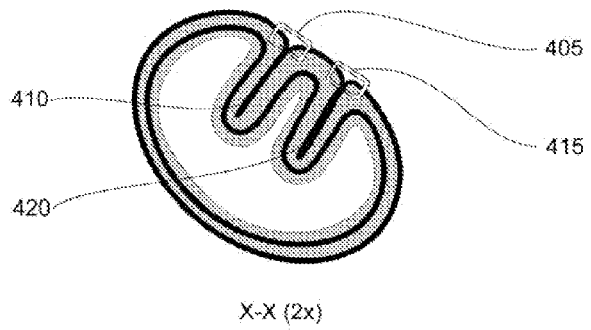

In yet another embodiment of the present invention, more than one tissue plication may be produced according to the previously described methods. For a variety of reasons, it may be advantageous in some cases to produce two or more plications. These advantages may include, for example, allowing a greater range of effective volume reductions in the stomach to be achieved, allowing smaller laparoscopic devices to be used, allowing the surgeon more flexibility in positioning of the plications relative to the stomach or surrounding organs, for reducing the maximum forces generated on the individual securing means, and so on. FIGS. 4A and 4B schematically show an example according to one embodiment of the present invention in which tissue two adjacent tissue folds 402 and 404 have been placed in the anterior wall of the stomach, running more or less parallel to one another. As can be seen in FIG. 4B in the enlarged view of cross section X-X, tissue fold 402 has been secured with tissue fastener 405 to produce a first plication 410, whereas tissue fold 404 has been secured with tissue fastener 415 to produce a second plication 420. It should be obvious to those skilled in the art that within the scope of the present invention, it is possible to produce any number of individual and separate plications in the manner described previously, each of which plication may be characterized individually in terms of length, depth, position, number and type of fasteners placed, and so on, to achieve the intended interventional result.

Interventional Devices and Systems Interventional devices for performing methods of the present invention are described herein that, taken together, comprise systems of the present invention. The devices and systems of the present invention provide the ability to carry out the above described volume reduction procedures in a safe, efficient and minimally invasive manner, which is difficult or impossible to accomplish using prior art devices. It will be appreciated that while the devices and systems of the present invention are described below with respect to their use in gastric reduction methods of the present invention, they have utility and may be used for general approximation and fastening of other types of soft body tissues and in other types of interventional procedures as well.

In general, at least one handheld interventional instrument is provided having one or more integrated tool assembly(ies) adapted for placement at an interventional site, such as within the abdominal cavity, in combination with one or more actuator(s) positioned remotely from the tool assembly and providing operator control of the tool assembly(ies) during an intervention. The tool assembly is preferably capable of engaging tissue at two or more separate locations, and then invaginating and approximating tissue to effectively create a tissue fold between the tissue engagement locations. In one embodiment, the tool assembly comprises at least two tissue engagement mechanisms (e.g. clamps, grippers, forceps, jaws, hooks, barbs, vacuum ports or the like, or combinations of these mechanisms) positioned at or in proximity to the distal end of an elongate shaft of a laparoscopic device. The tissue engagement mechanisms may be positionable by means of a remote actuator, or they may be mounted on supporting members that may be positionable to engage desired tissue sites. Using this device, the laparoscopic shaft is positioned within the abdominal cavity, and the distal end of the shaft is positioned at a first desired tissue engagement site, where a tissue engagement mechanism is engaged with the tissue. The operator then repositions the shaft by moving it to a second location, dragging the first engaged tissue location toward the second, and thereby approximating the first and second tissue locations. The approximated tissues may then be fastened to one another to secure the plication using fasteners applied with an independent device or an integrated assembly of the tissue approximation device.

In another embodiment, a first tissue engagement mechanism may be positioned at the distal end of the elongate shaft of a laparoscopic device, while a second tissue engagement mechanism may be positioned at the distal end of an extendible member that can be manipulated by an operator to move away from the axis of the device shaft to position the second tissue engagement mechanism at a second location, remote from the distal end of the device. The extendible member may be substantially rigid, or it may be flexible, or it may have both substantially rigid and flexible portions, and it may either be deployable from inside the elongate shaft of the laparoscopic device, or attached near the distal end of the shaft by mechanical means. In one embodiment, a proximal end of an extendible member is attached near the distal end of the elongate shaft using a pivot connection, a hinge connection, a flexible connection, or the like, that allows the extendible member to be operatively and selectively actuated to move its distal, operating end (comprising a tissue engagement member) away from the axis of the laparoscopic device to engage tissue. In operation, the distal end of the shaft of the laparoscopic device is first positioned at a desired tissue surface and the tissue is engaged at a first site. The extendible member and its associated tissue engagement mechanism is then deployed, extending away from the axis of the shaft to independently engage tissue at a second location. The extendible arm and its associated tissue engagement mechanism is then retracted, under control of the operator, and the second engaged tissue location is drawn in toward the axis of the shaft and thereby approximated adjacent the first engaged tissue site. An invaginated tissue fold projecting away from the distal end of the device and into the gastrointestinal space is created as the two tissue sites are drawn together and approximated.

In other embodiments, described in detail below, two or more such extendible members are provided on an interventional device, each extendible member having at least one tissue engagement mechanism, generally (but not necessarily) positioned at its distal end, such that the engagement of tissue at multiple separate locations can be accomplished without requiring the shaft of the laparoscopic device itself to contact the tissue surface. The extendible members may be actuated and positioned separately and independently of one another, or they may be actuated and positioned simultaneously and in coordination with one another. Operation of this type of device involves deploying each of the extendible members and their associated tissue engagement mechanisms, independently or in coordination, to contact the tissue engagement mechanisms at two locations on the tissue, then approximating the engaged tissue to form an invaginated tissue fold by moving at least one of the extendible members toward the other and, in some embodiments, by moving multiple extendible members toward a central location, thereby approximating the engaged tissue substantially near the distal end of the device (or along a longitudinal axis extending therefrom).

Another embodiment that provides an alternative to using two or more extendible members to engage tissue involves the use of tethers. In this case, the distal end of the shaft of a laparoscopic instrument may be positioned to sequentially engage tissue at each of two or more locations using releasable tissue engagement mechanisms mounted on retrievable tethers, wherein each tissue engagement mechanism, after being engaged in tissue, is released from the end of the shaft of the laparoscopic instrument, yet remains connected to the instrument by a tether (e.g. a suture, wire, or the like). This allows the instrument to be moved freely between each desired tissue engagement location to deploy two or more tissue engagement mechanisms at different tissue sites. Subsequently, the tethers may be selectively retrieved, or retracted back toward the shaft of the device to draw the engaged tissue sites toward one another, thereby approximating the tissue sites. Alternatively a cinching member through which the flexible tethers pass may be slid distally down the length of tethers, causing the engaged tissue locations to move toward each other, thereby approximating tissue. Retrieval of the tether(s) and/or operation of the cinching member(s) is under the control of an operator using associated actuation mechanisms.

It will be appreciated that methods and systems of the present invention may be used in connection with other diagnostic and therapeutic methods and devices. Methods of the present invention may thus be used, for example, in connection with conventional diagnostic and therapeutic methods and may involve the administration of diagnostic or therapeutic agents, agents for visualizing the interventional site, and the like. Similarly, device components of the present invention may be used in connection with various procedures and agents that are known in the art. Certain device components that are intended for introduction to the interventional site, such as tissue engagement mechanisms, probes, extendible members, fasteners, and the like may be administered in association with various types of diagnostic or therapeutic agents, or may be coated or impregnated with such materials. Suitable agents may include clotting agents, healing agents, hydrophobic and/or hydrophilic materials, agents promoting lubricity, and the like.

Figure 5A:
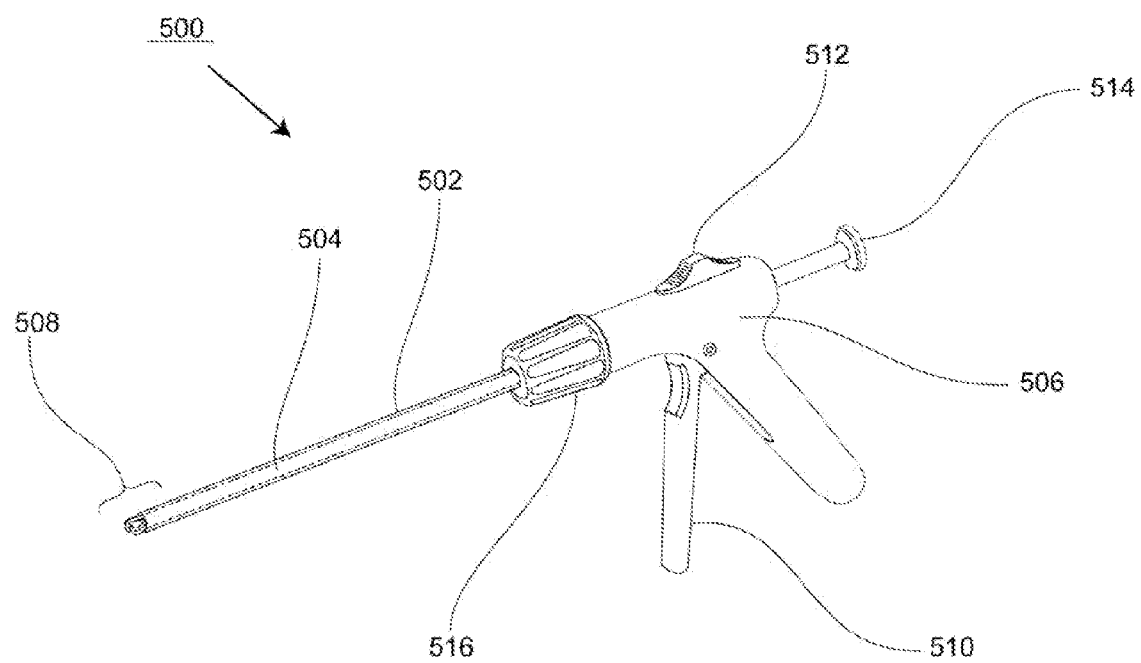
Figure 5B:
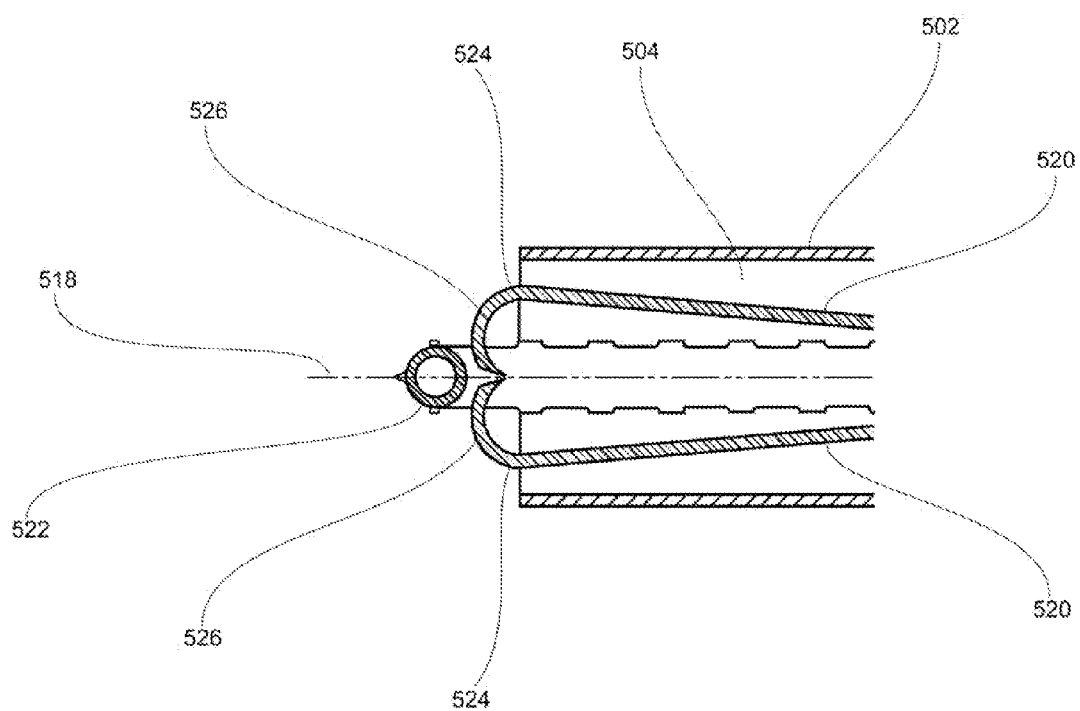

FIGS. 5A-5F illustrate an exemplary tissue approximation device according to one embodiment of the present invention. An overview of device 500 is shown in FIG. 5A in the pre-deployed configuration, and FIG. 5B shows a distal end of device 500 in the deployed configuration. Device 500 comprises an elongate tubular member 502 having at least one internal working channel 504, handle assembly 506 positioned at the proximal end, and approximating tool assembly 508 positioned at the distal end, wherein approximating tool assembly 508 is shown in the collapsed (i.e. pre-deployment or fully retracted) state, substantially confined within working channel 504. In the case of minimally invasive laparoscopic surgery, this low profile collapsed state configuration is useful for delivery of the instrument to and removal of the instrument from an internal site in the patient, such as the abdominal cavity, through a standard trocar. It is therefore generally desirable that the outer diameter of elongate tubular member 502 be as small as possible, preferably 15 mm or less, more preferably 12 mm or less and, in some embodiments, 5 mm or less. Also shown in FIG. 5A, actuating mechanisms such as a trigger 510, slider 512, and plunger 514 are provided in connection with handle assembly 506. Also shown is rotating collar 516 that allows the orientation of handle assembly 506 to be independently adjusted by the operator relative to the orientation of approximating tool assembly 508.

FIG. 5B shows an enlarged cross section view of the distal end of device 500, with approximating tool assembly 508 being shown in the collapsed state. In this configuration, located along longitudinal axis 518 of working channel 504 are two (or more) extendible members 520, and pushing member 522, each being operatively connected to an actuating mechanism operated at the handle assembly 506, as described below. Each of said extendible members 520 is configured at its distal end with a tissue engagement mechanism 524 comprising one or more mechanisms for controllably and selectively grasping, grabbing, gripping, piercing, holding or otherwise engaging tissue. In the example shown, tissue engagement mechanism 524 incorporates a tissue hook 526. Hook 526 has a generally pointed distal end for penetration of tissue and has a relatively short curved segment, thus limiting the degree of tissue penetration. Tissue engagement mechanisms having a generally pointed and sharp tissue penetration structure for penetrating tissue, such as the relatively tough serosal layer forming the exterior gastric wall, are preferred in many embodiments.

Figure 5C:
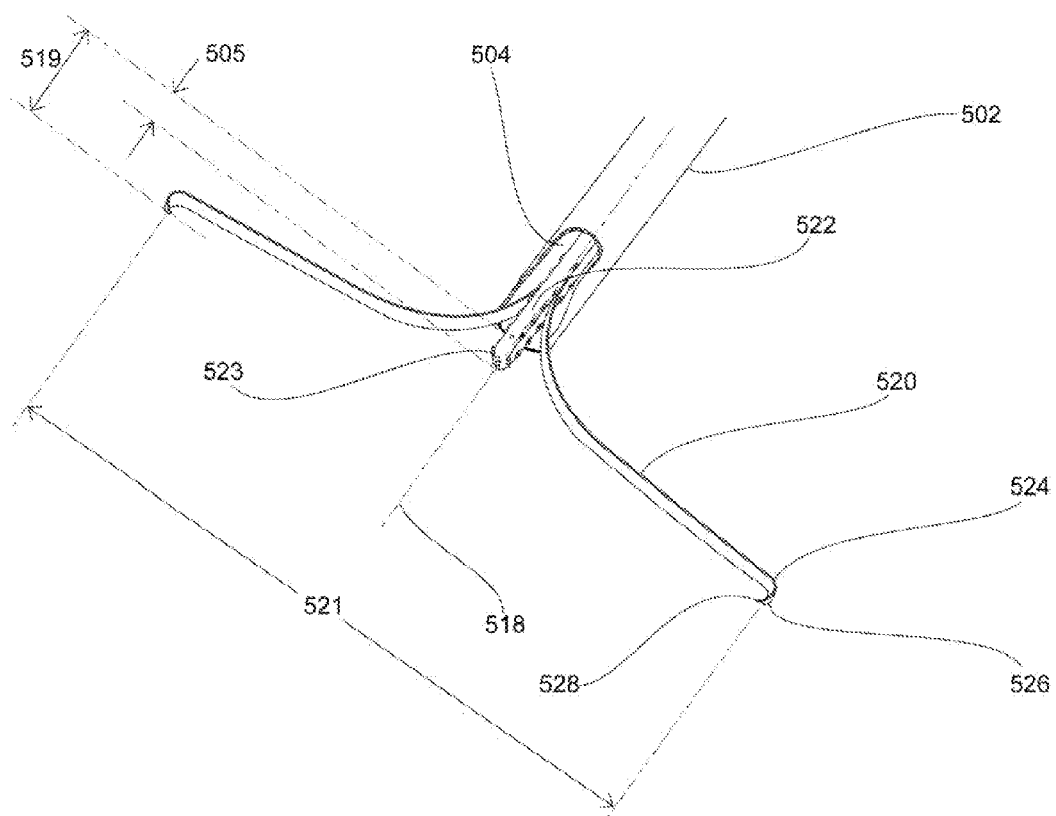

FIG. 5C shows an enlarged view of the distal end of tissue approximation device 500, with approximating tool assembly 508 being shown in the extended state, i.e. after being deployed by the operator. In this embodiment, extendible members 520 open, or extend, along a predefined path as they're released from the distal end of the shaft. An actuating mechanism such as plunger 514 is operatively connected to extendible members 520, such that when plunger 514 is axially displaced into handle assembly 506, extendible members 520 move distally along longitudinal axis 518 and thereby extend outward from working channel 504 beyond the end of elongate tubular member 502. After deployment to an expanded state, each of extendible members 520 is positioned with its distal ends 524 spaced apart from and positioned on opposite sides of longitudinal axis 518 from an opposing extendible member.

The degree of extension of the extendible members, and the spacing 521 between distal ends 524 of extendible members 520 may be governed by the degree of deployment out of shaft 502. In some embodiments, both the degree of extension of distal ends 524 from the shaft 504, indicated as longitudinal spacing 519, and the distance between extended distal ends 524 are selectably controllable by the operator to facilitate tissue engagement at desired locations, and to facilitate the creation of a tissue plication of the desired dimensions, thereby producing the desired gastric volume reduction.

Tissue approximating device 500 illustrated in FIGS. 5A-5F additionally comprises a pushing member 522 operatively connected to an actuator, such as slider 512, such that when slider 512 is translated away from its proximal (fully retracted) position, the distal end of pushing member 522 moves along longitudinal axis 518, thereby extending out of working channel 504 a distance 505 beyond the end of elongate tubular member 502. The extension of pushing member 522 facilitates invagination of a tissue fold and formation of a tissue plication as two or more tissue sites are approximated. Pushing member 522 may be operated independently of, or in coordination with, extendible members 520. In one embodiment, pushing member 522 is extended out of working channel 504 as the extendible members 520 are extended and the tissue engagement mechanisms are positioned to engage tissue.

Illustrative operation of a tissue approximation device 500 illustrated in FIGS. 5A-5F is described below. Following insertion of the shaft into the intra-abdominal space and positioning of the distal end of the shaft near a desired tissue approximation site, extendible members 520 are deployed from a collapsed state to an expanded state to prepare the device for subsequent tissue engagement steps. In one embodiment, extendible members 520 are expanded by an actuator that pushes the members out of, or releases them from the shaft, as follows. In this case, extendible members 520 are produced from a highly flexible and elastically deformable material (e.g. flexible polymers, flexible metals, shape change materials and combinations thereof may be used) and are made in a shape when in the expanded state having an outward (i.e. away from longitudinal axis 518) curvature. As the extendible members 520 are released from the working channel 504, they assume their expanded state, and the distal tissue engagement mechanisms are brought into contact with the tissue surface. Due to their flexible nature and outwardly curved shape, extendible members 520 flex elastically and continue to assume a progressively more extended condition as the operator continues releasing them from the shaft, causing distal arm portions 524 to slide outward along the tissue surface, becoming spaced apart, until the distal tissue engagement mechanisms are located in the desired positions for tissue engagement, as described below.

In another embodiment, extendible members 520 are designed to be released from the collapsed state to the expanded state in a self-actuating manner, automatically achieving the desired tissue engagement configuration when extended out of working channel 504 beyond the end of elongate tubular member 502. Such self-actuating motions can be achieved by various methods known in the art. For example, in one preferred embodiment of the present invention, extendible members 520 are produced from a highly elastic material (e.g. spring steel, hardened stainless steel, a shape change material such as a superelastic NiTi alloy, superelastic polymer, or the like) and are formed during manufacturing into the desired final deployed shape by mechanical and/or thermomechanical processing means known in the art. Extendible members 520 are then biased (i.e. mechanical potential energy is stored, similar to a pre-loaded spring) by elastically deforming and loading them into working channel 504 to thereby provide the device in its collapsed state. As extendible members 520 are then pushed out of working channel 504 during deployment, the stored energy is released and extendible members 520 automatically return to the pre-determined shape desired for subsequent tissue engagement when brought into contact with the tissue surface. It will be appreciated that different assemblies of extendible members having different dimensions, different curvatures, different elastic properties, and the like may be provided for use in a tissue approximating device of the present invention and an operator may select an appropriate extendible member assembly having the desired dimensions and extension properties and install the desired assembly in the working channel prior to an intervention.

In yet other embodiments, deployment of extendible members 520 from the collapsed state to the expanded state may be accomplished, by means of an actuating mechanism, by any combination of manual pushing to cause expansion and self-actuating expansion mechanisms. Factors that may be adjusted to optimize the above described reconfiguration and deployment motions include, for example, the cross sectional shape, curvatures, mechanical properties, length, etc. of extendible members 520. It should also be obvious to those skilled in the art that, within the scope of the present invention, other mechanical actuation mechanisms of providing the desired reconfiguration and deployment to adjust the extendible members from the collapsed state to the expanded state may also be used. Such actuating mechanisms may comprise, for example, springs, levers, cams, gears, linkages, and the like may be used.

Figure 5D:
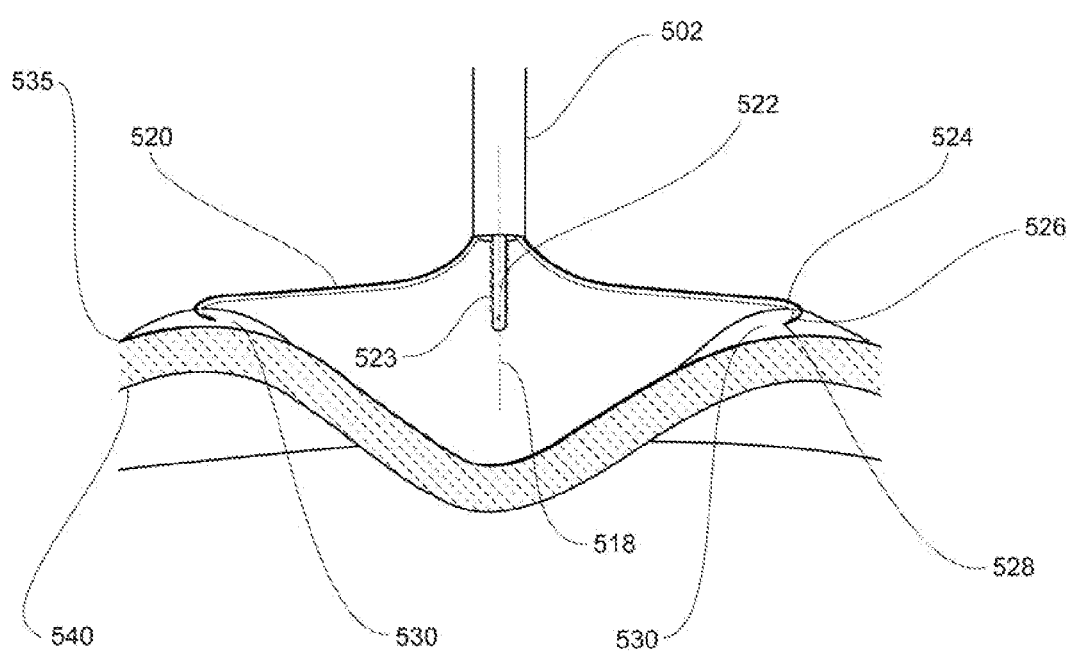

Distal ends 524 of extendible members 520 each incorporate one or more tissue engagement means configured to allow targeted tissue surface 535 to be selectively and controllably engaged by the device when actuated by the operator. Various tissue engagement mechanisms are known in the art may be employed to provide secure and robust tissue engagement having sufficient strength, for example, to allow the tissue to be subsequently pulled or otherwise manipulated without disengaging, slipping or tearing. Tissue engagement mechanisms that may be used include, for example, hooks, barbs, grippers, teeth, clamps, jaws, clips, t-tags, and the like. According to one embodiment of the present invention, as shown in FIG. 5C, tissue hooks 526 are located at the distal ends 524, and further comprise sharpened points 528 to promote tissue penetration. While extendible members 520 are in the expanded state, distal ends 524 and tissue hooks 526 are positioned such that sharpened points 528 curve slightly downward (distally) and inward (toward longitudinal axis 518). As a result, when pushed slightly downward onto the surface of the tissue, elastic deformation of extendible members 520 causes distal ends 524 to first move slightly outward. Then, when extendible members 520 are either lifted slightly (e.g. by the surgeon lifting device 500) or alternatively, when retraction of the extendible members is initiated by the operator (as described below), tissue hooks 526 move slightly downward and inward, thereby causing sharpened points 528 to pierce, penetrate and securely engage the tissue at tissue engagement locations 530, as shown in FIG. 5D. Preferably, distal ends 524, tissue hooks 526 and sharpened points 528 are designed such that secure tissue engagement is achieved by penetrating only the serosal tissue surface 535 (i.e. the serosal tissue layer), or a combination of the serosal and muscularis tissue layers, without penetrating the mucosal tissue surface 540.

While more complicated mechanical tissue engagement means may be employed in accordance with the present invention (e.g. hinged jaws, mechanical clamps, forceps, grippers, vacuum actuated mechanisms, and the like) there are several advantages to the embodiment described above, and similarly designed self-actuating embodiments. One advantage, for example, is that it is a simple, single component design having low production cost. Additionally, successful operation of this device is not particularly dependent upon operator technique (i.e. no sophisticated hand motions or unusual device manipulations are required), successful operation instead being more dependent upon device design factors that control, for example, the directions and magnitudes of the forces generated by extendible members 520 during the pushing and pulling motions involved in deployment and/or retraction of the device. Examples of design factors that may be optimized in the self-actuating design embodiments of the present invention include the shape, physical dimensions, geometrical angles, surface finish, and the like, of extendible members 520, distal ends 524, tissue hooks 526, and sharpened points 528, as well as their materials of manufacture and mechanical properties.

In one embodiment, extendible members 520 have a non-circular, generally flattened cross section to effectively increase the lateral (i.e. out of plane) stiffness when extendible members 520 are extended. Examples of suitable non-circular cross sectional shapes include square cross sections, rectangular cross sections, triangular cross sections, arcuate cross sections, hemispherical cross sections, oblong or flattened cross-sections, and combinations of the foregoing. The cross sectional shape, physical dimensions, mechanical properties, and so on, of extendible members 520 may be designed having variations along their length to provide improved deployment, tissue engagement or retraction characteristics.

Figure 5E:
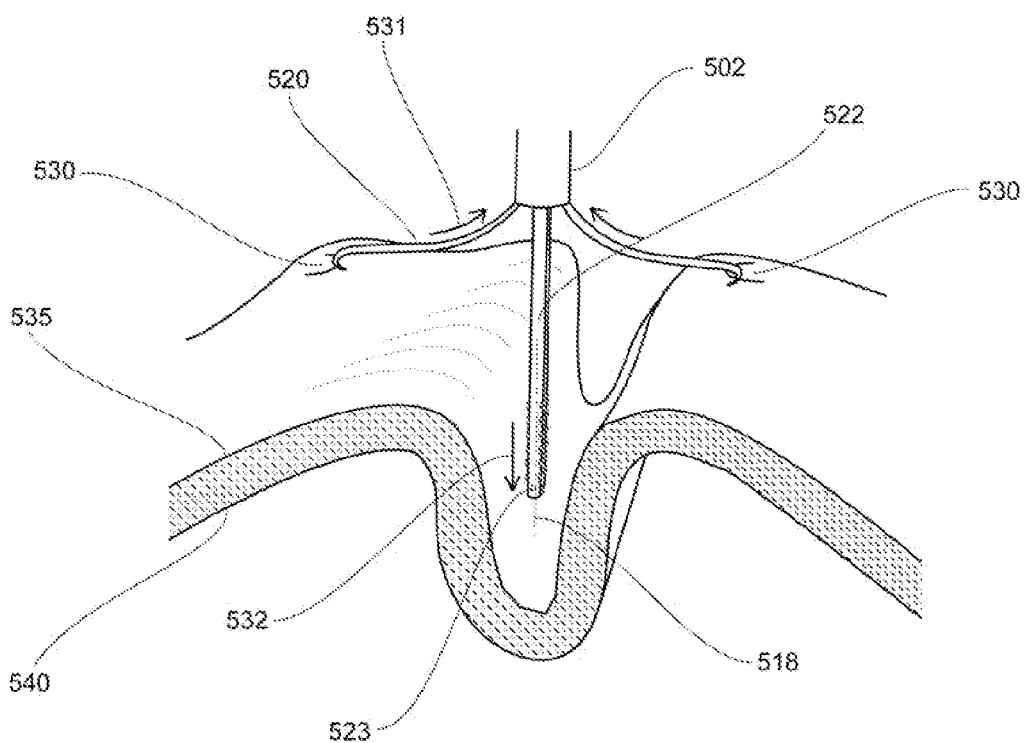

In another embodiment, extendible members 520 have a pre-determined shape when in the expanded state that includes at least two bends having radii of curvature in substantially opposing directions. Such a shape, as illustrated in FIGS. 5C-5E and explained above, may be utilized to initially give rise to a slight downward motion of distal ends 524, in addition to the inward motion that occurs during the retraction of extendible members 520 back into working channel 504, wherein the combined initial downward and inward motions of distal ends 524 effectively promotes tissue penetration and secure tissue engagement of sharpened points 528 on tissue hooks 526 upon actuated retraction of extendible members 520. The combined initial downward and inward motions of distal ends 524 that promote tissue penetration and secure tissue engagement may also be achieved using other designs obvious to those skilled in the art. This embodiment simplifies the operation, improves consistency, reduces procedural times and risk of complications, by minimizing reliance on individual operator technique and instead taking advantage of highly controlled and repeatable device motions.

After tissue has been securely engaged by approximating tool assembly 508, as described above, the operator actuates device 500 to initiate the tissue invagination and approximation step, wherein the desired tissue fold is formed by bringing serosal tissue surfaces between the engaged tissue sites in contact with each other, so that the mucosal tissue surface 540 forms a plication extending into the gastrointestinal lumen. FIG. 5E illustrates this process. In the example provided, the operator selectively activates device 500 remotely using trigger 510 provided within handle assembly 506, which is operatively connected to extendible members 520 in a manner such that, as trigger 510 is squeezed, extendible members 520 are thereby controllably retracted and pulled back into working channel 504, as indicated by retraction forces 531. The mechanisms used to operatively connect trigger 510 to extendible members 520 may include various mechanical elements known to those skilled in the art, such as gears, transmissions, levers, pivots, linkages, and the like, whether manual or automated, in order to provide the retraction forces at the working (distal) end of the device, while keeping the actuating mechanisms operated by the operator at a convenient level.

Figure 5F:
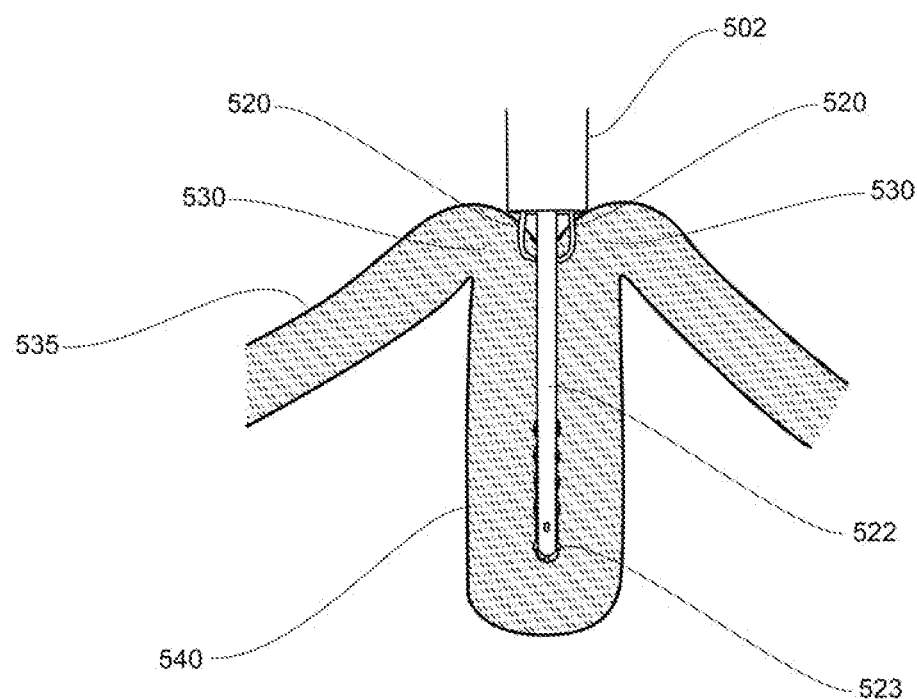

The retraction of extendible members 520 causes tissue engagement locations 530 to be gradually pulled inward toward longitudinal axis 518. In one device embodiment that incorporates a pushing member, the operator may selectively and independently actuate pushing member 522 from within handle assembly 506 (i.e. using slider 512) as the tissue engagement locations are drawn toward one another. The pushing member is extended distally along longitudinal axis 518 to contact and push against the tissue, e.g. with pushing force 532, at a location between tissue engagement points 530. This promotes tissue invagination in the desired manner while the engaged tissue is approximated, as shown in FIG. 5E. Once extendible members 520 have been fully retracted by complete actuation of trigger 510, the tissue engagement locations 530 have been brought into approximation near the distal end of elongate tubular member 502 to create tissue fold 540 as shown in FIG. 5F. In this illustration, pushing member 522 is shown remaining in the fully extended position.

The combination of extendible members and a pushing member in devices of the present invention, enabling the combined action of pulling tissue engagement points 530 toward one another via retraction of extendible members 520 while simultaneously having the user selectable option to push against the tissue between tissue engagement points 530 with pushing member 522 promotes creation of a uniform and consistent tissue fold, as shown in FIG. 5F. In preferred embodiments of the present invention therefore, operation of the device in the described manner effectively approximates opposing serosal tissue surfaces 535 inside the tissue fold, providing substantially intimate serosa-to-serosa contact, without forming wrinkles, bunches, gaps, or the like, and without penetrating the mucosal tissue surface 540.

In other embodiments of the present invention, additional user selectable controls may be optionally provided within handle assembly 506. For example, controls may be optionally provided to allow the surgeon to adjust the span 521 of extendible members 520 when in the expanded state, and the distal extension distance 505 and pushing force 532 of pushing member 522. Independent, operator controlled actuation mechanisms may be provided for each of the more than one extendible member 520, and the actuation mechanisms may control the speed and force that may be used to retract extendible members 520, as well as other operating parameters. It should also be recognized that the actuation means described above are exemplary, and that other actuation and control mechanisms that are known to those skilled in the art may be used and are considered within the scope of the present invention. For example, actuation may be accomplished manually by one or more various means known in the art (e.g. triggers, levers, buttons, knobs, or the like) or by one or more various powered means known in the art (e.g. AC or DC electric motors, compressed gas, vacuum, or the like), or by any combination of the foregoing.

As described previously, according to one embodiment of the present invention, it is desirable to selectively and therapeutically treat the serosal tissue layer to promote bonding or adhesion of the serosal layers that abut one another within the plication. This may be accomplished using device 500 in various ways. For example, in one embodiment illustrated in FIGS. 5C-5F, the distal tip and/or lateral surfaces of pushing member 522 may be used to mechanically disturb and disrupt the thin layer of mesothelial cells that form the outermost covering of the serosa. Since the layer of mesothelial cells covering the serosa is quite thin and fragile, it is easily disrupted, and pushing member 522 may be scraped, dragged or otherwise frictionally moved across the surface of the tissue to produce the desired disruption. To further aid in disrupting the serosal tissue surface and promote tissue adhesion, pushing member 522 may be modified, for example, by incorporating roughening features 523, illustrated as protuberances in FIGS. 5C-5F. As will be obvious to those skilled in the art, a wide variety of such roughening features and arrangements may be used to accomplish the desired serosal treatment, for example, ridges, bumps, bristles, teeth, scales, serrations, and the like may be used.

The optional serosal treatment described above may be carried out before the tissue fold is formed, after the tissue fold is formed but prior to the securing means is applied, after the tissue fold is formed and the securing means is applied, or any combination of the foregoing. For example, prior to actuating extendible members 520 to engage tissue, the distal end of pushing member 522 may be moved across substantially the identified area of serosal tissue to be included within the tissue fold in a sweeping or painting type of motion. Alternatively, the lateral surfaces of pushing member 522 contact and slide across the opposing serosal tissue surfaces of the tissue fold when pushing member 522 is retracted from within the tissue fold (as is evident in FIG. 5F), thereby disrupting at least a substantial portion of the serosal tissue surface during normal device operation. In this case, roughening features 523 present on the lateral surfaces of pushing member 522 may ensure more uniform and consistent serosal treatment, leading to a more effective and stronger serosa-to-serosa tissue bond.

In another serosal treatment embodiment, ports may be provided near the distal tip of shaft 502 and/or along pushing member 522 such that, when the shaft and/or pushing member lumen is connected to a supply of source material (e.g., a liquid reservoir located within or attached to the proximal handle assembly 506), the device provides controlled dispensing of a chemical or therapeutic agent (e.g. liquid, gas, solid powder, solid film, or combinations thereof) onto the tissue surface that promotes tissue bonding and adhesion. Alternatively, the distal tip of shaft 502 and/or pushing member 522 may optionally incorporate an energy deposition mechanism capable of delivering energy to the target tissue. Exemplary energy deposition mechanisms include, for example, components capable of RF cauterizing, electrocauterizing, ultrasonic vibration, and the like.

According to the present invention, once the tissue has been approximated and the desired tissue fold has been created as described above, fasteners are then applied to secure the plication. This is most conveniently accomplished while approximating tool assembly 508 is held in place by the operator to maintain the tissue in a stable, folded configuration. In one embodiment, a separate interventional instrument may be introduced through a separate trocar, and its distal tip may be positioned immediately adjacent approximating tool assembly 508. This instrument is then actuated to apply a fastener directly into and across the shoulders of the approximated tissue forming the tissue fold, thereby securing the plication. In this embodiment illustrated in FIG. 6A, a system 600 of the present invention comprises two separate handheld devices, each device capable of being actuated using controls located at their respective proximal handle assemblies. A first device 620 incorporates an approximating tool assembly 625 which may be substantially similar to approximating tool assembly 508, described above, at its distal end, and a second device 640 incorporates a fastening tool assembly 645 at its distal end, capable of applying a fastener to the tissue fold to secure the plication. A wide variety of a suitable fasteners are known to those skilled in the art and may be suitably be used as fasteners within the broad scope of the present invention. Exemplary fasteners comprise, for example, sutures, box-type staples, U-shaped or hemispherical fasteners, helical fasteners, clips, tacks, wall anchors, t-tags, and the like. A commercially available laparoscopic stapler, suturing device or tack applicator may be used to secure the tissue fold.

Figure 6A:
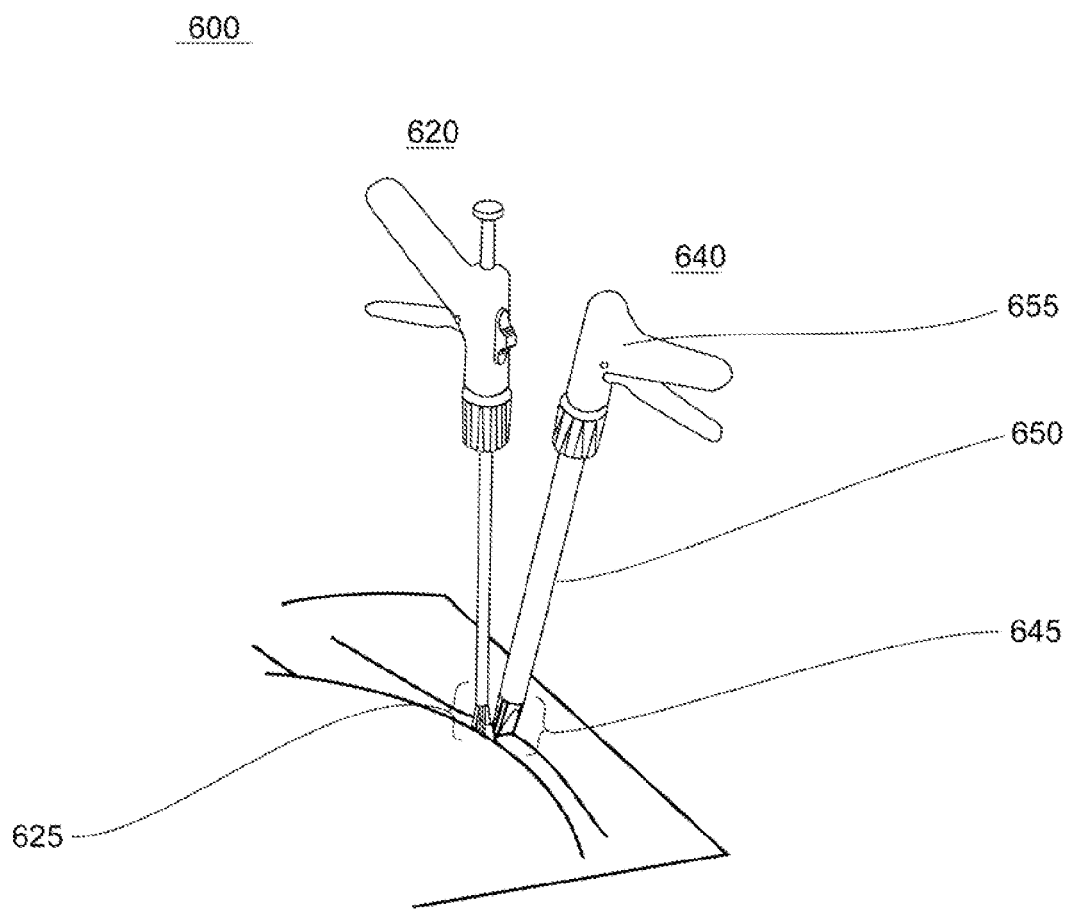

Accordingly, the laparoscopic interventional stapler shown in FIG. 6A comprises an elongate tubular shaft 650 having at its proximal end a handle assembly 655 containing user controls, actuation mechanisms, and so on, and having at its distal end a fastening tool assembly 645, which incorporates mechanisms known in the art for feeding, deploying, forming and applying to the target tissue a plurality of fasteners. These fasteners are most commonly made from stainless steel, titanium or NiTi, although other materials may also be used (e.g. other biocompatible alloys, polymers, bioabsorbable materials, and the like). Typically, a plurality of such staples would be provided within a disposable (i.e. single patient use) cartridge that is loaded at the distal end of the device, allowing multiple staples to be placed consecutively by the operator without removing the device from the patient.

Figure 6B:
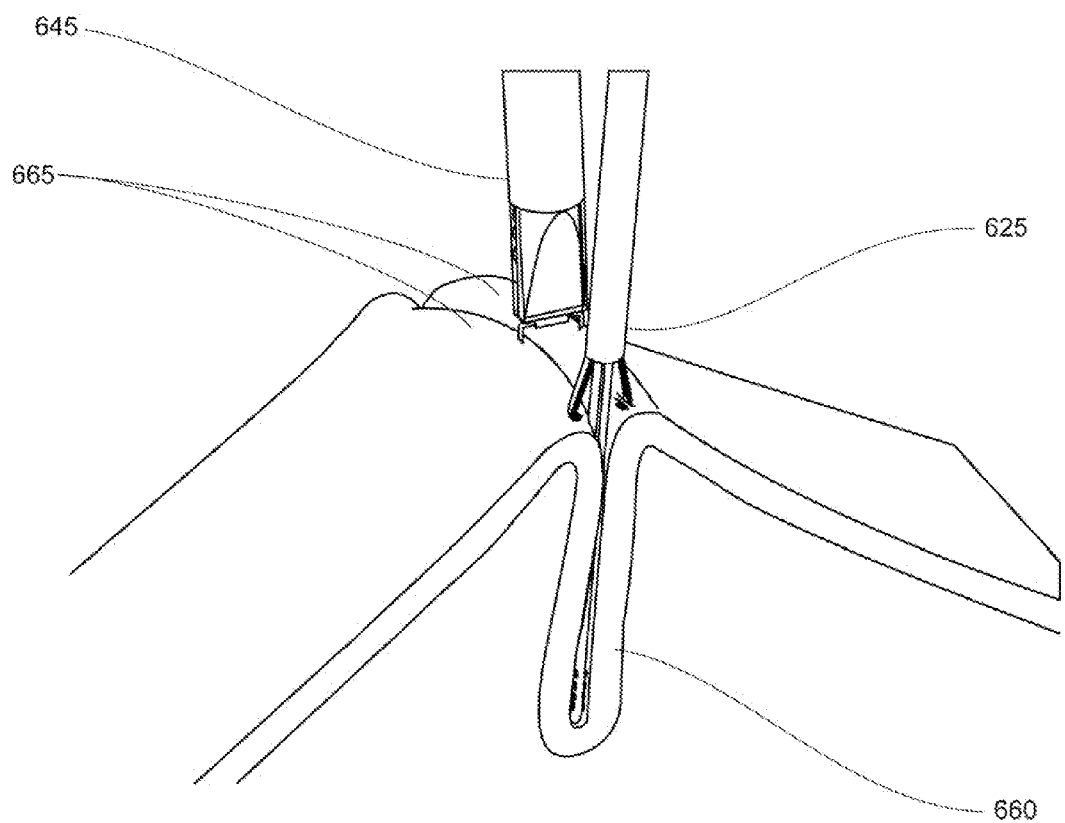
Figure 6C:
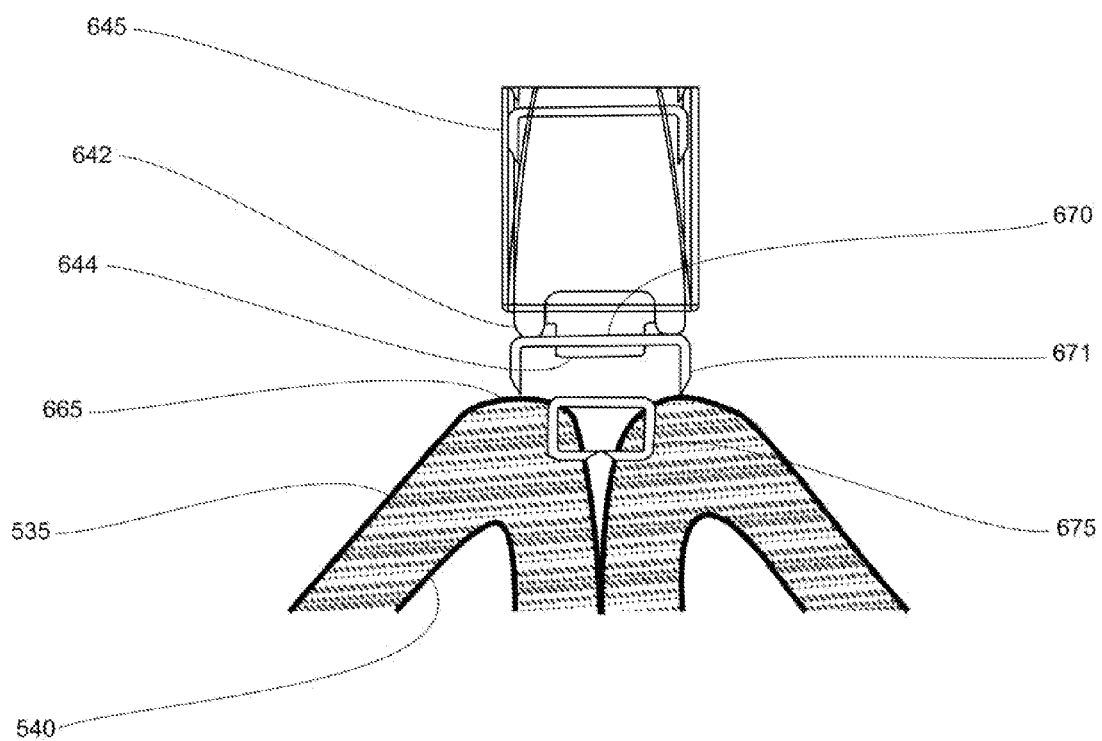
Figure 6D:
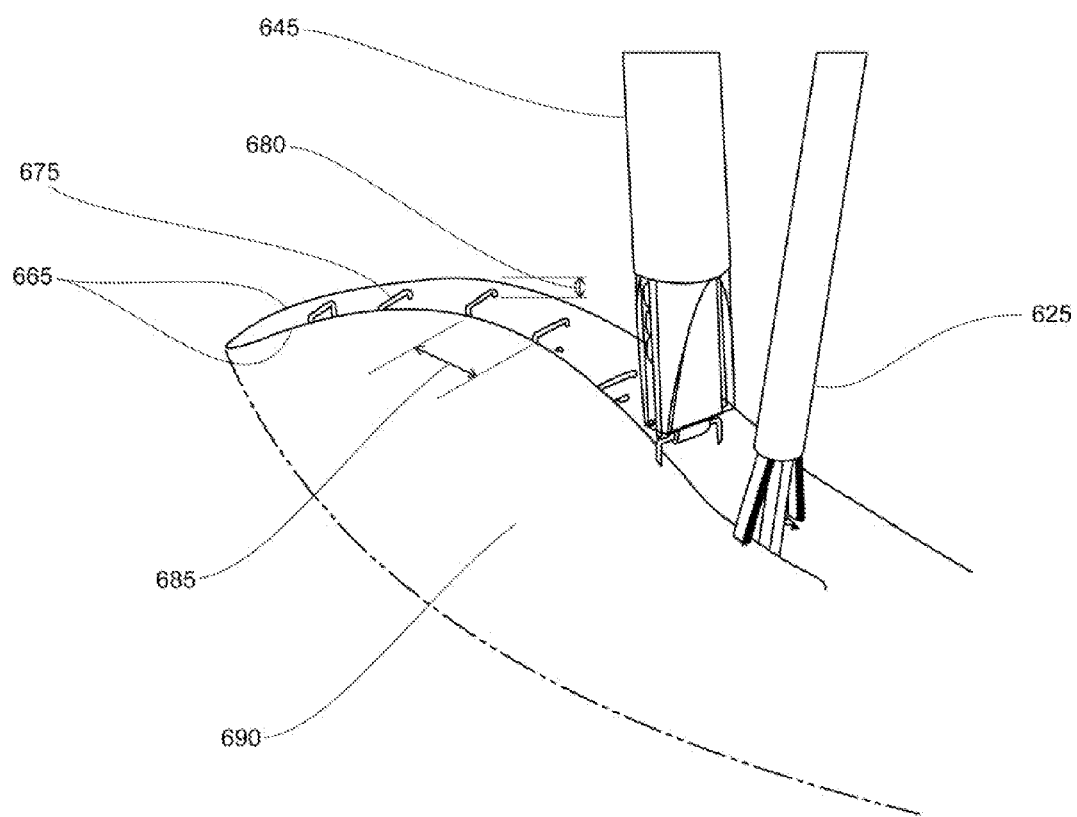

FIG. 6B shows a close up view of the distal ends of device 620 and device 640, indicating the preferred relative positioning of approximating tool assembly 625 and fastening tool assembly 645, respectively, according to one embodiment of the present invention. In this view, approximating tool assembly 625 has previously been deployed, the tissue has been engaged, and the extendible members have been retracted (these steps being carried out e.g. as described in FIG. 5), in order to create tissue fold 660. Shoulders 665 of tissue fold 660 are approximated near the distal tip of approximating tool assembly 625, and are held in position, ready for the tissue fastener to be applied by fastening tool assembly 645. The cross sectional view of FIG. 6C shows a close up of the distal tip of fastening tool assembly 645. In this example, a box-type staple in the pre-deployed state 670 is shown loaded within the within fastening tool assembly 645. Prior to applying the staple, fastening tool assembly 645 is positioned such that staple legs 671 of box-type staple in pre-deployed state 670 are positioned substantially perpendicular to, and in contact with, shoulders 665 of the tissue fold. When the surgeon fires the stapler using actuation means provided within the proximal handle assembly, extendible pistons 642 extend distally, deforming staple legs 671 around stationary anvil 644 and thereby reconfiguring the box-type staple into deployed state 675 as it is ejected from the device. As the staple is deployed, it penetrates the tissue and simultaneously pulls opposing tissue shoulders 665 toward one another, as shown. Note in this example that the box-type staple in deployed state 675 engages only the outermost layers of gastric tissue, i.e. serosal layer 535 and/or the muscularis tissue layers (not shown), and that there is no penetration through the gastric wall, which preserves the mucosal tissue layer 540 intact. FIG. 6D schematically illustrates a plication being secured using several consecutively repeated applications of the above described procedure. Approximating tool assembly 625 and fastening tool assembly 645 are shown, along with a multiplicity of individual box-type staples in the deployed state 675 that have been applied and which are arranged in a substantially continuous row extending along the length of tissue shoulders 665 to secure plication 690 projecting into the gastrointestinal space. The depth 680 below the surface and spacing 685 between the individual staple placements may be selectively controlled by the operator.

In another embodiment of the present invention, the tissue approximating and fastening functions described above requiring the use of two separately operable handheld interventional instruments are combined into a single multi-functional device having one or more integrated tools capable of invaginating and approximating tissue to create a tissue fold, as well as one or more integrated tools for applying fasteners to secure the plication. By combining these functions conveniently in a single handheld device, the overall procedure is simplified, and it can be performed without requiring extensive operator training. Furthermore, the need for one laparoscopic access port is eliminated, which provides a significant advantage.

Figure 7A:
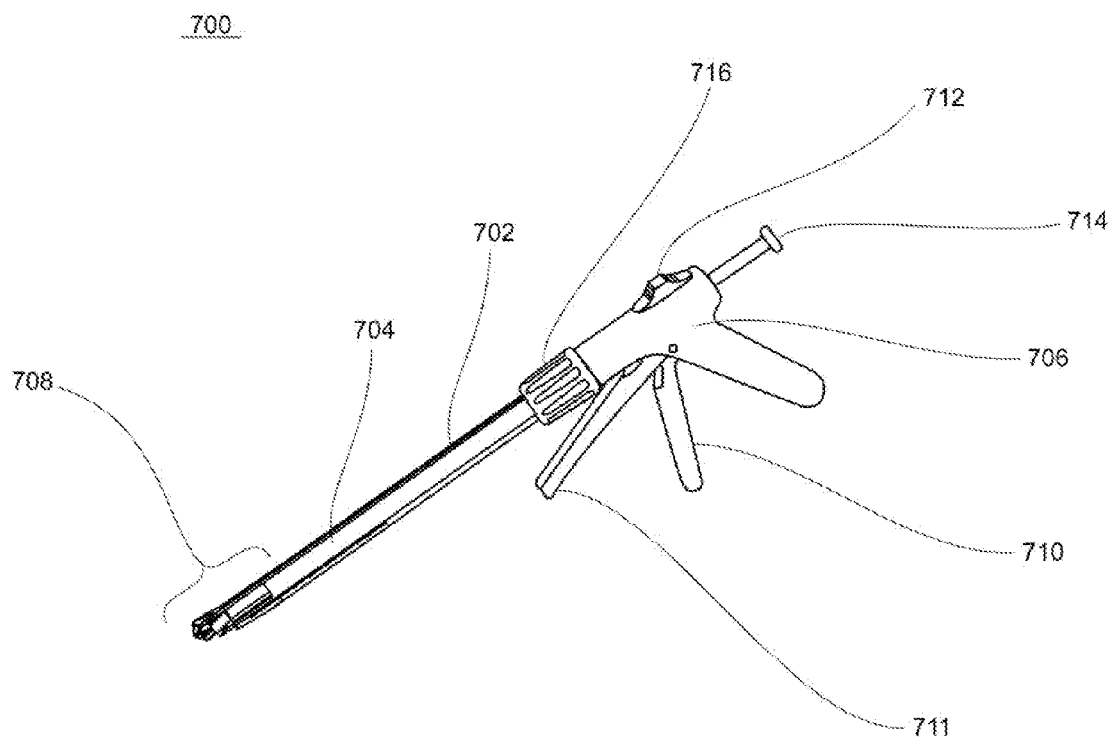

FIGS. 7A-7H illustrates such an integrated device and its operation, according to one embodiment of the present invention. Device 700 comprises an elongate tubular member 702 having internal working channel 704 and handle assembly 706 positioned at the proximal end. At the distal end of device 700 is multi-functional tool assembly 708, shown in the collapsed (i.e. pre-deployment or fully retracted) state in FIG. 7A. It is generally desirable that the outer diameter of elongate tubular member 702 be as small as possible, preferably 20 mm or less, more preferably 15 mm or less and, in some embodiments, 12 mm or less. The embodiment illustrated in FIG. 7A, illustrates actuating mechanisms used to operate the device, namely first trigger 710, second trigger 711, slider 712, and plunger 714 provided in connection with handle assembly 706. Also shown is rotating collar 716 that allows the orientation of handle assembly 706 to be independently adjusted by the user relative to the orientation of approximating tool assembly 708.

Figure 7B:
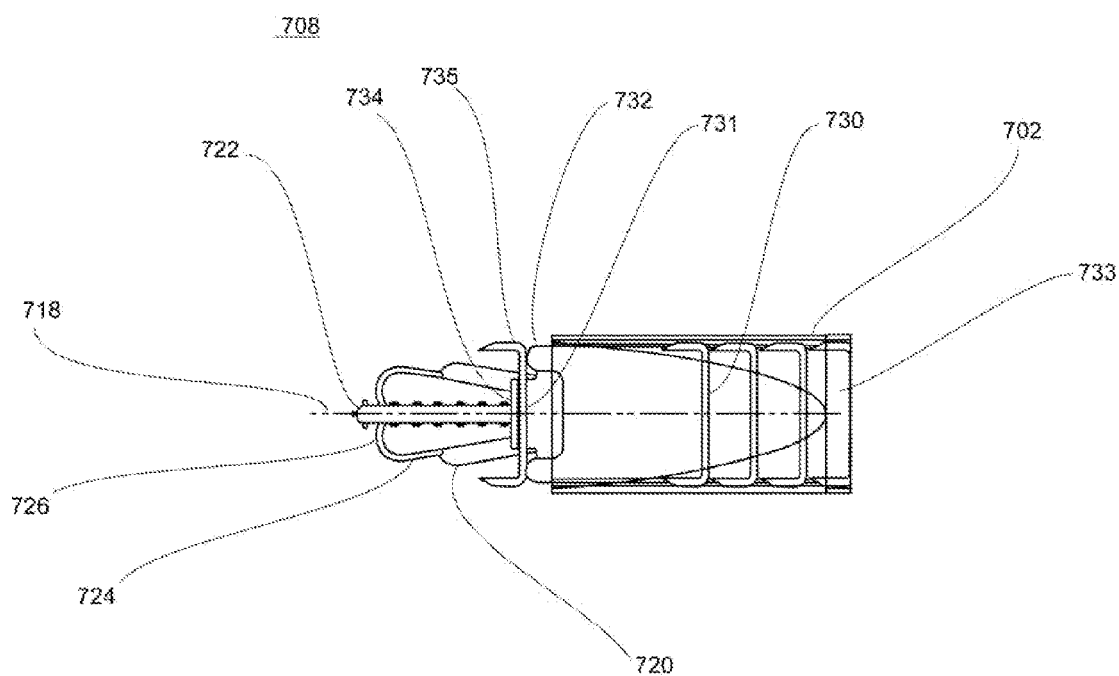

A close up cross sectional view of the distal end of device 700 is shown in FIG. 7B, illustrating details of multi-functional tool assembly 708 in the collapsed state. Multi-functional tool assembly 708 combines substantially similar structural and functional elements as previously illustrated in and described with reference to FIGS. 5 and 6. Accordingly, in this configuration, located along longitudinal axis 718 of working channel 704 are two (or more) extendible members 720, and (optional) pushing member 722, each being operatively connected to actuating mechanisms accessible to an operator at handle assembly 706. Each of the extendible members 720 is configured at its distal end with a distal tip 724, and each distal tip 724 incorporates one or more tissue engagement mechanisms whose working function is to controllably and selectively grasp, grab, grip, pierce, hold or otherwise engage tissue. In the example shown, distal tips 724 incorporate tissue hooks 726. Box-type staples in pre-deployed state 730 are loaded into working channel 704 and are configured (using, for example, guide channels and a spring loading mechanism) to slidably move toward the distal end of multi-functional tool assembly 708 and into the pre-fire position 731 as staples are sequentially ejected from the device. Pistons 732 are positioned at the distal end of shaft 733, and, along with stationary anvil 734, are used to deform staple legs 735 and thereby reconfigure and eject the staples when the device is actuated by the user, as described below.

Figure 7C:
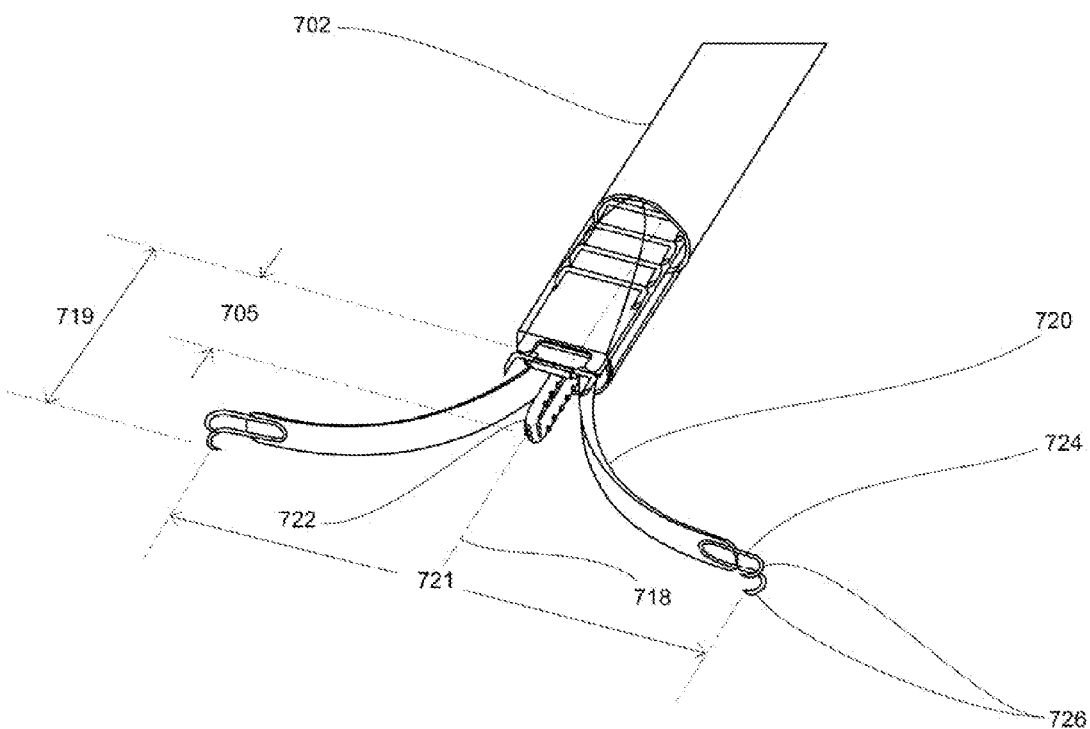
Figure 7D:
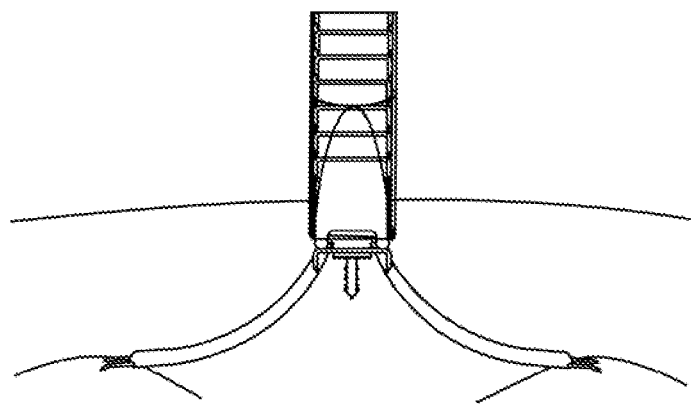
Figure 7E:
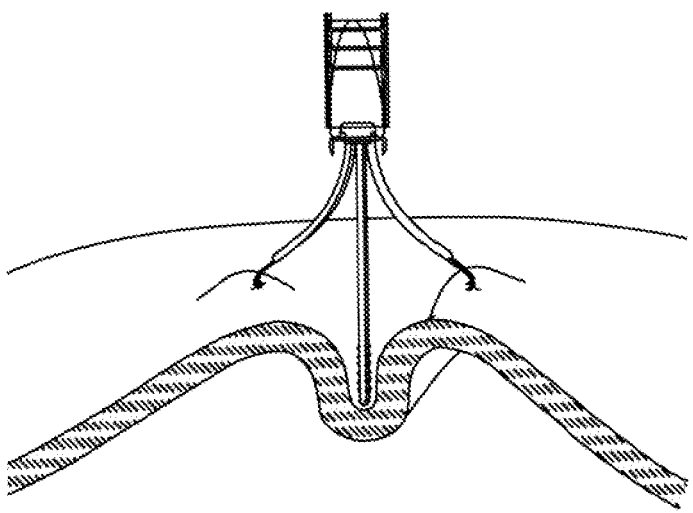
Figure 7F:
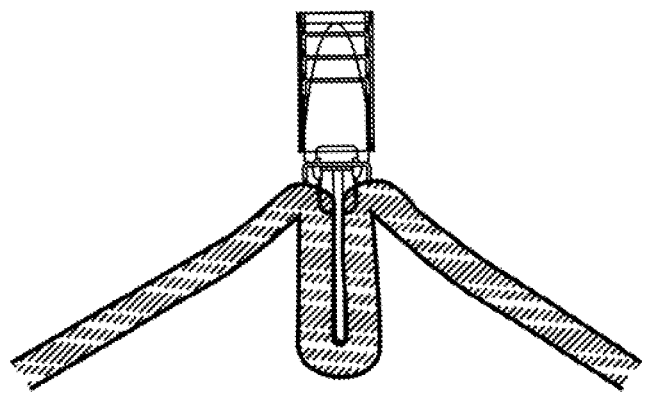

FIG. 7C illustrates a close up view of multi-functional tool assembly 708 having extendible members and tissue engagement mechanisms in the extended state, i.e. after being deployed by the operator. In the embodiment illustrated, plunger 714 is operatively connected to extendible members 720, such that when plunger 714 is pushed into handle assembly 706, extendible members 720 move distally along longitudinal axis 718 and thereby extend outwardly from working channel 704 and beyond the end of elongate tubular member 702. During deployment to the extended state, each of extendible members 720 is positioned such that distal tips 724 are spaced apart from one another and positioned on opposite sides of longitudinal axis 718. In the example shown, extendible members 720 have a flattened cross sectional configuration to increase lateral stiffness and prevent undesirable out-of-plane bending during deployment. Distal tips 724 of the extendible members 720 may comprise multiple tissue hooks 726, which facilitate secure tissue engagement and help to prevent undesired out-of-plane bending of extendible members 720 during deployment. Both the longitudinal positioning 719 and spacing 721 of arm tips 724 may be selectably controlled by the user to facilitate the desired positioning of tissue engagement members 726 and the subsequent size and position of the tissue plication formed by approximating the tissue.

Device 708 additionally incorporates pushing member 722, which is operatively connected to slider 712, such that when slider 712 is pushed from its proximal (fully retracted) position, the distal end of pushing member 720 moves along longitudinal axis 718, thereby extending out of working channel 704 a user selectable distance 705 beyond the end of elongate tubular member 702. The pushing member facilitates invagination and folding of the tissue between the engaged portions and may, additionally, function to disrupt the serosal tissue surface, or facilitate application of a tissue bonding promoter, as described above. Operation of the pushing member may be independent of, or coordinated with, extension and retraction of the extendible members and tissue engagement mechanisms.

Figure 7G:
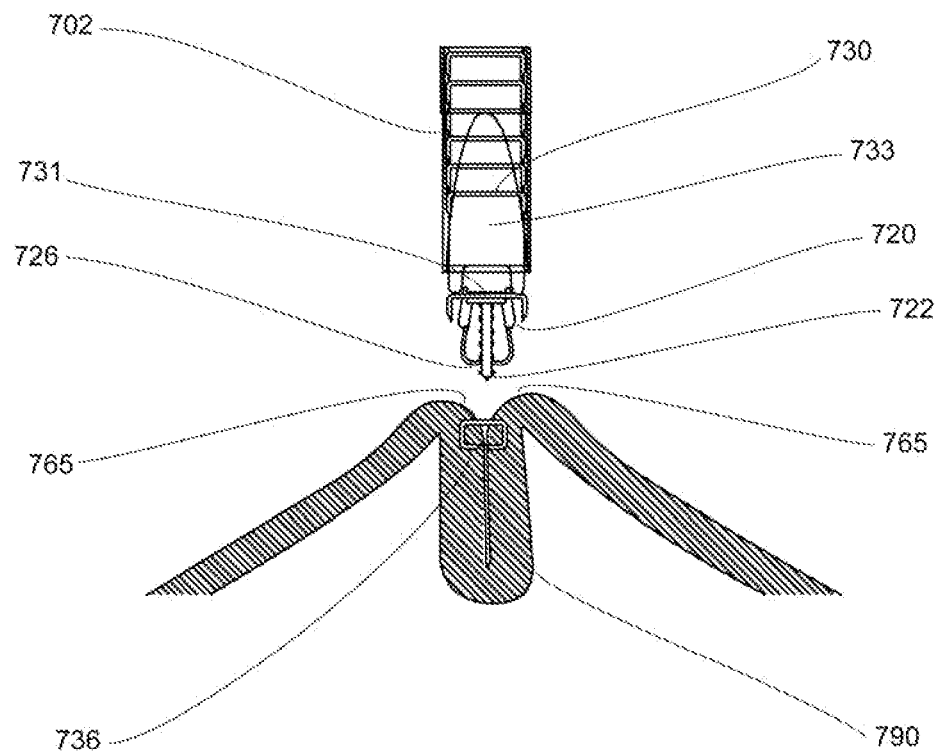

The steps of deploying device 700, engaging tissue, and invaginating and approximating tissue to create a tissue fold are substantially similar to what was previously described with reference to FIGS. 5D-5F. For the sake of clarity, these sequential steps are again illustrated in FIGS. 7D-7F with reference to operation of multi-functional tool assembly 708. After the tissue has been approximated and the fold has been created, device 700 is positioned in a suitable location for the subsequent step of applying one or more fasteners to secure the plication. Accordingly, similar to corresponding FIG. 6C, FIG. 7G illustrates the distal portion of device 700 after the device has been actuated from within handle assembly 706 using a second trigger 711, which is operatively connected to extendible shaft 733. The actuation, as described previously, forms and ejects a box-type staple, reconfiguring it by deformation from the pre-deployed state 730 to the deployed state 736, and securely implanting the staple within the tissue as described previously. This results in penetration and pulling together of the opposing tissue shoulders 765, which thereby secures the created tissue plication 790 projecting into the gastrointestinal space. Tissue hooks 726 may then be operatively disengaged from the tissue using a slight forward actuation of plunger 714 located within handle assembly 706, after which extendible members 720 may be completely retracted back into the shaft of the device by full reverse actuation of plunger 714. Pushing member 722 may also be completely retracted back into the device, using reverse actuation of slider 712. The serosal tissue layer may be treated to promote bonding during manipulation of the pushing member, as discussed previously. The next in line pre-loaded staple in the pre-deployed state 730 automatically (for example, via spring pressure) moves into the pre-fire position 731, and the device is therefore fully prepared and ready for repeating the entire sequence at the next tissue location selected by the operator, as shown in FIG. 7G.

Figure 7H:
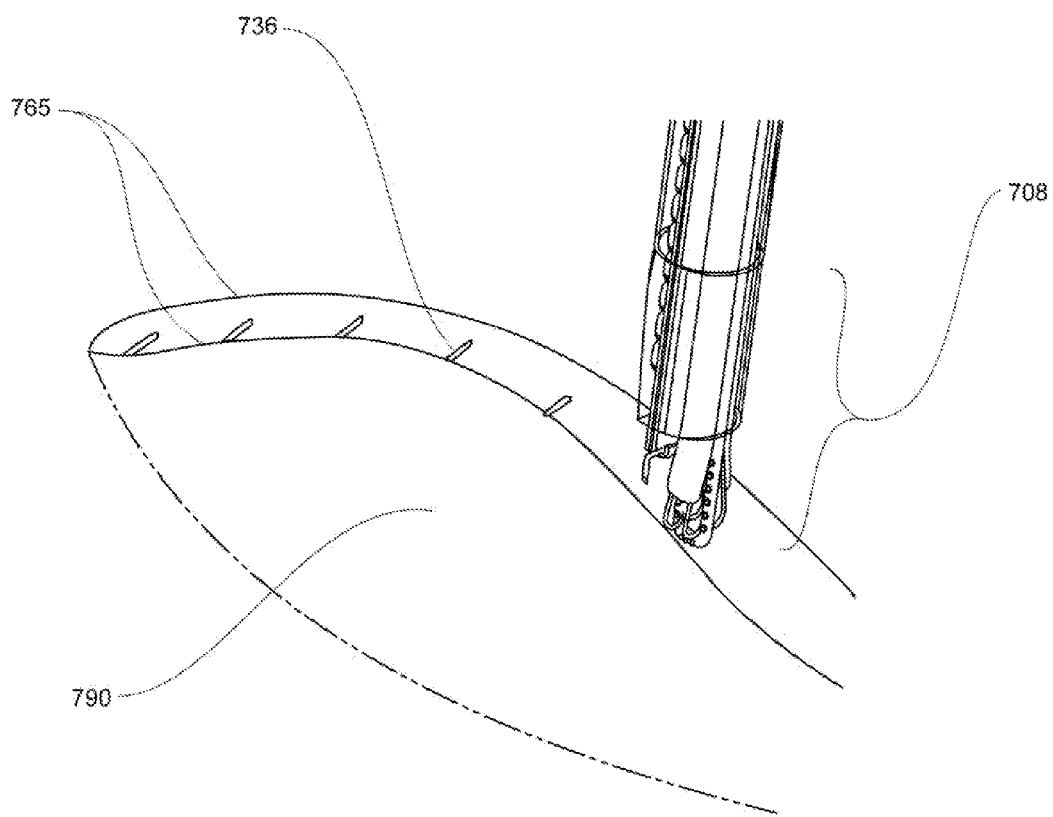

As illustrated in FIG. 7H (substantially similar to FIG. 6D), after repeating the procedural steps described above using multi-functional tool assembly 708, a plurality of staples in the deployed state 736 are implanted into and across tissue shoulders 765, securing plication 790 projecting into the gastrointestinal space. One or more such plications may be produced in this manner, each having the desired length, depth, etc., and each having a selectable number of implanted fasteners, fastener depth, fastener-to-fastener spacing, and so on, as previously described. Using the devices of the present invention in this manner, the operator is therefore able to achieve the desired gastric reduction laparoscopically and without ever needing to fully penetrate the gastric wall or otherwise compromise the internal mucosal tissue layer.

Figure 8A:
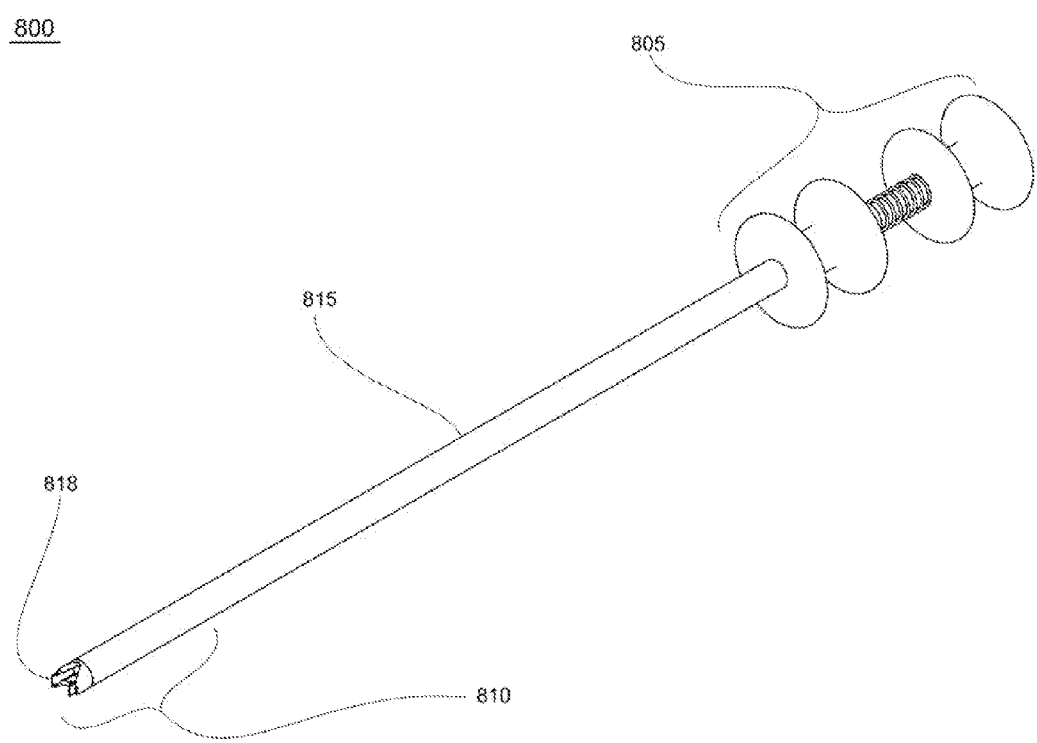
Figure 8B:
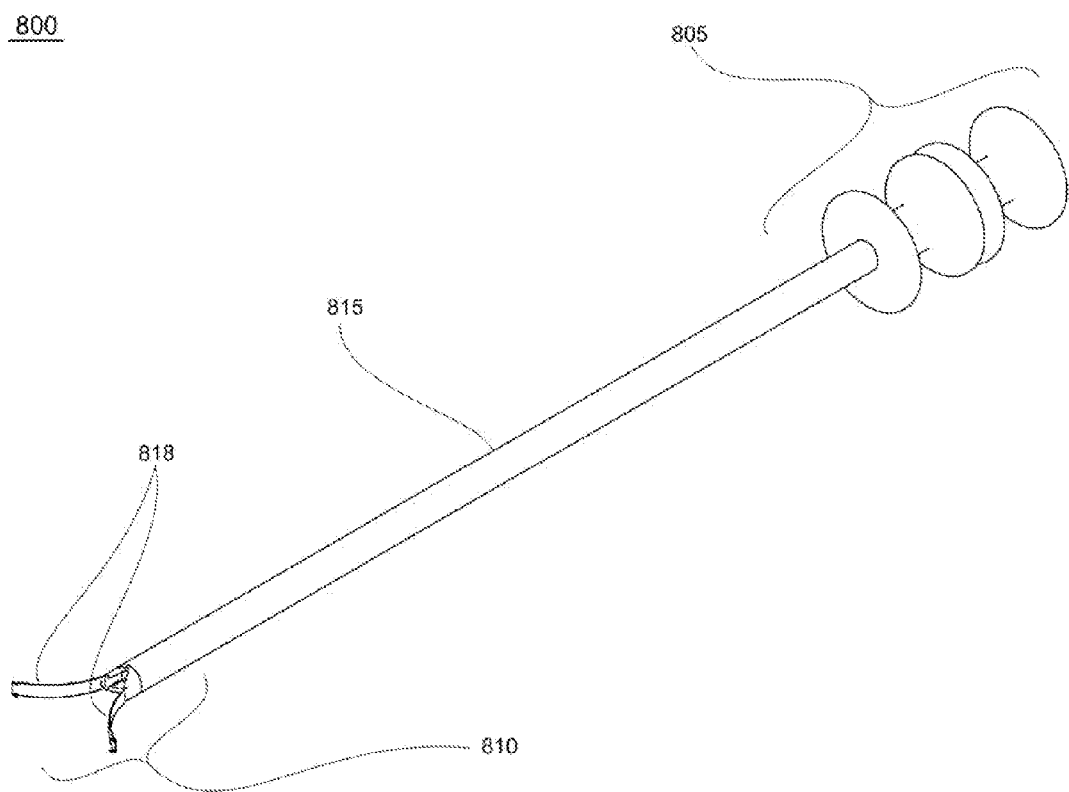

FIG. 8 illustrates an example device according to another embodiment of the present invention. An overview of device 800 is shown in FIG. 8A in the pre-deployed configuration, and in FIG. 8B device 800 is shown in the deployed configuration. Device 800 consists of handle assembly 805 positioned at the proximal end, tool assembly 810 positioned at the distal end, and elongate tubular shaft assembly 815 connecting handle assembly 805 and tool assembly 810. Handle assembly 805 is operatively connected to tool assembly 810 and provides for actuation of the device by the user, as will be described in detail below. In the example shown, tool assembly 810 includes two moveable arms 818 that are configured as longitudinal bands having rectangular cross section that are operatively connected to shaft assembly 815. As shown in FIG. 8A, in the pre-deployed (i.e. fully retracted) position, moveable arms 818 are held substantially within shaft assembly 815, with only the distal ends of moveable arms 818 visible and exposed at the distal end of device 800. As shown in FIG. 8B, in the deployed configuration handle assembly 805 has been actuated, as will be described below, and moveable arms 818 thereby extend out of and away from the distal end of shaft assembly 815, in the desired position for engaging tissue.

Figure 9A:
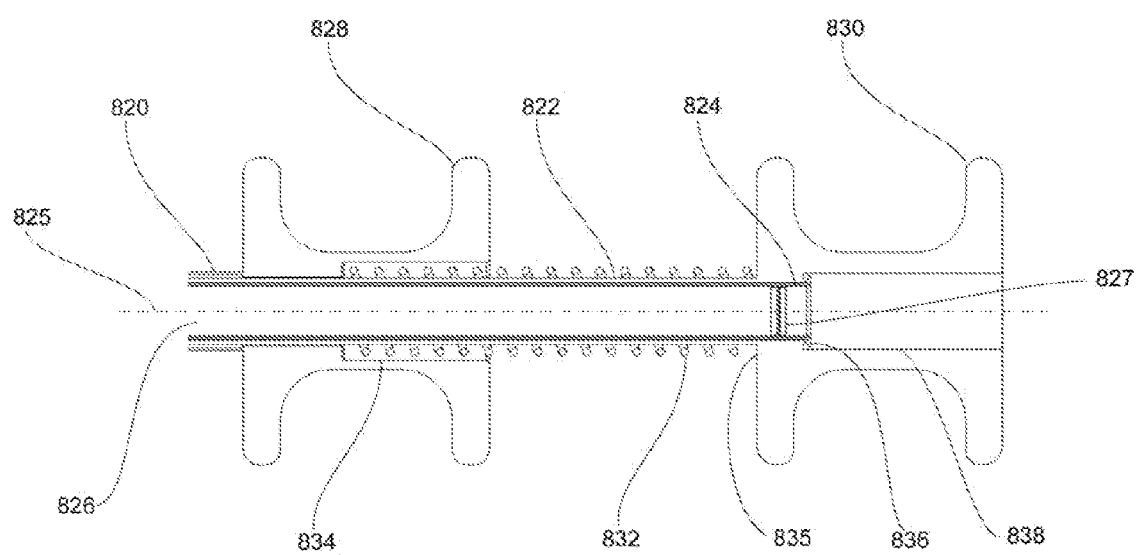

FIG. 9A shows a detailed cross section view of handle assembly 805, along with a portion of the proximal end of connected tube assembly 815. Tube assembly 815 consists of outer tube 820, actuating tube 822 and inner tube 824 which are co-axially arranged along longitudinal axis 825. In this embodiment, outer tube 820 is designed and configured to be inserted into a trocar placed through the abdominal wall when performing a laparoscopic procedure. It is therefore preferable that outer tube be as small in diameter as is practicable to allow for use of the smallest possible laparoscopic incision and trocar size. Outer tube 820 is preferably between 2 mm and 20 mm in diameter and between 5 cm and 100 cm in length, more preferably between 2.5 mm and 18 mm in diameter and between 12 cm and 70 cm in length, and most preferably between 3 mm and 12 mm in diameter and 15 cm and 65 cm in length.

Actuating tube 822 is inserted into the proximal end of outer tube 820 and terminates at its distal end at a location proximally from the distal end of outer tube 820. In this manner actuating tube 822 is capable of sliding longitudinally within outer tube 820 from its proximal most (i.e. pre-deployed) position to a distal most (i.e. deployed) position. The outer diameter of actuating tube 822 is slightly less than the inner diameter of outer tube 820 such that a small gap exists between the tubular walls. This substantially eliminates sliding friction between actuating tube 822 and outer tube 820, except at a small area of intimate frictional contact established between the tubes (described below). Inner tube 824 fits within actuating tube 822 and is also fixedly connected to outer tube 820 near the distal end of device 800, as described below. Located inside inner tube 824 is working channel 826 within which proximal gasket 827 is mounted. As will be described later, the purpose of proximal gasket 827 is to support and frictionally hold in position a complementary medical device that may optionally be inserted within working channel 826 of inner tube 824 during operation of device 800, as will be described later.

Tube assembly 815 therefore consists of a concentric tube configuration where actuating tube 522 is slidably positioned between the walls of outer tube 820 and inner tube 824, which are fixedly connected to one another at their distal ends. Outer tube 520, actuating tube 822 and inner tube 824 are all manufactured from suitable biocompatible materials, typically polymers and/or metals, that are known to those skilled in the art for common usage in either re-usable or single patient use medical devices. The tubes are typically substantially rigid, although they may be provided with a designed degree of elastic flexibility, or they may optionally incorporate articulation means (e.g. using mechanical methods well known in the art) along their length, which can prove useful in certain surgical situations.

Fixedly connected to the proximal end of outer tube 820 is distal grip 828, and fixedly connected to the proximal end of actuating tube 822 is proximal grip 830. When proximal grip 830 is moved toward distal grip 828 by the operator, actuating tube 822 slides distally between the walls of outer tube 820 and inner tube 824. Likewise, when proximal grip 830 is moved away from distal grip 828, actuating tube 822 slides proximally between the walls of outer tube 820 and inner tube 824. Distal grip 828 and proximal grip 830 can have the same or different shape, and are designed based on ergonomic considerations to allow easy gripping and secure holding by the hand of the operator, typically with the forefingers positioned on distal grip 828 and thumb positioned on proximal grip 830.

It should be recognized by those skilled in the art that various other types of grips may be used according to the present invention to allow the operator to affect the same type of relative sliding motion between actuating tube 822 and outer tube 820. For example, knobs, rings, grooves, levers, handles, and the like may be used. Distal grip 828 and proximal grip 830 may be produced from any polymeric or metallic material commonly known in the art for usage in either re-usable or single patient use medical devices. In other embodiments that will be obvious to those skilled in the art (not shown), one or both grips may be replaced by other means for engaging outer tube 820 and actuating tube 822, wherein said engagement means may be operatively connected to an alternative actuation mechanism (e.g. trigger, lever, pivotable handle, scissors grip, or the like) that may optionally be positioned farther away from the proximal end of tube assembly 815. In this manner, when said alternative actuation mechanism is operated by the user, substantially the same type of longitudinal sliding motion between actuation tube 822 and outer tube 820 is effected. Said alternative actuation mechanisms may be operated by user hand power, or they may be powered partially or entirely using an external power source such as an AC or DC electromagnetic motor, compressed gas, ultrasonic motor, or the like.

Located between distal grip 828 and proximal grip 830, and positioned outside actuating tube 822 is spring 832. Spring 832 is held in place by, and pushes against, distal grip 828 at recess 834, and also pushes in the opposite direction against the distal most surface 835 of proximal grip 830. Spring 832 is designed to operatively maintain a specified biasing force along longitudinal axis 825 that acts to push actuating tube 822 toward its proximal most position relative to the position of outer tube 820 when the device is in the pre-deployed configuration. When spring 832 is in its maximum allowable expanded state (i.e. device 800 is in the pre-deployed configuration), flange 836 located at the proximal end of deployment tube 824 comes into contact with the bottom of recess 838 located on the proximal side of proximal grip 830, thereby limiting the extent of proximal motion of actuating tube 822.

Figure 9B:
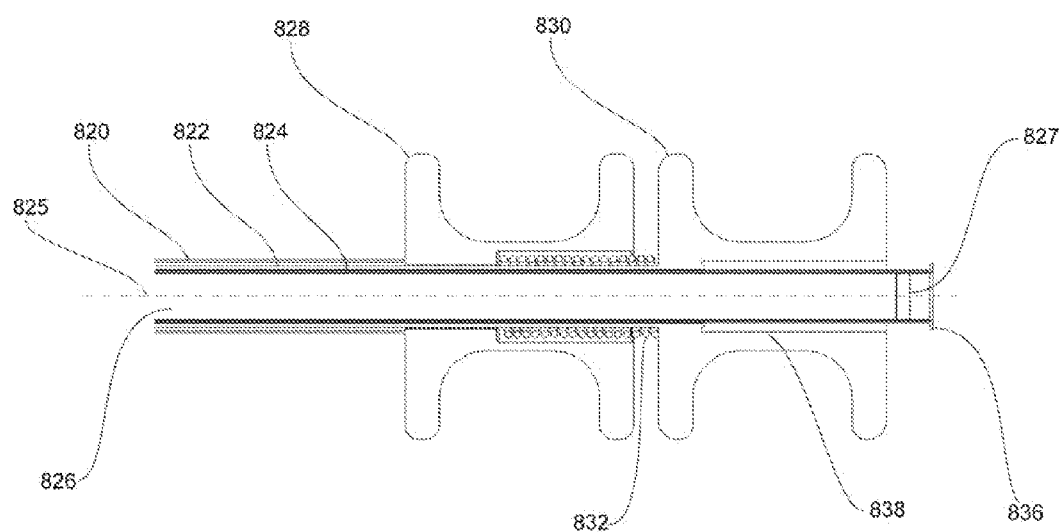

FIG. 9B illustrates a the detailed cross section view of handle assembly 805 after actuation as described. Movement of proximal grip 830 toward distal grip 828 thereby compresses spring 832 as actuating tube 822 slides distally between outer tube 820 and outside of inner tube 824. As shown, the proximal end of inner tube 824 then moves within recess 838 in proximal grip 830. As spring 832 is compressed, additional elastic energy is stored within the spring that is later released and used to return (or substantially assist in returning) proximal grip 830 to its proximal most (pre-deployed) position, thereby also tending to move actuating tube 822 back to its proximal most (pre-deployed) position (FIG. 9A).

Figure 10:
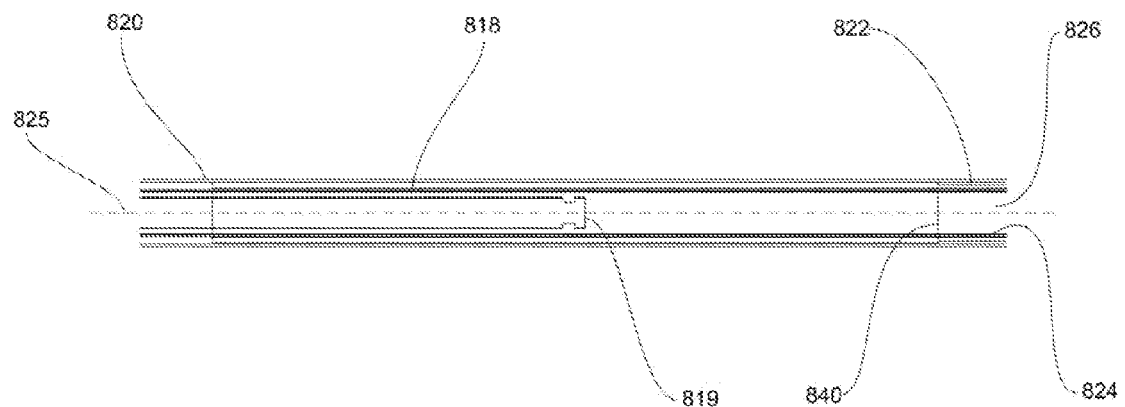
FIG. 10 shows a cross sectional view of a portion of a device for approximating tissue according to one embodiment of the present invention.

FIG. 10 shows a detailed cross section view of a portion of shaft assembly 815. Shaft assembly 815 consists of outer tube 820, actuating tube 822 and inner tube 824. As described previously, actuating tube 822 is slidably positioned between the walls of outer tube 820 and inner tube 824. Fixedly connected to the distal end of actuating tube 822 is bushing 840. The inside diameter of bushing 840 is the same as the inside diameter of actuating tube 822 such that inner tube 824 passes through without restriction. At least a portion of bushing 840 has an outside diameter that is sized to substantially make frictional sliding contact with the inner wall of outer tube 820. Bushing 840 thereby ensures that actuating tube 822 remains centrally aligned along longitudinal axis 825 during actuated sliding, while minimizing frictional forces and therefore minimizing the overall forces required for actuating device 800. Bushing 840 is further configured with engagement means for fixedly connecting to the proximal ends 819 of each of two moveable arms 818, such that moveable arms 818 are positioned between the walls of outer tube 820 and inner tube 824. This allows moveable arms 818 to move distally and proximally inside outer tube 820 along with the actuated distal and proximal sliding of actuating tube 822. In the example shown, bushing 840 is produced from molded polymer, and moveable arms 818 are embedded directly into the wall of bushing 840 during manufacture, for example by insert injection molding. Alternatively, various other methods known to those skilled in the art may be employed to fixedly connect the proximal ends of moveable arms 818 to bushing 840, such as keyed recesses, threads, rivets, welds, adhesives, and the like. Bushing 840 is also optionally configured with a means for guiding and maintaining a specified fixed rotational alignment between actuating tube 822 and outer tube 820 during sliding. For example, bushing 840 may be configured with a protruding tab (not shown) on its outer surface that is designed to fit within a longitudinal groove (not shown) located on the inside wall of outer tube 820. This allows longitudinal sliding of actuating tube 822, while preventing undesirable rotational motion relative to outer tube 820 that can damage moveable arms 818 or otherwise make actuation of device 800 difficult.

Figure 11A:
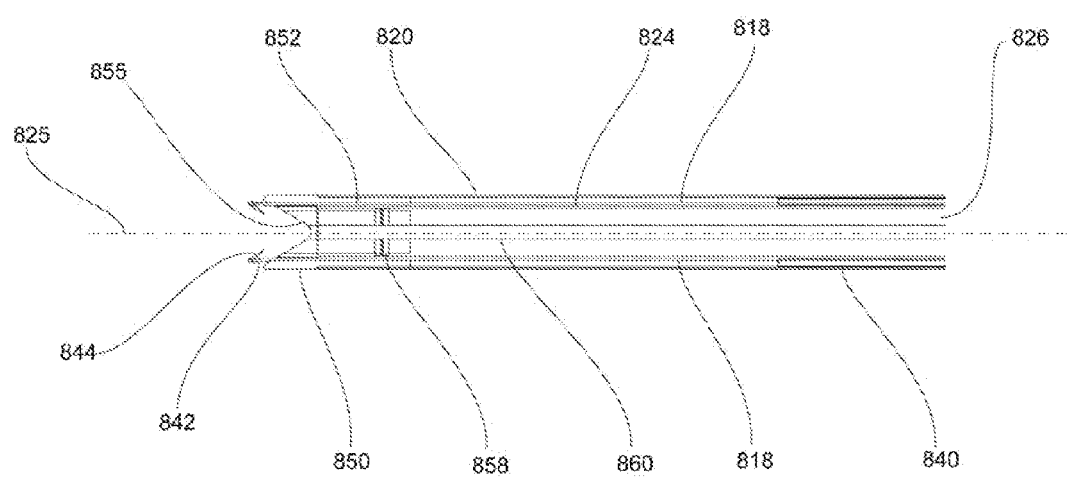

FIG. 11 shows a close up section view of tool assembly 810 located at the distal end of device 800. FIG. 11A illustrates the pre-deployed configuration. As described previously, moveable arms 818 are fixedly attached to the distal end of actuating tube 822 via bushing 840 and are thereby configured to move longitudinally in a forward (distal) or reverse (proximal) direction, corresponding to the actuated motion of proximal grip 830 relative to distal grip 828.

Moveable arms 818 can be made from any substantially flexible material and can be produced having a wide variety of shapes. Preferably moveable arms 818 have a non-circular cross section in order to minimize space requirements in the pre-deployment configuration, while also providing sufficient lateral rigidity (i.e. significant resistance to undesirable out of plane bending and rotation when in the deployed configuration). In device 800, moveable arms 818 have a rectangular cross section as shown, however it should be obvious to those skilled in the art that other cross sectional shapes can be used to provide the same functionality, for example, square cross sections, triangular cross sections, arcuate cross sections, hemispherical cross sections, and combinations of the foregoing may be used. The cross sectional shape, physical dimensions, mechanical properties, and so on, of moveable arms 818 may also be designed having variations along their length in order to provide improved deployment, tissue engagement or retraction characteristics.

Each of said moveable arms 818 is configured at its distal end with arm tip 842, wherein each said arm tip 842 includes one or more elements whose working function is to controllably and selectively grasp, grab, grip, pierce, hold or otherwise engage tissue. In the example shown, arm tips 842 incorporate sharpened tissue hooks 844. A variety of other configurations and mechanisms are possible within the scope of the present invention for engaging tissue at the distal end of moveable arms 818. For example, teeth, barbs, jaws, graspers, forceps, clamps and the like may be used, the choice of which may depend upon the nature of the tissue to be engaged, desired depth of penetration, and so on. In the pre-deployed configuration (FIG. 11A) moveable arms 818 are drawn up inside shaft assembly 815, slidably positioned in the gap between the outer wall of inner tube 824 and the inner wall of outer tube 820. Arm tips 842 are positioned adjacent to one another substantially close to the distal end of device 800.

Inner tube 824 has working channel 826 therewithin that provides a means for inserting and holding in position a variety of interchangeable and complementary tools (e.g. a device for manipulating or treating tissue, a device for applying fasteners, etc.) that, along with device 800, further comprise the systems of the present invention. Working channel 826 is designed to accept any instrument having a diameter that is smaller and within a specified size range. In the embodiment shown, for example, working channel 826 is designed to accept an instrument have a diameter from approximately 3.5 mm to 5.5 mm. Located inside working channel 826 are one or more retaining means capable of holding the inserted instrument in a desired longitudinal position, preferably allowing said position to be adjusted by the user prior to or during use. In the example shown, the retaining means is provided as an proximal gasket 827 (FIG. 9A) and distal gasket 858 (FIG. 11A) situated and held within retaining grooves (not shown) positioned along the inside wall of inner tube 824. Proximal gasket 827 and distal gasket 858 frictionally engage with the outer diameter of the inserted instrument to hold it in position. A specified amount of force may be applied that is sufficient to overcome the friction, and in this manner the position of the inserted instrument may be slidably adjusted. Various other means known to those skilled in the art may be employed to achieve the same results, for example, compression fittings, cams, clamps, twist locks, and so on, may be used.

Also located inside working channel 826 are optional alignment means that may engage with optional alignment features provided on the outside of an inserted instrument, to ensure a desired alignment of the inserted instrument is maintained relative to the orientation of device 800. In the example shown, alignment groove 860 located within the inside wall of inner tube 824 is configured to slidably engage with a suitably designed male feature (e.g. a protruding tab, nipple, pin, or the like) that may optionally be included on the exterior of the shaft of the medical device to be inserted. This allows for keyed insertion and longitudinal sliding to take place, but prevents undesirable rotation of the inserted device inside working channel 826 once inserted. This system feature may be important in a variety of situations, for example, a fastener applicator inserted into working channel 826 may need to be aligned in a specific orientation relative to the position of moveable arms 818 in order to properly secure the created tissue fold and produce a plication, according to the methods of the present invention. When it is desirable for the surgeon to change the overall orientation of the instrument relative to the target tissue, tube assembly 815 may be configured to rotate to any user selectable orientation relative to handle assembly 805; in such a configuration, the inserted instrument rotates along with tube assembly 815 thereby maintaining proper functional alignment of the instruments regardless of the user's hand position.

At the distal end of device 800 is end cap 850 which matingly connects to the inner wall of outer tube 820 and the outer wall of inner tube 824, thereby serving to fixedly connect these components together. End cap 850 further incorporates means for supporting, guiding and maintaining proper alignment of moveable arms 818 during actuated sliding, corresponding to the desired alignment between actuating tube 822 and outer tube 820. In the example shown, end cap 850 is produced from molded polymeric material and includes longitudinal slots 852 substantially matching the rectangular cross section of moveable arms 818 and through which moveable arms 818 are inserted during assembly.

Fixedly or removeably connected to end cap 850 is optional tissue configuration element 855 that is intended to guide, position and shape tissue that is approximated during use of device 800 as moveable arms 818 are retracted and the engaged tissue is drawn close to the distal end of tube assembly 815. In its simplest form, optional tissue configuration element 855 is provided as a pair of arms extending distally from end cap 850, defining a U-shape or V-shape (the example provided in FIG. 11B) into which tissue is drawn when moveable arms 818 are fully retracted after engaging tissue. Alternatively, cylindrical-shaped members, cone-shaped members, or the like, can be provided, as long as tissue can be drawn up against or inside the component upon retraction of moveable arms 818. Optional tissue configuration element 855 is beneficial for ensuring that the approximated tissue is provided in optimal configuration for the insertion of a retaining fastener that is used to secure a created tissue fold to produce a plication, according to the methods of the present invention. For example, optional tissue configuration element 855 may help ensure that tissue planes on both sides of the approximated tissue interface are automatically aligned substantially parallel to, and centered around, longitudinal axis 825 of device 800. Further, optional tissue configuration element 855 may be designed such that tissue drawn or pushed inside is thereby compressed a specified and desired amount, preferably in a direction perpendicular to the approximated tissue interface. Such tissue alignment and compression prior to fastening may improve the accuracy of fastener placement, may enhance the strength and durability of the plication produced, and may allow a simpler fastener design and smaller fastener applicator to be used compared to the prior art, as will be described below. A variety of interchangeable optional tissue configuration element designs may be useful in different circumstances, or sometimes it may be desirable to remove it altogether, therefore it is preferable that optional tissue configuration element 855 be removably connected to the distal end of cap 850 using a thread connection, snap connection, bayonet connection, or the like.

Figure 11B:
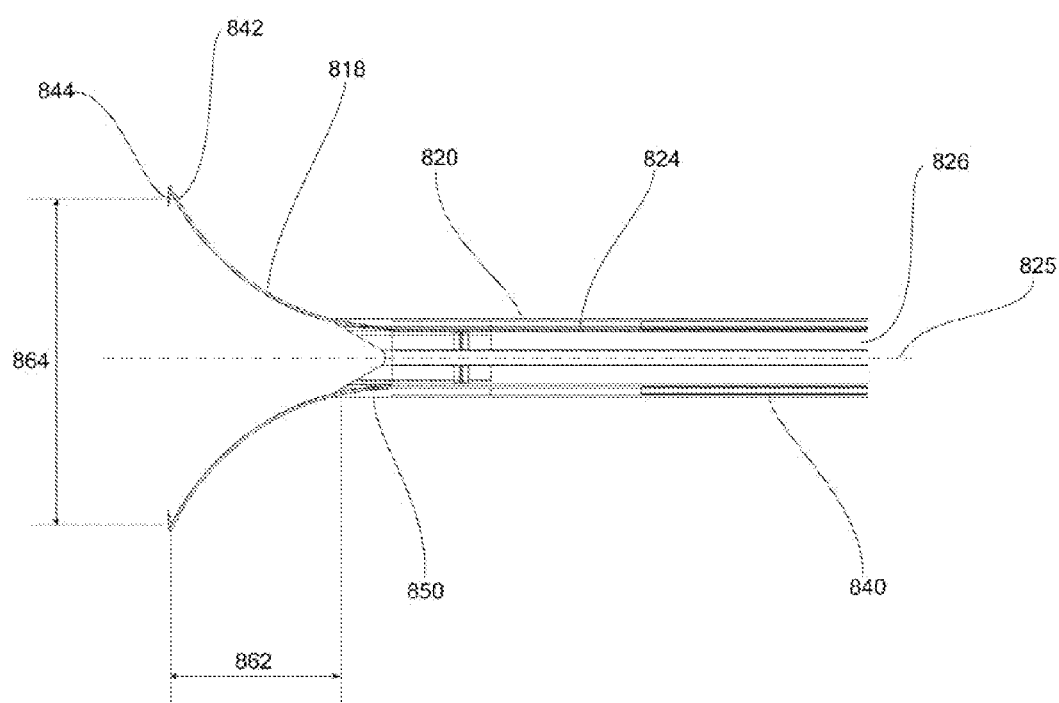

As described previously, device 800 is actuated by moving proximal grip 830 toward distal grip 828, thereby compressing spring 832. This causes actuating tube 822 to slide distally between outer tube 820 and inner tube 824, and moveable arms 818 thereby extend beyond the distal end of tube assembly 815, as shown in FIG. 11B. Device 800 may be held in the deployed configuration manually (using hand force supplied by the user) or, alternatively, a latch, cam, compression fitting, twist lock or other mechanical means known to those skilled in the art may be provided to temporarily maintain the deployed configuration after the user's hands are removed.

In the deployed configuration, each of moveable arms 818 are reconfigured such that arm tips 842 are separately spaced and positioned on opposite sides of longitudinal axis 825. Both the longitudinal positioning 862 and spacing 864 of arm tips 842 are selectably controlled by the user to facilitate the desired subsequent tissue engagement, up to the limit of full deployment when proximal grip 830 has been pushed together against distal grip 828 to compress spring 832 to the maximum allowable amount. Devices of the present invention may be designed to approximate tissue over a variety of size ranges, where longitudinal positioning 862 and spacing 864 are primary design factors that can be adjusted based on the intended medical mission. For use according to the methods of the present invention, it has been found that longitudinal positioning 862 is preferably between 0.5 cm and 20 cm, more preferably between 1 cm and 15 cm, and most preferably between 2 cm and 12 cm. Similarly, spacing 864 is preferably between 1 cm and 30 cm, more preferably between 1.5 cm and 20 cm, and most preferably between 2 cm and 15 cm.

During deployment of device 800, moveable arms 818 are designed to be reconfigured from a collapsed state to an expanded state to prepare the device for subsequent tissue engagement steps. In one preferred embodiment, moveable arms 818 are designed to be reconfigured from the collapsed state to the expanded state in a self-actuating manner, automatically achieving the desired tissue engagement configuration when extended out of tube assembly 815. Such self-actuating motions can be achieved by various methods known in the art. For example, in one preferred embodiment of the present invention, moveable arms 818 are produced from a highly elastic material (e.g. spring steel, hardened stainless steel, superelastic NiTi alloy, superelastic polymer, or the like) and are formed during manufacturing into the desired final deployed shape by mechanical and/or thermomechanical processing means known in the art. Moveable arms 818 are then spring biased (i.e. mechanical potential energy is stored, similar to a pre-loaded spring) by elastically deforming and loading them into tube assembly 815 to thereby provide the device in its pre-deployed state. As moveable arms 818 are then pushed out of tube assembly 815 during deployment, the stored energy is released and moveable arms 818 automatically return to the pre-determined shape, being the shape of the deployed state (FIG. 1B) desired for subsequent tissue engagement when brought into contact with the tissue surface.

Figure 12A:
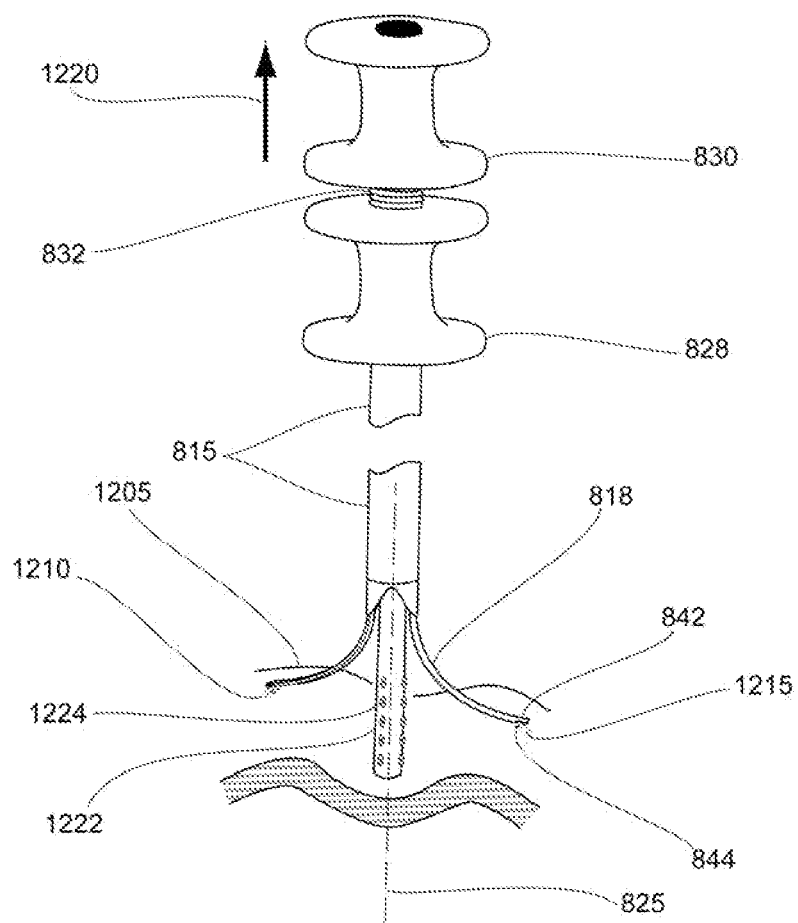

The operation of device 800 will now be explained in greater detail with reference to the steps used in performing the procedure of the present invention, illustrated in FIG. 12. FIG. 12A shows device 800 in the deployed configuration and positioned substantially perpendicular to the tissue surface 1205 to be approximated. Arm tips 842 are brought into contact with the tissue such that tissue hooks 844 are able to effectively penetrate the tissue surface and thereby engage the tissue at two separate locations 1210 and 1215. As illustrated, the locations of tissue engagement are determined by the shape and dimensions of moveable arms 818, arm tips 842 and tissue hooks 844 when in the deployed configuration, which substantially determines the size of the tissue fold that will be created upon approximation of the engaged tissue locations.

Figure 12B:
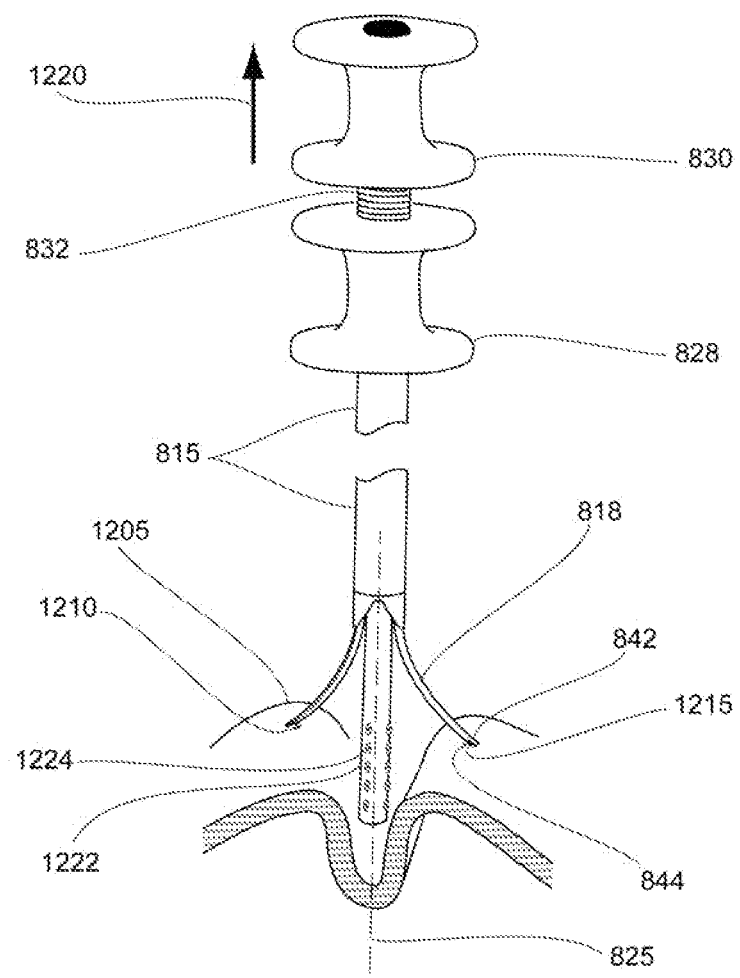

After tissue is engaged by tissue hooks 844 on arm tips 842, proximal grip 830 is subsequently released and the elastic energy stored in compressed spring 832 produces a longitudinal force 1220 that retracts actuating tube 822 and connected moveable arms 818 proximally toward the original (pre-deployed) configuration. Depending on the spring force available (which may be fixed by the design of device 800 and/or may be adjustable by the user) relative to the required forces for approximating the tissue, proximal grip 830 is moved proximally relative to distal grip 828 using an assisting hand force provided by the user, if desired or necessary. As retraction of moveable arms 818 back into tube assembly 815 begins, tissue engagement locations 1210 and 1215 are gradually pulled inward toward longitudinal axis 825, as illustrated in FIG. 12A. FIG. 12B shows the situation upon continued retraction of moveable arms 818, where proximal grip 830 is moved further proximally and tissue engagement locations 1210 and 1215 are positioned closer to longitudinal axis 825.

Also shown in FIG. 12A and FIG. 12B is the use of optional pushing member 1222, which is inserted into and extends distally from working channel 826 a user selectable distance, thereby controllably pushing against tissue between tissue engagement locations 1210 and 1215. Optional pushing member 1222 is held slidably within tube assembly 815 by proximal gasket 827 and distal gasket 858 (not shown) and therefore becomes a component of the system of the present invention that ensures the desired invaginated tissue fold is created during approximation, according to the methods of the present invention. Optional pushing member 1222 may further incorporate surface features 1224, whose function will be described below.

Figure 12C:
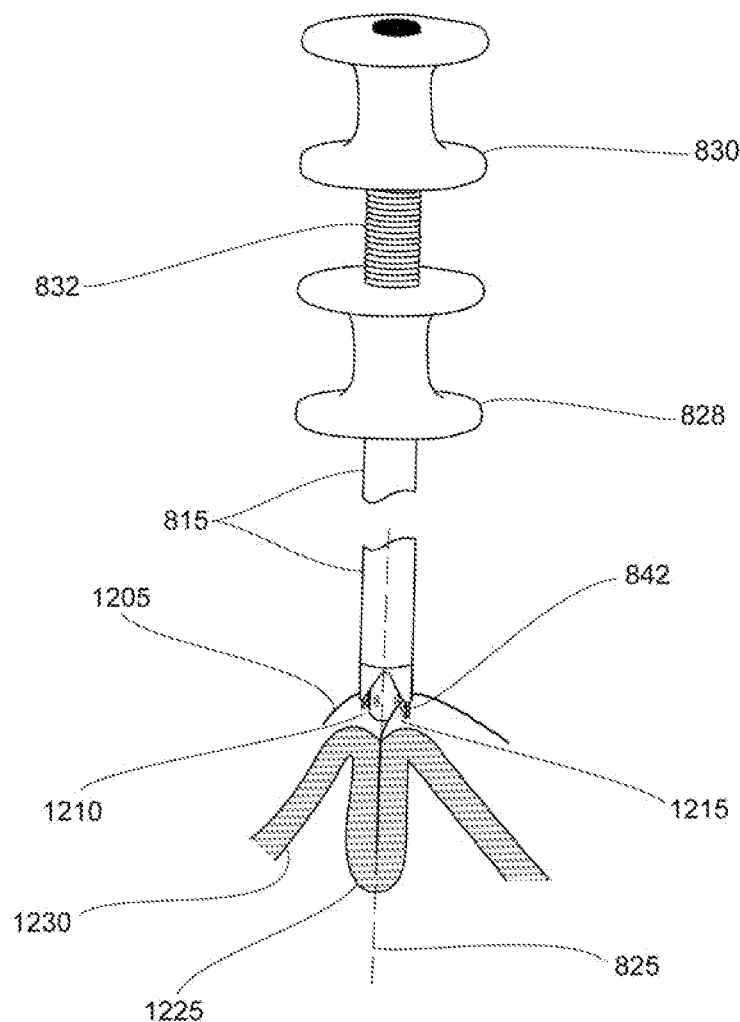

As illustrated in FIG. 12C, upon complete proximal movement of proximal grip 830 back to its pre-deployed position, moveable arms 818 are completely retracted within tube assembly 815 and only arm tips 842 are visible. Tissue engagement locations 1210 and 1215 are thereby approximated substantially near the distal end of tube assembly 815, creating an invaginated tissue fold 1225 extending distally away from the device substantially along longitudinal axis 825. Optional pushing member 1222 may either be left in place inside invaginated tissue fold 1225 until retraction is completed (as shown in FIG. 12C) or it may be withdrawn any time prior to completing creation of invaginated tissue fold 1225 by the user, if not further needed. As illustrated in FIG. 12C, in the case of approximating stomach tissue to create an invaginated tissue fold projecting into the gastrointestinal cavity according to the methods of the present invention, tissue surface 1205 comprises the external serosal tissue layer, and the opposing serosal tissue surfaces inside invaginated tissue fold 1225 are brought together and substantially intimate serosa-to-serosa contact is achieved, preferably without forming wrinkles, bunches, gaps, or the like, and without penetrating the internal mucosal tissue layer 1230.

According to one embodiment of the present invention, it is optionally desirable to selectively and therapeutically treat the serosal tissue layer to promote a healing response across the approximated serosal tissue surfaces within the produced plication. In one embodiment, the optional serosal treatment may be carried out before the tissue is approximated to form the tissue fold, as a separate tissue surface preparation step. For example, an independent surgical instrument designed for treating the serosa to promote a healing response may be introduced into the abdominal cavity through the same trocar used for device 800, or through a different trocar.

In another embodiment of the present invention the optional serosal treatment is carried out during creation of invaginated tissue fold 1225 by mechanically disturbing and disrupting the thin layer of mesothelial cells that form the outermost covering of the serosa. Since the layer of mesothelial cells covering the serosa is quite thin and fragile, it is easily disrupted, e.g. when an instrument is scraped, dragged or otherwise frictionally moved across the surface of the tissue. Consequently, the desired optional serosal treatment may be accomplished with the assistance of device 800 in various ways. For example, with device 800 in the pre-deployed configuration, the distal end of tube assembly 815 itself may be used to mechanically abrade the serosa. Alternatively, the distal tip and/or lateral surfaces of optional pushing member 1222 may similarly be used. To further aid in ensuring adequate serosal treatment occurs, optional pushing member 1222 may further be optionally configured with various means for treating the serosa. In one embodiment, as illustrated in FIG. 12, optional pushing member 1222 further incorporates surface features 1224 located on its distal end that are used to disturb and disrupt the serosal tissue surface. As will be obvious to those skilled in the art, a wide variety of such surface features and arrangements may be used to accomplish the desired serosal treatment, for example, ridges, bumps, bristles, teeth, scales, serrations, and the like may be provided. In one approach, serosal treatment may be accomplished prior to deploying device 800 to engage tissue by extending optional pushing member 1222 distally and moving it across substantially the identified area of serosal tissue to be included within the tissue fold in a sweeping or painting type of motion. Alternatively, because the lateral surfaces of optional pushing member 1222 will necessarily contact and slide across the opposing serosal tissue surfaces inside the tissue fold when optional pushing member 1222 is withdrawn after approximation is complete (see FIG. 12C), it can be used to disrupt at least a substantial portion of the serosal tissue surface during normal operation of device 800, thereby saving procedural time. In this case, surface features 1224 ensure more uniform and consistent serosal treatment, leading to a more effective healing response and a stronger serosa-to-serosa tissue bond.

According to the methods of the present invention, once the desired invaginated tissue fold projecting into the gastrointestinal cavity has been created as described above, securing means are then applied in order to produce a plication. While a variety of prior art fasteners and fastener applicators could conceivably be used for this purpose, various limitations and shortcomings have been encountered. In general, prior art surgical methods involving either cutting of the gastrointestinal lumen or the creation of gastrointestinal tissue folds rely upon the placement of surgical staples or other fasteners through the stomach wall. This necessarily involves the fastener penetrating at least the mucosal and muscularis tissue layers. Unfortunately, the mucosal and muscularis tissue layers are known to be relatively weak and unreliable for securely holding fasteners, and the placement of fasteners through these tissue layers often results in complications or lack of long-term durability. For example, prior art fasteners may produce chronic tissue irritation or result in tearing of tissue near the fastener penetration sites, may undergo post-surgical migration or dislodging, and may fail to heal and/or result in life threatening leakage at transgastric penetrations.

The tissue retaining fasteners of the present invention overcome the above stated problems. These fasteners are designed to be placed extragastrically into gastrointestinal tissue folds created using the tissue approximating devices of the present invention. In some embodiments placement of the tissue retaining fasteners may involve complete penetration through the stomach wall, whereas in other preferred embodiments the fasteners do not involve complete transgastric penetration. In either case, the tissue retaining fasteners of the present invention are preferably designed to engage and securely hold the thin, tough serosal layer covering the exterior of the gastrointestinal lumen. In this manner, these inventive tissue retaining fasteners thereby provide substantially improved strength, reliability and durability to the plication produced, while avoiding the serious risks associated with transecting the stomach wall, compressing the muscularis tissue layers, or excessively compromising the internal mucosal layer. According to the methods of the present invention, optional treatment of the serosal tissue to promote a healing response results in the formation of a strong serosa-to-serosa bond across the approximated tissue boundary within the plication, providing additional long-term structural support to the extragastrically placed fasteners. As such, the tissue retaining fasteners of the present invention may optionally be produced from a bioabsorbable or dissolvable material designed to disappear after the strong serosa-to-serosa bond has formed, further minimizing the risks associated with long-term fastener implants.

The tissue retaining fasteners of the present invention are designed to accurately penetrate, engage and securely hold invaginated tissue folds created by approximating devices of the present invention, thereby producing strong and durable plications. Minimally invasive fastener applicators of the present invention (described below) are provided that are designed to deliver and deploy these tissue retaining fasteners by operating in conjunction with the approximating devices of the present invention. The approximating devices, fasteners and fastener applicators of the present invention, taken together, comprise systems of the present invention.

Figure 13:
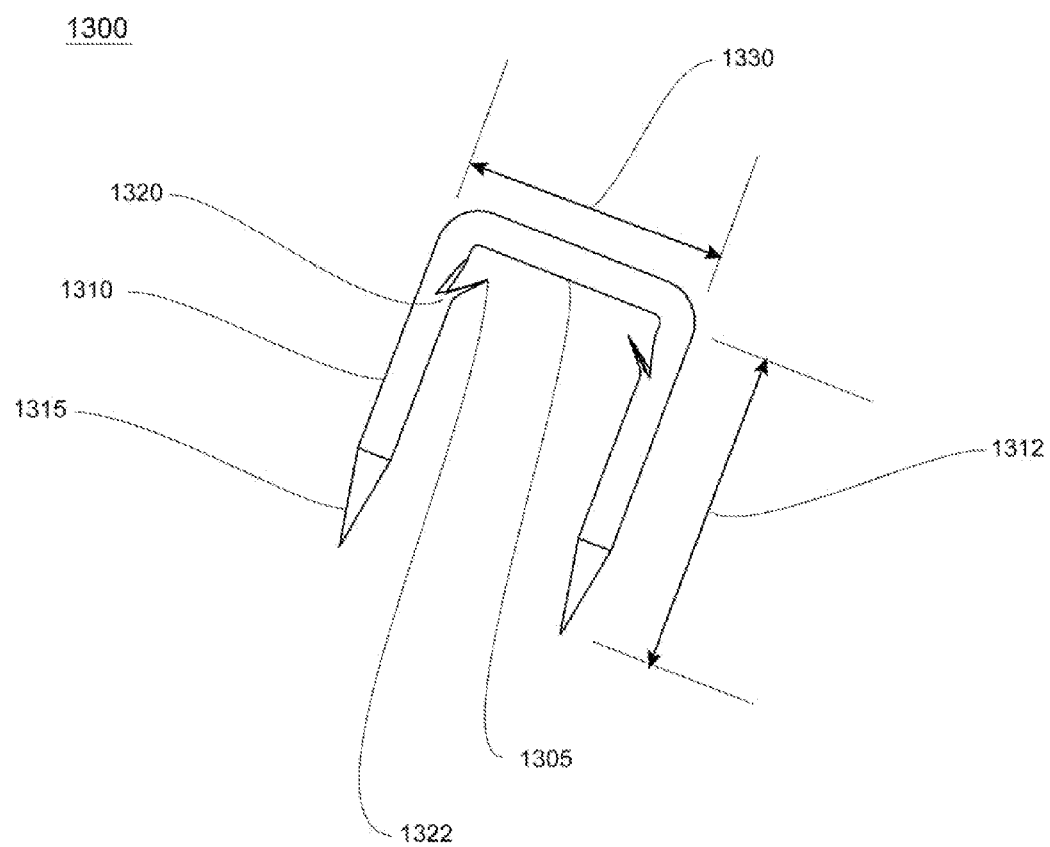
FIG. 13 illustrates a tissue fastener according to one embodiment of the present invention.

According to one embodiment of the present invention, a tissue retaining fastener is shown in FIG. 13. Fastener 1300 generally exhibits a u-shape having cross member 1305 and at least two substantially parallel tissue penetrating projections 1310 connected near opposite ends of said cross member and extending longitudinally therefrom. Tissue penetrating projections 1310 have length 1312. Each of said tissue penetrating projections has a sharpened tip 1315 positioned at its distal end that promotes penetration through the serosa and into the underlying muscularis tissue, lowering the required insertion forces. The fastener shown in FIG. 13 has a round cross section such as, for example, would be obtained by producing these fasteners from cut and bent wire or rod stock. In this embodiment, the diameter of the wire or rod used to manufacture the fastener is preferably between 0.05 mm and 2 mm, more preferably between 0.1 mm and 1.75 mm, and most preferably between 0.2 mm and 1.5 mm. In other embodiments different cross sectional shapes may be used, such as square cross sections, rectangular cross sections, semicircular cross sections, and so on. The fastener may be manufactured using any common production method and may be made from any suitable biocompatible material known to those skilled in the art of surgical staples and tacks, including, for example, metals such as stainless steel, titanium, and NiTi, or various structural polymers. The fasteners may also preferably be produced from bioabsorbable or dissolvable materials designed to have a limited functional lifetime after implantation in human tissue.

Positioned on at least one tissue contacting surface of each tissue penetrating projection 1310 is one or more tissue retention features, e.g. barb 1320 in FIG. 13. The tissue retention feature may be a point, barb, hook, tine, sharpened edge, or the like. It may be substantially rigid, substantially flexible, or combinations thereof. It may be formed as a part of the tissue penetrating projection during fastener manufacture, thereby having a fixed position, or alternatively it may be connected or joined to the tissue penetrating projection via a hinge, spring or other self-actuating feature that allows the tissue retention feature to change position from a collapsed configuration while in the fastener applicator to an expanded configuration (as shown in FIG. 13) prior to or during deployment into tissue. When deployed into tissue, the tissue retention feature is preferably angled at least partially in the proximal direction to allow fastener 1300 to readily slide forward into tissue during deployment, while preventing backward motion of the fastener out of the tissue after deployment. As shown in FIG. 13, barb 1320 is preferably located along tissue penetrating projection 1310 at a position substantially proximal from its distal end, and the proximal end 1322 of barb 1320 preferably terminates in substantially close proximity to the distal surface of cross member 1305. This design provides for the most rapid and effective engagement of the thin, tough serosal layer near the tissue surface after the fastener is fully inserted into tissue, where the serosal layer is effectively captured between barb 1320 and cross member 1305. The size, shape, sharpness, and so on, of the tissue retention features are important characteristics that can be optimized to improve the performance of the fastener. Barbs 1320 preferably extend inward (i.e. toward the approximated serosa-to-serosa interface within the invaginated tissue fold). This avoids the possibility that the barbs may inadvertently penetrate through the stomach wall or damage the mucosa, and any damage to the serosa caused by these barbs will occur within the resulting plication and therefore serve to promote a healing response and beneficial serosa-to-serosa bonding across the tissue fold.

Figure 14:
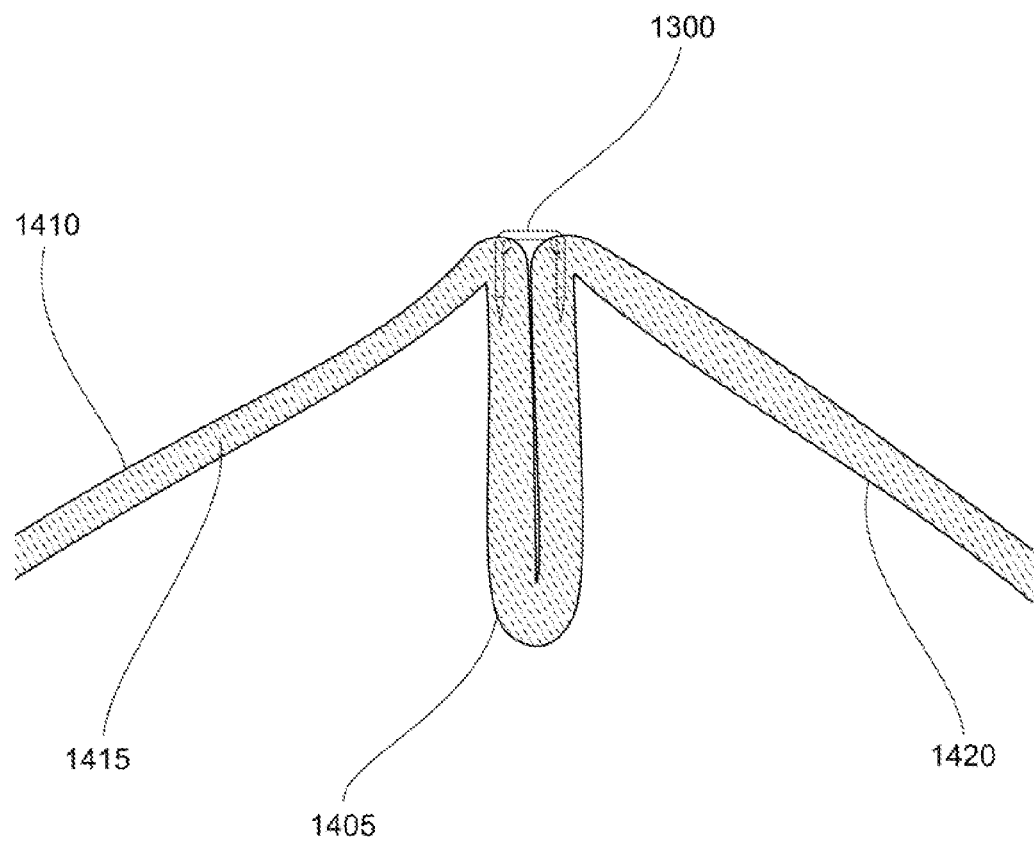
FIG. 14 illustrates placement of an extragastric tissue fastener to secure a tissue fold and produce a plication according to one embodiment of the present invention.

The width of fastener 1300 is established by the width 1330 of cross member 1305. It is desirable that width 1330 be as small as possible in order to minimize the size of the required fastener deployment device and to leave behind the minimum amount of material implanted within the body, while at the same time ensuring the fastener is able to span across the approximated tissue boundary within the created tissue fold to reliably penetrate and engage tissue on opposing sides of said tissue fold. As shown in FIG. 14, fastener 1300 secures plication 1405 projecting into the gastrointestinal space by penetrating through serosal layer 1410 and into muscularis layer 1415, without perforating mucosal layer 1420. Given the known thickness of human stomach tissue (typically 2-6 mm), an optimum width 1330 of cross member 1305 therefore a exists. Accordingly, cross member 1305 is preferably between 2.5 mm and 8 mm, more preferably between 3 mm and 6 mm, and most preferably between 3.5 mm and 5 mm. The length 1312 of tissue penetrating projections 1310 can be varied but it is generally preferred that length 1312 be less than 2× the width 1330 of cross member 1305.

Figure 15A:
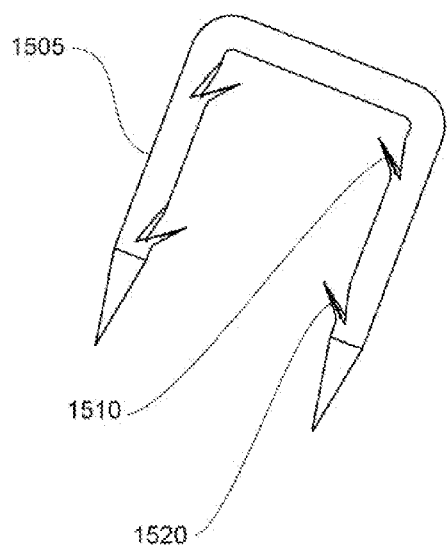
FIGS. 15A and 15B illustrate alternative embodiments for tissue fasteners of the present invention.
Figure 15B:
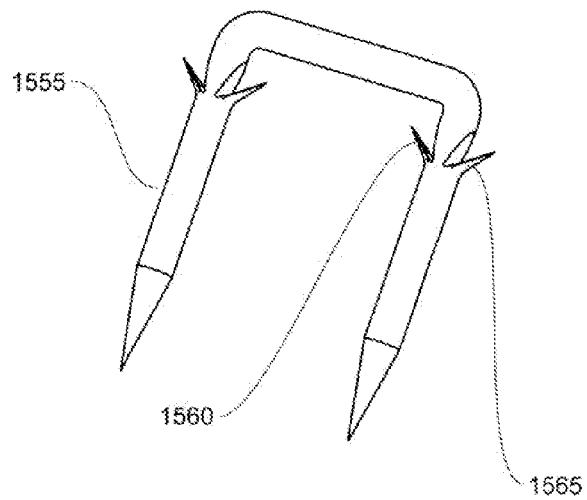

FIG. 15 illustrates some alternative embodiments of the tissue retaining fasteners of the present invention. FIG. 15A shows fastener 1500 being substantially similar to fastener 1300 (FIG. 13), however, there are two pairs of tissue retaining features positioned along tissue penetrating projections 1505. Proximal barbs 1510 provide for serosal engagement, similar to that described for barb 1320 of fastener 1300, while distal barbs 1520 serve to also engage the underlying muscularis tissue layer, thereby providing additional strength for holding the fastener securely within stomach tissue. FIG. 15B shows yet another embodiment, where fastener 1550 includes tissue retention features protruding in different directions from tissue penetrating projection 1555. Inward pointing barbs 1560 are substantially similar to barbs 1320 of fastener 1300. Additional outward pointing barbs 1565 provide for extra serosal engagement surface area and can therefore increase the holding power of the fastener. As will be obvious to those skilled in the art, various other tissue retention feature configurations are possible and considered within the scope of the present invention that help produce a more secure plication. For example, additional tissue retaining features may be added that are oriented 90 degrees from the inward pointing barbs in order to also engage tissue parallel to the approximated tissue interface within the tissue fold. Alternatively, tissue retaining features may be formed completely around the tissue contact surface of the tissue penetrating projections, providing for tissue engagement in all directions.

Figure 16A:
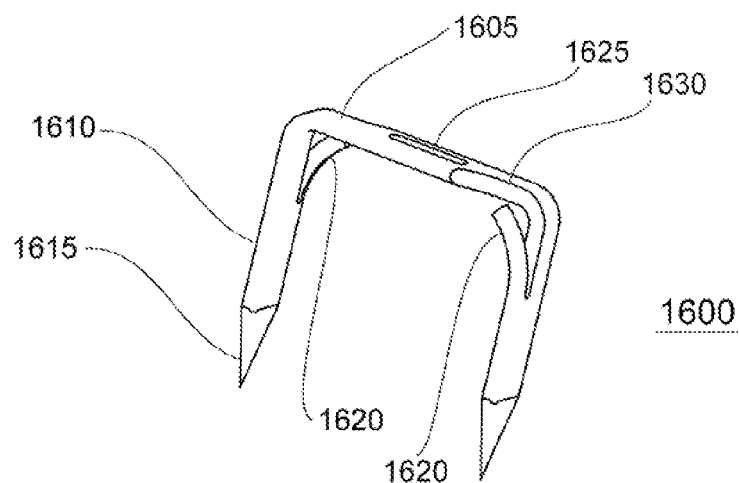
FIGS. 16A-16C illustrate alternative embodiments for tissue fasteners of the present invention.

FIG. 16 shows three different alternative embodiments of fasteners of the present invention. In these examples, the fasteners are mass manufactured easily and inexpensively from flat sheet biocompatible material, for example by stamping, cutting, etching, or the like, followed by bending to produce the u-shapes indicated. In FIG. 16A, fastener 1600 consists of cross member 1605 and penetrating projections 1610 having sharpened tips 1615. Each of said penetrating projections has at least one tissue retaining feature, in this case proximally positioned inward pointing barbs 1620. The proximal end of barbs 1620 in this example terminate substantially flush with the distal surface of cross member 1605. Cross member 1605 optionally has one or more holes cut through its thickness, such as hole 1625. Hole 1625 serves two functions. First, hole 1625 provides a means for engaging with a suitably designed fastener advancement and deployment mechanism incorporated within a compatible fastener applicator. Second, after the fastener is deployed and implanted into stomach tissue, with cross member 1605 being placed in intimate contact with the serosal tissue layer, hole 1625 promotes tissue ingrowth through and around the fastener after surgery, thereby increasing the retention force, holding power and long-term durability of the implanted fastener. Cutout 1630 is a portion of cross member 1605 having narrower cross sectional area that is positioned directly over the proximal end of barb 1620. This feature, combined with the proximal termination of barb 1620 being substantially flush with the distal surface of cross member 1605, provides a new and additional mechanism for securely engaging the thin layer of serosal tissue, as follows. When the fastener is implanted extragastrically in stomach tissue, the thin serosal tissue layer is effectively captured between barbs 1620 and cross member 1605. This serosal capturing feature prevents the serosa from disengaging from the barbs and thereby resists fastener dislodgement, even during the substantial and sometimes erratic stomach motions produced during eating and digestive processes.

Figure 16B:
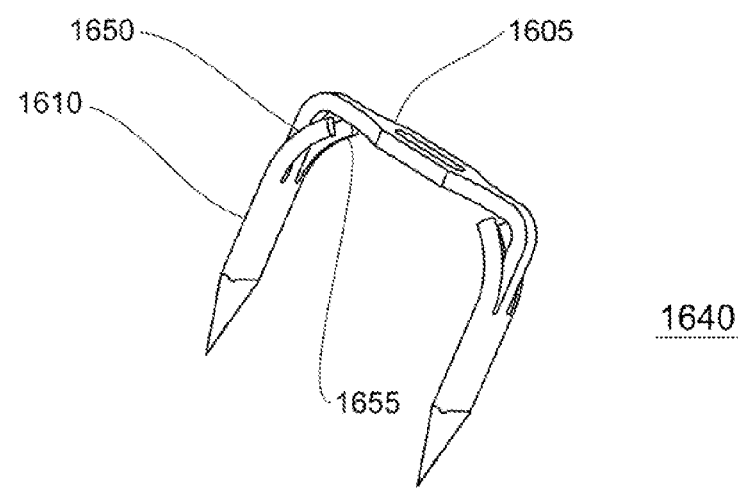
Figure 16C:
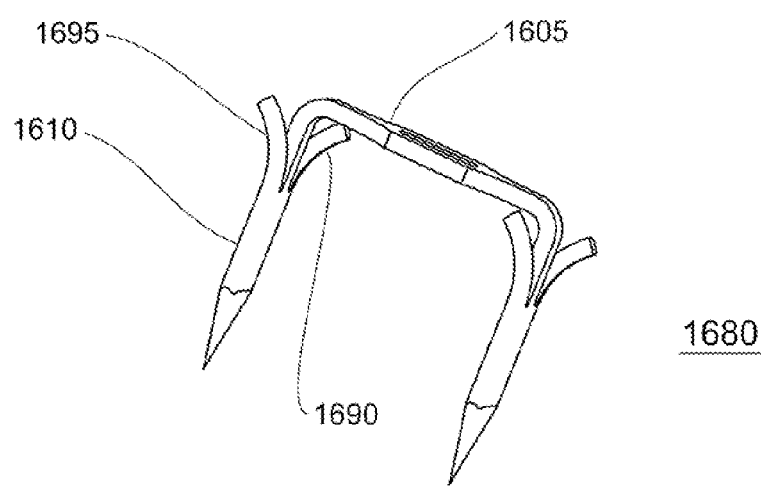

FIG. 16B shows another embodiment similar to FIG. 16A, however, in the example of fastener 1640, on each tissue penetrating projection 1610 there are two proximally positioned inward pointing barbs 1650 and 1655. This increases the strength and reliability of the tissue engagement by increasing the amount of serosal tissue captured during fastener placement. FIG. 16C shows yet another embodiment of a fastener similar to that of FIG. 16B, however in the example of fastener 1680, on each tissue penetrating projection 1610 there are proximally positioned barbs pointing both inward (toward) 1690 and outward (away from) 1695 the approximated serosa-to-serosa interface within the invaginated tissue fold.

Figure 17:
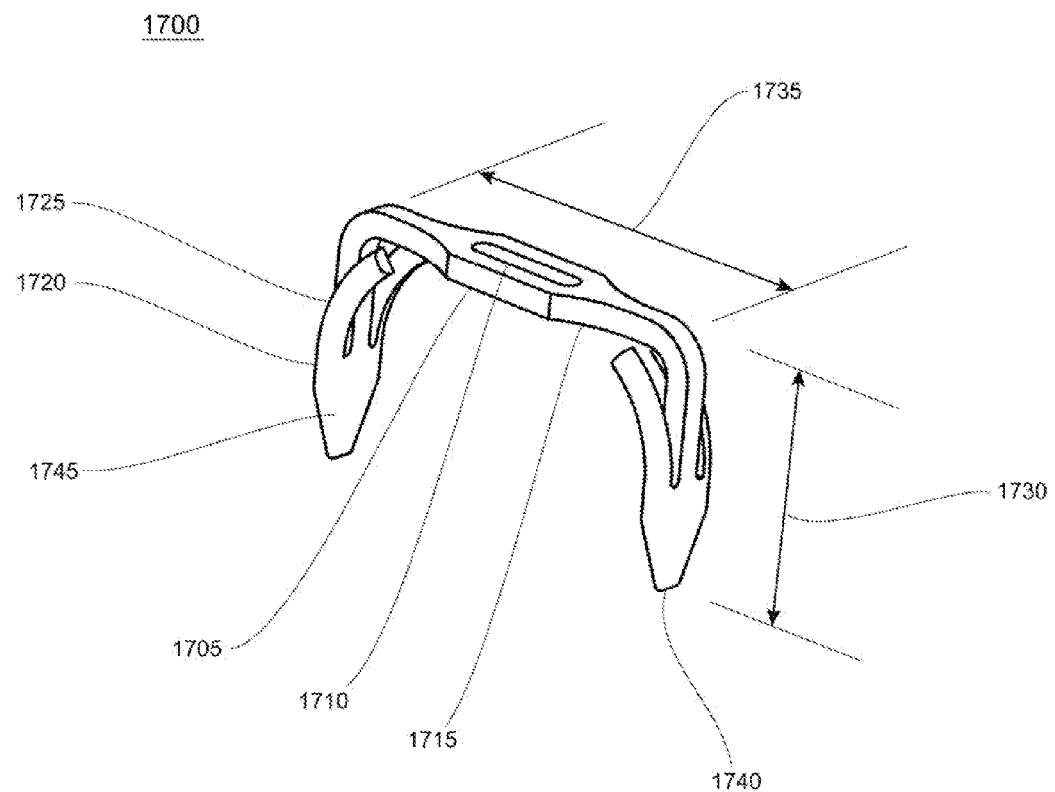
FIG. 17 illustrates an alternative embodiment for a tissue fastener of the present invention.

In contrast to prior art tissue fasteners, it has rather unexpectedly been found for the case of the extragastric tissue fasteners of the present invention that improved holding force and performance is achieved when the tissue penetrating projections are made as short as practicable. This is because it is most desirable to provide for complete penetration through the serosal layer and into the underlying muscularis layer, but otherwise not penetrate substantially deeper into the underlying muscularis tissue than necessary as this can reduce the retaining strength of the fastener, lead to inadvertent mucosal penetration, or result in undesirable tissue damage during or after surgery. FIG. 17 shows one embodiment of this type of fastener, which is similar to fastener 1640 of FIG. 16B. Fastener 1700 consists of cross member 1705 having hole 1710 and cutout 1715, whose functions were described previously. Each of tissue penetrating projections 1720 has two proximally positioned inward pointing barbs 1725. Because the serosal layer is so thin relative to the overall thickness of stomach tissue, in this embodiment the length 1730 of the tissue penetrating projections 1720 is preferably less than the twice the width 1735 of cross member 1705. The length 1730 of tissue penetrating projections 1720 is more preferably less than 1.5×, and most preferably less than 1× the width 1735 of cross member 1705.

Other novel embodiments of the fasteners of the present invention are also illustrated in FIG. 17. For example, note that the previously shown sharpened tips located at the distal ends of the tissue penetrating projections have been replaced with non-sharp tips 1740. While sharpened tips minimize the forces necessary to deploy a fastener into tissue, it is also possible that normal stomach movements produced by eating or digestion, or fastener migration after long periods of time, can cause these sharp tips to move within the tissue, thereby causing undesirable chronic irritation or damage. It is therefore often preferable to employ non-sharp tips 1740, which may be produced by dulling, smoothing, rounding or otherwise making the tips of the tissue penetrating projections sufficiently blunt that such tissue damage is not possible. Accordingly, it has been determined that the minimum radius of curvature on any tissue contacting surface of non-sharp tip 1740 of tissue penetrating projections 1710 is preferably greater than 0.01 mm, more preferably greater than 0.03 mm, and most preferably greater than 0.06 mm. The use of non-sharp tips 1740 on the tissue penetrating projections does undesirably require greater fastener deployment forces, which may be higher than forces typically available using prior art fastener applicators. It is therefore preferable to use the novel fastener applicators of the present invention (described below), which overcomes the problem of higher fastener insertion forces and therefore allows the clinical advantages of non-sharp tips 1740 to be realized while providing for easy and safe fastener deployment.

As illustrated in FIG. 17, it has also been found that the shape and edges of the transition region 1745 between non-sharp tip 1740 and the uniform cross section portion of tissue penetrating projections 1720 are very important for achieving maximum fastener retention and holding force. During fastener deployment, it is preferable that the tissue penetrating projections 1720 become completely embedded in tissue with the minimum amount of tissue cutting or tearing. It is therefore desirable that the shape of the transition region 1745 be designed to spread and stretch tissue during penetration, without significant cutting or tearing. This is most readily accomplished using smooth tapered, conical or similar geometric shapes that gradually increase the circumference of the cross section moving proximally from the distal tip, while avoiding the presence of any sharp edges that slide or cut tissue, i.e. the edges on any tissue contacting surface preferably have a minimum radius of curvature greater than about 0.01 mm, more preferably greater than 0.03 mm, and most preferably greater than 0.06 mm.

Figure 18A:
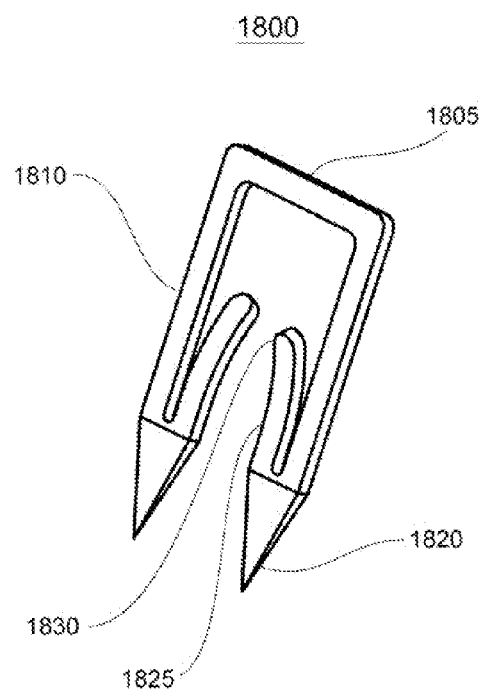
FIGS. 18A and 18B illustrate alternative embodiments for tissue fasteners of the present invention.
Figure 18B:
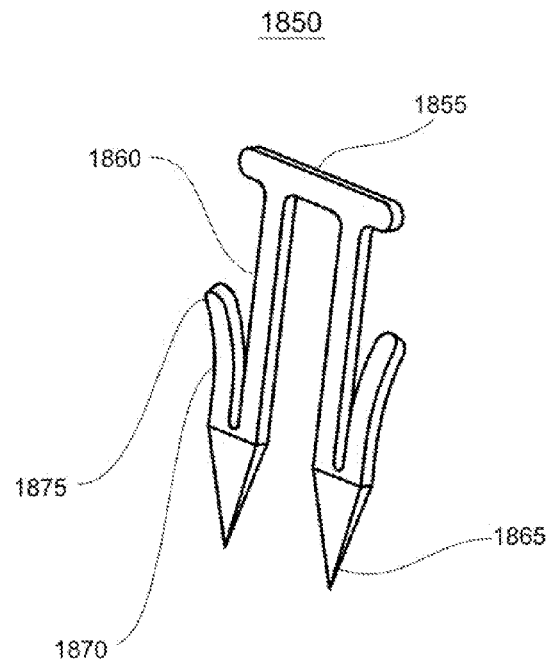

Yet other embodiments of fasteners of the present invention are shown in FIG. 18. These u-shape fasteners are also mass manufactured simply and inexpensively from biocompatible sheet material such as titanium, stainless steel, structural or absorbable polymers, and the like. In FIG. 18A, fastener 1800 consists of cross member 1805 and tissue penetrating projections 1810 having sharpened tips 1820. A unique embodiment of these fasteners is the tissue retaining features, arms 1825 in this example. Arms 1825 may be rigid and fixed in position (e.g. formed in the configuration shown by bending during fastener manufacturing) or they may be partially or substantially elastically deformable and flexible (e.g. they may be retained in the plane of the fastener while held within the fastener applicator and deployed into the configuration shown via a self-actuating spring-type of manner when deployed out of the fastener applicator into tissue. In either case, after extragastric insertion into stomach tissue, the proximal ends 1830 of arms 1825 therefore preferably engage serosal tissue in directions perpendicular to the plane of the fastener (i.e. pointing in a direction parallel to the approximated tissue interface), at locations away from the perforations made in the serosa by the penetrating tips 1820 during fastener insertion. This unique out-of-plane tissue engagement feature provides increased retention force and reduced chance the fastener will slip or tear out of the tissue as a result of tissue damage necessarily incurred during fastener insertion. FIG. 18B shows another similar embodiment, where fastener 1850 consists of cross member 1855 and tissue penetrating projections 1860 having sharpened tips 1865. In this example, tissue penetrating projections 1860 are positioned not at the ends of cross member 1855 but rather at a position slightly medial, such that arms 1870 are positioned on the outside rather than the inside of the fastener. In this case, after extragastric insertion into stomach tissue, the proximal ends 1875 of arms 1870 therefore preferably engage serosal tissue not only out of the plane of the fastener, as described for fastener 1800 of FIG. 18A, but also at a position farther away from the approximated tissue interface, which may further increase retention force and reduce the chances of slipping or tearing.

Figure 19:
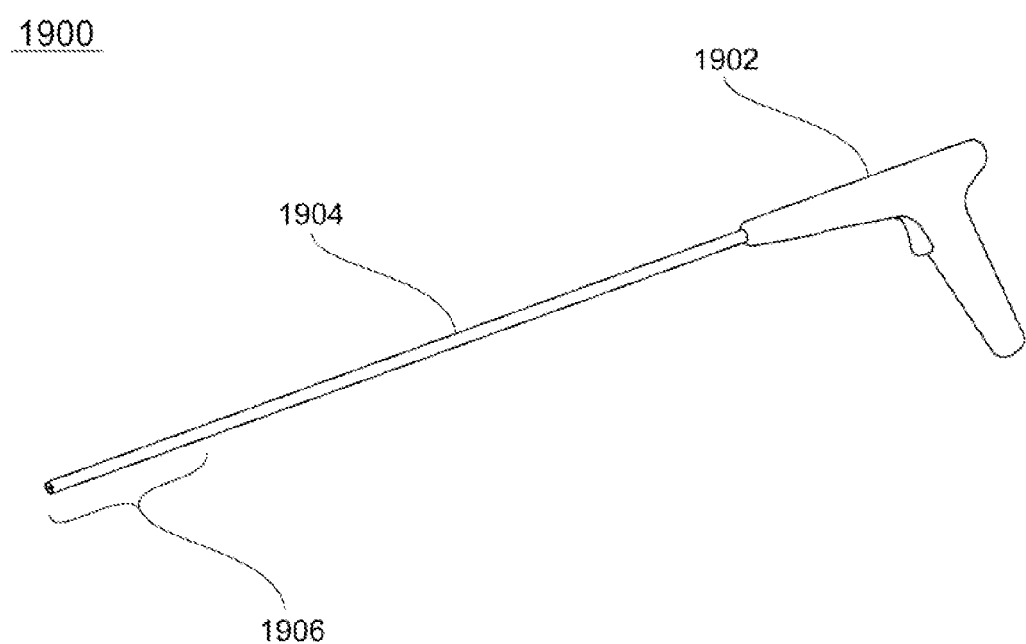
FIG. 19 illustrates a fastener applicator according to one embodiment of the present invention.

As illustrated in FIG. 19, a fastener applicator 1900 according to one embodiment of the present invention comprises a proximal handle assembly 1902, longitudinal tube assembly 1904, and distal fastener deployment assembly 1906 which is operably connected to handle assembly 1902. Tube assembly 1904 is configured to allow device 1900 to be inserted into the central working channel of the tissue approximation devices of the present invention (e.g. working channel 826 of device 800 shown in FIG. 8). The outer diameter of tube assembly 1904 is therefore preferably between 3 mm and 25 mm, more preferably between 4 mm and 18 mm, and most preferably between 5 mm and 15 mm.

The fastener applicator of the present invention may be designed to deploy one fastener (single fire instrument) or more than one fastener (multi-fire instrument) into tissue by propelling the fasteners out of the distal end of tube assembly 1904 and into target tissue at a predetermined speed and force. In a preferred embodiment, fastener applicator 1900 is a multi-fire device intended for single patient use, and is provided pre-loaded with a plurality of fasteners stored within tube assembly 1904. The speeds and forces at which fasteners are propelled into tissue may be significantly greater than what is typically achieved using prior art fastener deployment mechanisms (e.g. hand powered deformable staples, helical or threaded fasteners, tacks pushed directly into tissue, etc.). In this manner, the fastener applicators of the present invention provide more consistent and controlled fastener deployment and also overcome high tissue insertion forces to ensure complete fastener penetration and engagement within the target tissue. Propelling of fasteners is accomplished in fastener applicator 1900 using a unique spring loaded, impact driver-type mechanism described below.

Figure 20A:
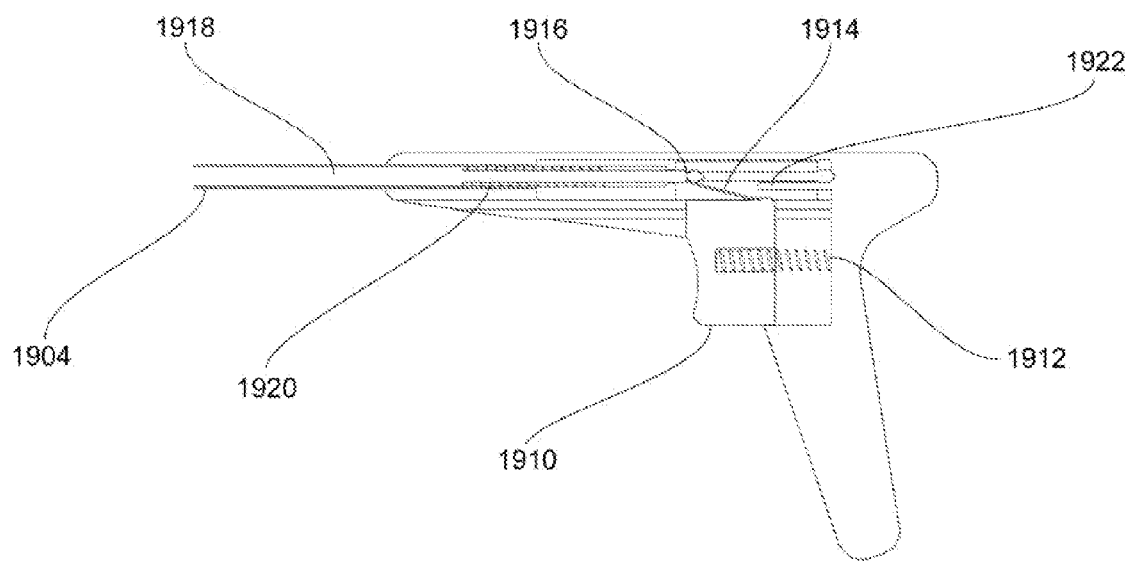

A detailed cross section of handle assembly 1902 in the pre-fired position is shown in FIG. 20A. To initiate an acutated firing cycle and thereby deploy a fastener into tissue, trigger 1910 is pulled by the operator. Trigger spring 1912 causes trigger 1910 to return to its original position when released, after firing. Cocking bar 1914 is fixedly connected at its proximal end to trigger 1910 and at its distal end is configured to engage within groove 1916 of driver 1918. In this manner, when trigger 1910 is pulled proximally by the operator, driver 1918 is also moved proximally, compressing and thereby storing potential mechanical energy in firing spring 1920. As trigger 1910 approaches its proximal most position, release pin 1922 presses against cocking bar 1914 causing it to elastically bend downward and thereby disengage from groove 1916. This releases driver 1918 and allows it to be propelled forward, thereby firing a fastener into tissue. The propelled forward motion of driver 1918 is powered by the release of mechanical energy stored within firing spring 1920. Accordingly, the speed and force of firing are determined by the materials properties and dimensions, etc., of firing spring 1920, which may be optimized to achieve various desired firing characteristics. In a preferred embodiment, the spring force may be variably adjusted by the user (e.g. by turning a knob provided within handle assembly 1902, not shown) based upon the tissue characteristics, type of fastener, and so on. When driver 1918 is released and firing is complete, driver 1918 returns to its original pre-fired (distal most) position. Similarly, when trigger 1910 is released and returns to its original pre-fired position, cocking bar 1914 re-engages with groove 1916 and the device is therefore readied for the next firing cycle.

Figure 20B:
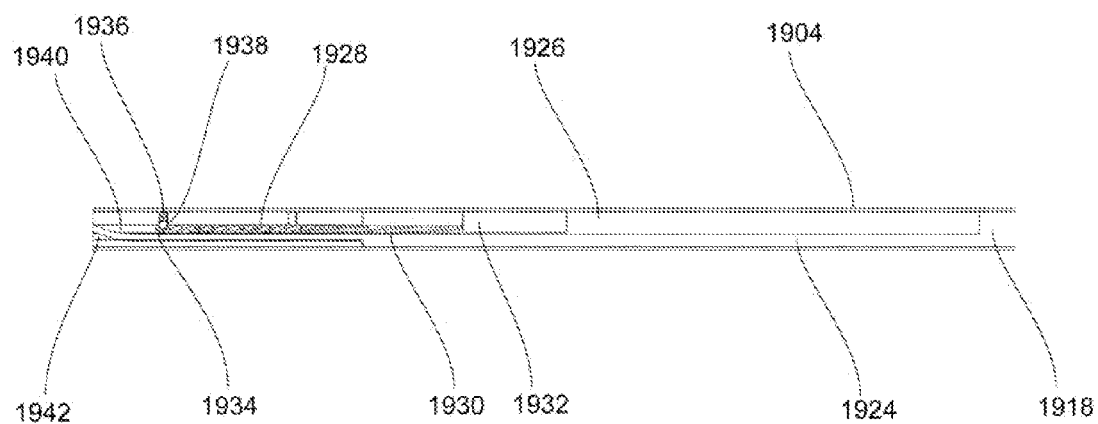

According to one embodiment of the present invention, in this example a multi-fire device, distal fastener deployment assembly 1906 is shown in the pre-fired position in FIG. 20B. Driver 1918 is slidably positioned within tube assembly 1904 and is configured having a reduced cross sectional area 1924 in its distal region. This provides space within tube assembly 1904 for fastener magazine 1926 within which a plurality pre-loaded fasteners 1928 are stored in a stacked configuration. Each time the device is actuated, fasteners 1928 are sequentially advanced distally, one position at a time, as a result of the force applied against the stack of fasteners 1928 by magazine spring 1930 that pushes at its proximal end against spring stop 1932 which is fixedly mounted within tube assembly 1904. Prior to said actuation, the distal most fastener in the magazine is in the loaded position 1934 and ready for deployment. Retainer spring 1936 and retainer ball 1938 temporarily hold the distal most fastener in the loaded position, providing a retention force against which magazine spring 1930 presses. Distal to the fastener in the loaded position 1934 is firing channel 1940, through which the loaded fastener will be propelled when driver 1918 is released after the operator fully actuates trigger 1910 in handle assembly 1902. Near its distal end, driver 1918 is configured with a flexible arm 1942, operation of which is explained below.

The details of operation of distal fastener deployment assembly 1906 during a single firing sequence is illustrated in FIG. 21. In FIG. 21A, the device is in the pre-fired position, as described previously (i.e. FIG. 20B). In FIG. 21B, the device is shown in the configuration immediately prior to the release of driver 1918, after trigger 1910 has been pulled to nearly its proximal most position by the operator and firing spring 1920 is fully compressed. During actuated retraction of driver 1918, flexible arm 1942 slides proximally and simultaneously elastically deforms into a flat configuration, allowing it to move underneath the stack of fasteners 1928 just until it's distal end passes beyond the proximal face of the fastener in the loaded position 1934. As illustrated in FIG. 21C, as soon as flexible arm 1942 moves proximal to the fastener in the loaded position 1934, flexible arm 1942 deflects upward, forcing the stack of fasteners proximally by compressing slightly magazine spring 1930 and thereby allowing the distal end of flexible arm 1942 to slide behind just the fastener in the loaded position 1934. This individually separates the fastener to be deployed 1944 from the remaining stack of fasteners 1928 and places the device in a ready-to-fire configuration. Upon release of driver 1918, actuated by the final proximal motion of trigger 1910 by the operator, the force supplied by firing spring 1920 is transmitted through driver 1918 into the fastener to be deployed 1944. By design, this force is sufficiently strong to overcome the frictional force of retainer spring 1936 and retainer ball 1938 that holds fastener 1944 in position. Driver 1918 moves distally and the fastener to be deployed 1944 is thereby propelled distally 1946 through firing channel 1940 and out of the device with substantial force and speed. FIG. 21D shows the position of flexible arm 1942 and the fastener to be deployed 1944 within firing channel 1940 immediately after driver 1918 has been released. As shown in FIG. 21E, upon completion of the firing cycle, the fastener to be deployed 1944 has been propelled from the distal end of tube assembly 1904 and driver 1918 has returned to its original pre-fired position. The stack of fasteners 1928 is advanced by magazine spring 1930 to place the next fastener in the loaded position 1934. When the operator then releases trigger 1910 in handle assembly 1902 (FIG. 20A), trigger 1910 springs back to its original pre-fired position and cocking bar 1914 re-engages with groove 1916 on the proximal end of driver 1918, and the device is ready for another firing cycle.

FIG. 22 illustrates the combined use of tissue approximating devices of the present invention along with the fasteners and fastener applicators of the present invention, together comprising a system 2200 of the present invention, used for the purpose of carrying out the surgical procedure described previously. System 2200 comprises tissue approximation device 2202 having fastener applicator 2204 inserted into its working channel. Although shown as separate devices in this embodiment, it should be recognized by those skilled in the art the these two devices, having substantially independent yet complementary functions, may readily be combined into a single unitary device having substantially the same features, actuation mechanisms and operational characteristics. Such integrated multi-functional devices are considered within the scope of the present invention.

Figure 22A:
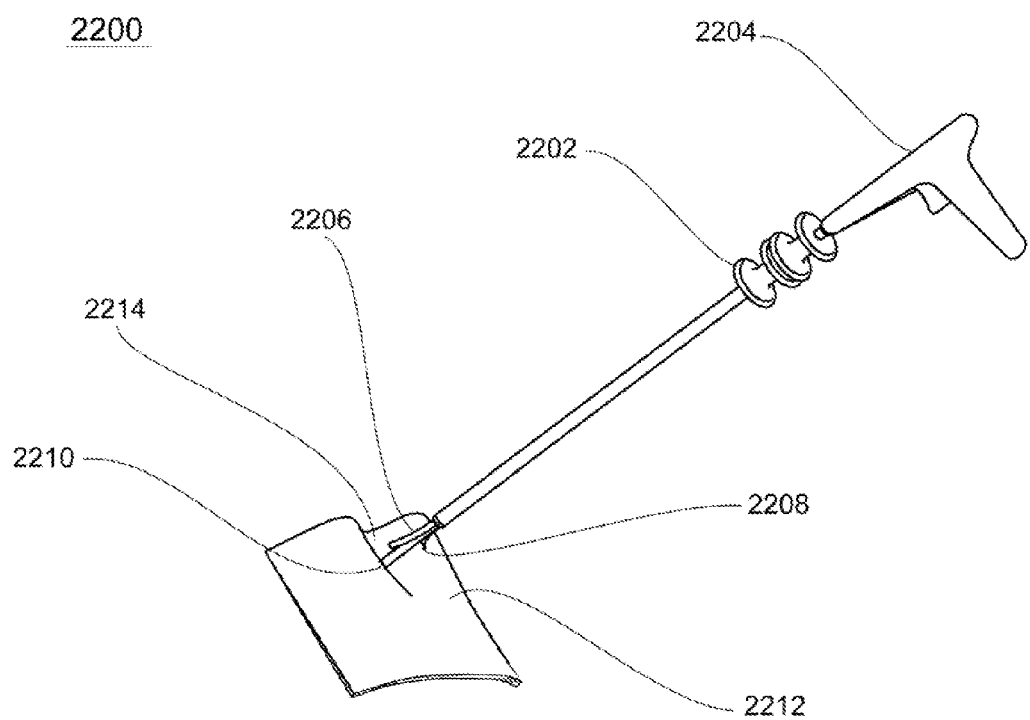

In FIG. 22A, tissue approximation device 2202 is designed and operates substantially similar to device 800 of FIG. 8, while fastener applicator device 2204 is designed and operates substantially similar to device 1900 of FIG. 19. In this illustration, tissue approximation device 2202 is shown in the deployed configuration with moveable arms 2206 extending distally from the device 2202 and having tissue hooks 2208 in position ready to engage tissue. The distal end 2210 of fastener applicator 2204 has been pushed proximally out of the working channel of device 2202 and extends distally from the end of the device, such that when positioned above and pushed against the extragastric surface 2212, tissue invagination 2214 is formed, which is the first step in forming the desired tissue fold.

Figure 22B:
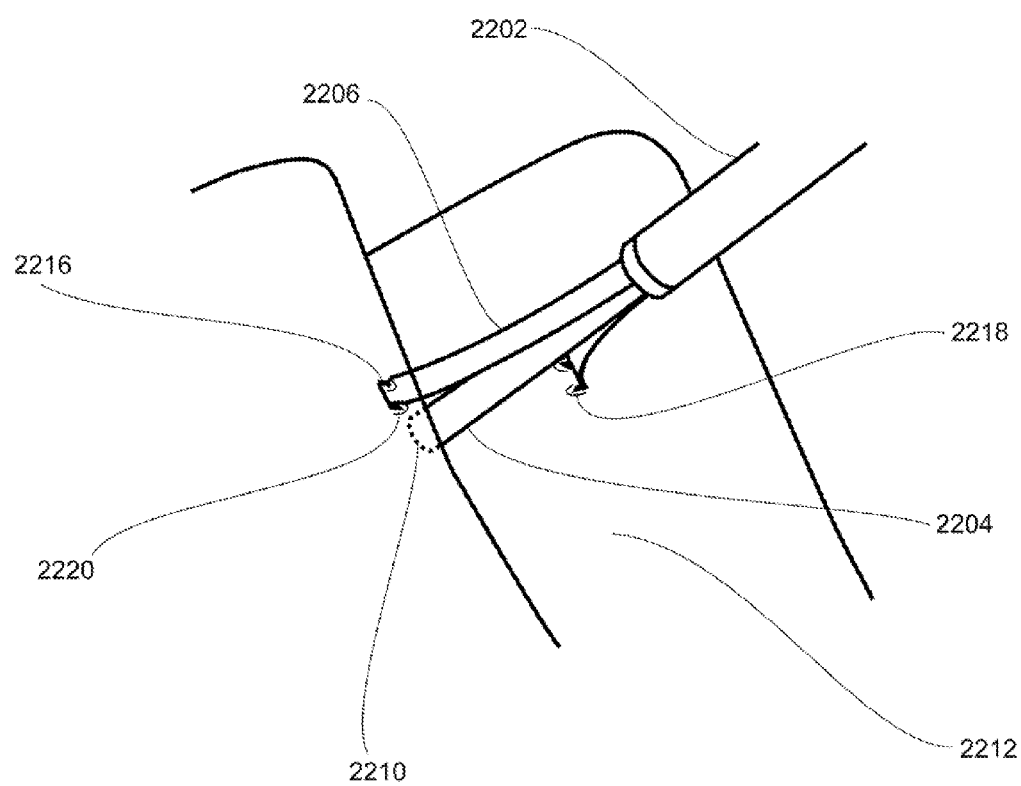

FIG. 22B shows a close up illustration of the distal end of tissue approximation device 2202 and fastener applicator 2204 after moveable arms 2206 have been pressed against the extragastric tissue surface 2212 such that tissue hooks 2216 have engaged tissue at locations 2218 and 2220. In this example, the distal end 2210 of fastener applicator 2204 is still being used to push against the extragastric tissue surface 2212 to ensure the desired tissue invagination continues, while tissue approximation device 2202 is now ready to be retracted to create a tissue fold, as described previously (see FIG. 12). Optionally, the distal end 2210 of fastener applicator 2204 may preferably be used during this time to disrupt the thin layer of mesothelial cells covering the serosa and thereby promote a healing response, according to the methods of the present invention, as described previously.

To secure the created tissue fold and produce a plication projecting into the gastrointestinal space, fastener applicator 2204 is retracted to a position such that its distal end is placed in intimate contact with the approximated tissue surfaces, substantially at the distal end of tissue approximation device 2202. An alignment mechanism (described previously, refer to FIG. 14) is provided to ensure proper orientation of fastener applicator 2204 relative to tissue approximation device 2202. This ensures that when the fastener applicator 2204 is fired and the fastener is propelled into tissue (as described in FIG. 21), the fastener will be properly positioned to reliably engage tissue on both sides of the approximated tissue interface (as shown in FIG. 17).

Figure 22C:
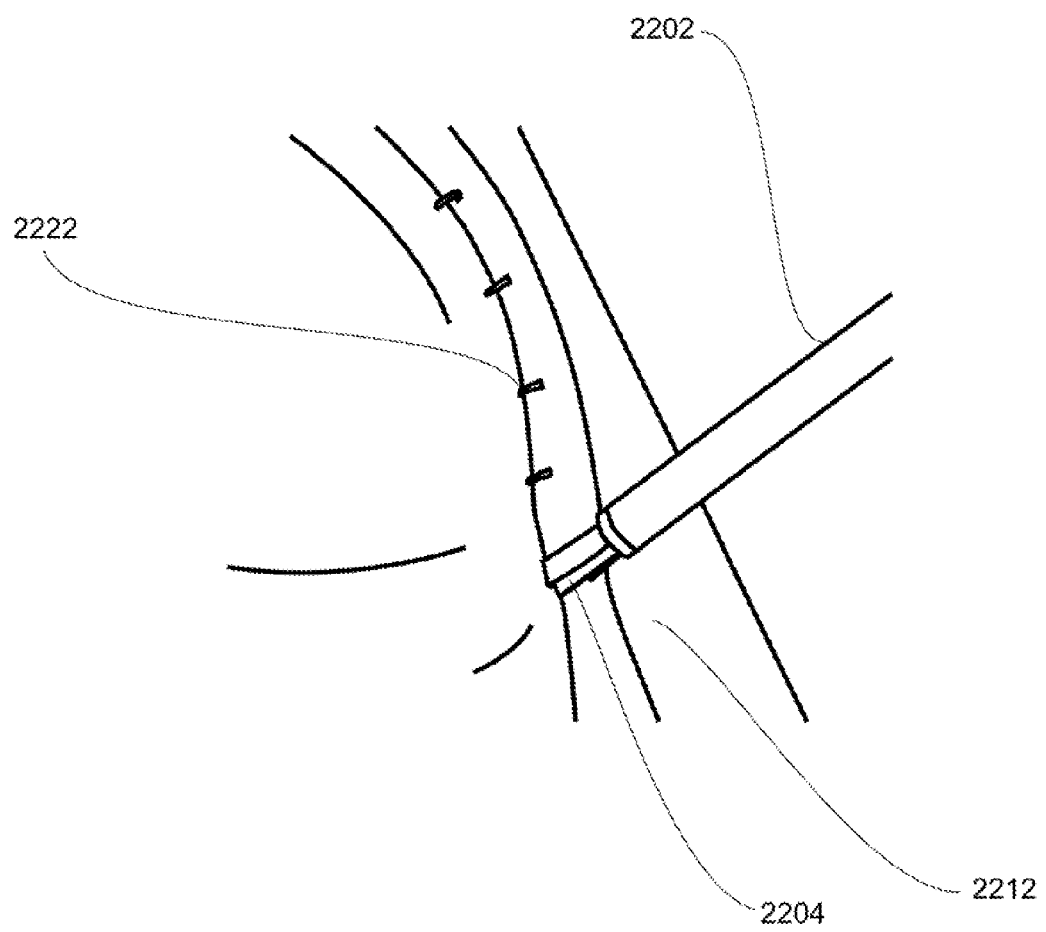

FIG. 22C shows a close up illustration of the distal end of tissue approximation device 2202 and fastener applicator 2204 being used on extragastric tissue surface 2212 to produce a plication projecting into the gastrointestinal space, according to the methods of the present invention. In this example, four tissue approximation steps have been completed and extragastric tissue fasteners 2222 have been placed at the site of each approximation step. Tissue approximation device 2202 is shown at a fifth location with moveable arms 2206 nearly fully retracted, just prior to the firing of fastener applicator 2204 to insert the next extragastric tissue fastener. In this manner the length of the plication may extended step by step, to create the necessary plication and thereby achieve the intended stomach volume reduction, as desired by the surgeon.

In other embodiments, described in detail below, the tissue approximating devices of the present invention may optionally incorporate operable means for articulating (i.e. rotating, deflecting or otherwise selectively moving and/or re-positioning) the distal end of the device relative to the position of the elongate tubular assembly. This functionality improves the surgeon's ability to quickly and efficiently engage and approximate the target tissue regardless of the angle of approach (which is dictated by the positioning of the laparoscopic access port or trocar), and thereby not only speeds the procedure but may allow the procedure to be performed using fewer trocars. In certain preferred embodiments, sufficient articulation functionality is provided in the device such that by appropriately placing a single trocar through the abdominal wall the entire method of the present invention can be completed.

One embodiment of an articulating device is shown in FIG. 23, which illustrates close up cross sectional views of the distal end of a device which operates similarly to the devices described previously. In FIG. 23A, which shows the device in the straight and retracted position, elongate tubular assembly 2305 is operatively connected to the distal articulating tissue approximation assembly 2310 via pivot joint 2315. Articulating tissue approximation assembly 2310 has two moveable arms that are joined at their proximal end creating a single moveable arm assembly 2320 that is retractably held by pin 2322, fixedly attached to the distal end of central cable 2324 passing through pivot joint 2315. Spring 2326 is compressed when moveable arm assembly 2320 is retracted into distal tube 2328, which occurs when the user operatively actuates the handle assembly (not shown) to thereby pull proximally on central cable 2324. When the user operatively releases tension on central cable 2324, spring 2326 expands and moveable arm assembly 2320 thereby extends out of the distal end of the device, as shown in FIG. 23B.

Arm tips 2330 and 2332, each having tissue engagement means 2334 and 2336, respectively, are then placed in proper deployed position for engaging tissue, as described previously. After tissue is engaged, the user again operatively actuates the handle assembly, thereby retracting moveable arm assembly 2320 back into distal tube 2328 (FIG. 23A), effectively approximating the engaged tissue locations at a position near the distal end of the device.

Figure 23A:
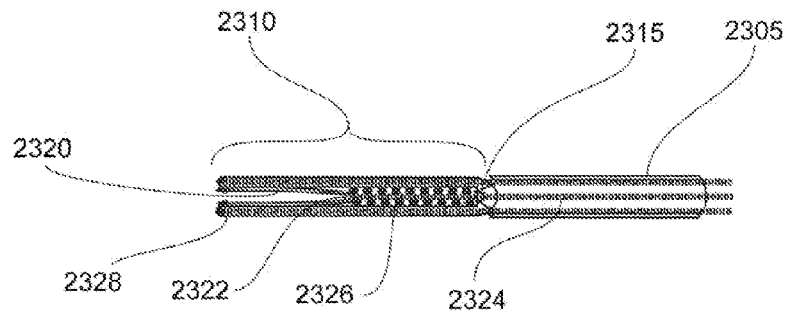
Figure 23B:
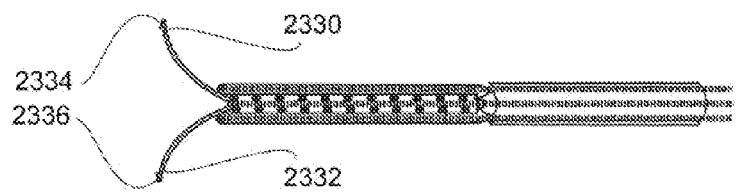
Figure 23C:
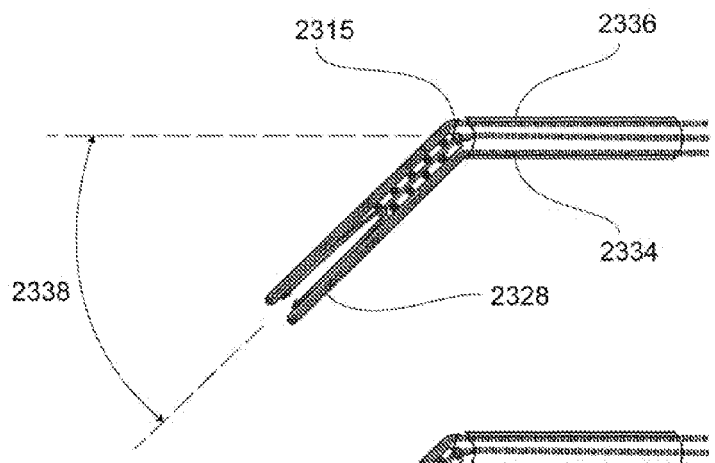
Figure 23D:
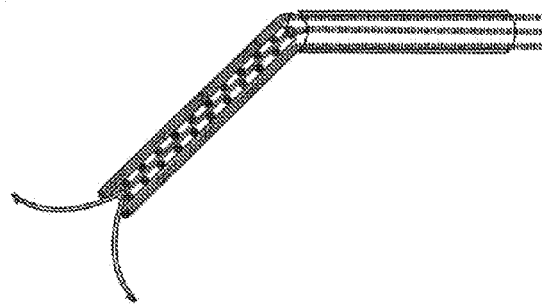

FIGS. 23C and 23D illustrate the same retracted and deployed configurations, respectively, however in these examples, the device has been operatively placed in an articulated position. Articulation is effected by a controlled rotation of distal articulating tissue approximation assembly 2310 around pivot joint 2315. To accomplish this rotation, opposing steering cables 2334 and 2336, passing through pivot joint 2315 and fixedly attached at the distal end of distal tube 2328, are operatively actuated from the handle assembly by the user. In the example shown, steering cable 2334 has been pulled in tension (shortening it) while steering cable 2336 has been slidably released (lengthening it), and distal articulating tissue approximation assembly 2310 has thereby been rotated downward by angle of deflection 2338. The original straight position may be restored and/or the direction of rotation may be reversed simply by placing tension on steering cable 2336 while slidably releasing steering cable 2334. A variety of pivotable joint mechanisms known to those skilled in the art may be used such as hinges, elbows, ball joints, universal joints, and the like. Using such pivotable joint mechanisms and two opposing steering cables, as shown in this example, deflection is generally limited to being up or down within a single plane, and the maximum angle of deflection possible is typically less than 90 degrees. When in an articulated position, actuation of moveable arm assembly 2320 to engage and approximate tissue is accomplished the same as described above (FIGS. 23A and 23B). In this manner, the articulation function is therefore operatively controlled independently from the actuation function.

Figure 24A:
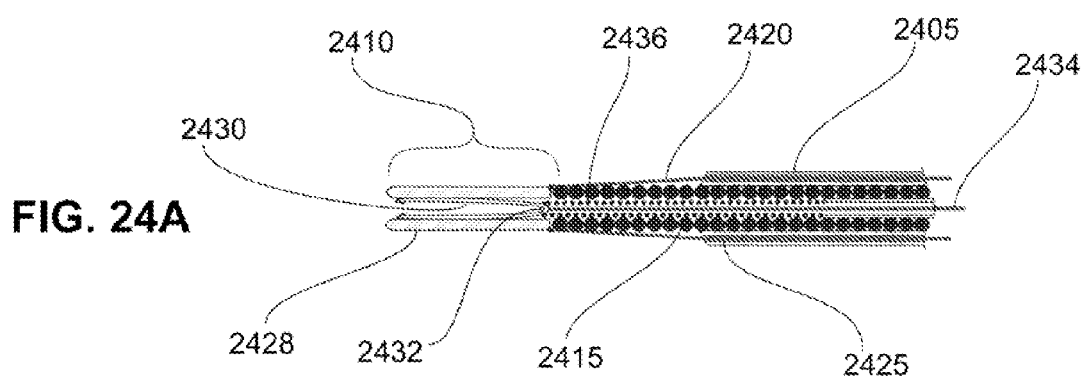
Figure 24B:
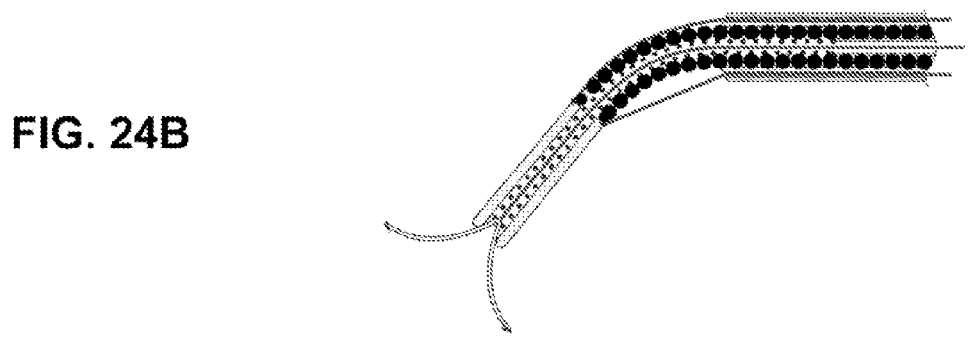

Other embodiments incorporating operable means for articulating the distal end of the device are illustrated in FIGS. 24 and 25. FIG. 24 shows close up cross sectional views of the distal end of a device in the straight and retracted configuration (FIG. 24A) and the articulated and deployed configuration (FIG. 24B). In this embodiment, the pivot joint has been replaced with a flexible member 2415 extending between elongate tubular assembly 2405 and distal articulating tissue approximation assembly 2410. When used with more than two steering cables 2420 (four cables are used in the embodiment of FIG. 24) that are routed through cable channels 2425 and fixedly attached to distal tube 2428, this device is capable of deflecting in any desired direction relative to the positioning of the handle assembly. The actuation mechanism and tissue approximation steps involving moveable arm assembly 2430, pin 2432, central cable 2434 and spring 2436 are substantially similar to that described previously for device shown in FIG. 23. The advantages of this design are that the surgeon is provided with maximum freedom by being able to deflect the distal articulating tissue approximation assembly in any desired direction relative the position of the handle assembly.

Figure 25A:
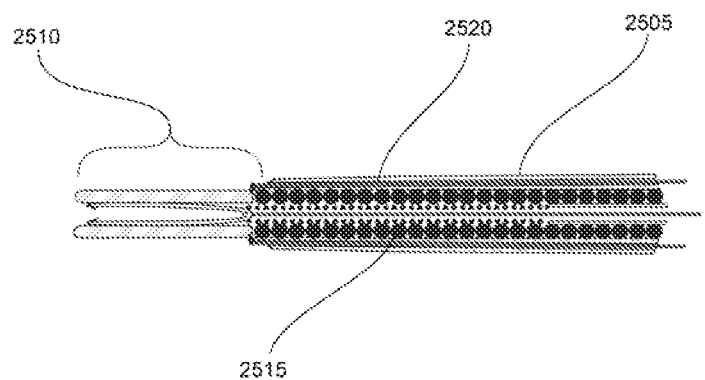
Figure 25B:
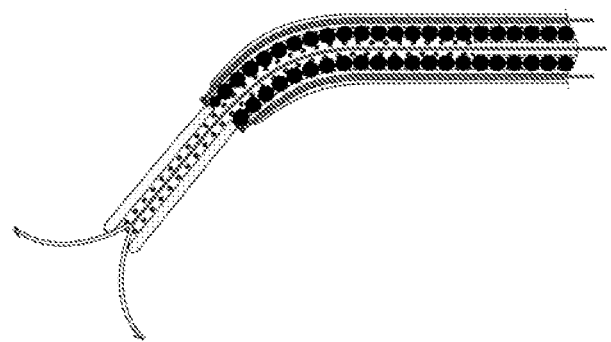

FIG. 25 shows close up cross sectional views of the distal end of a device in the straight and retracted configuration (FIG. 25A) and the articulated and deployed configuration (FIG. 25B). In this example, which is similar to devices described previously, the distal end of elongate tubular assembly 2505 is made from flexible material and provides a protective covering for flexible member 2515 and steering cables 2520, extending all the way to and connecting directly with distal articulating tissue approximation assembly 2510. This provides for a simpler, cleaner and safer articulating device configuration, while retaining all the advantages described previously.

Figure 26A:
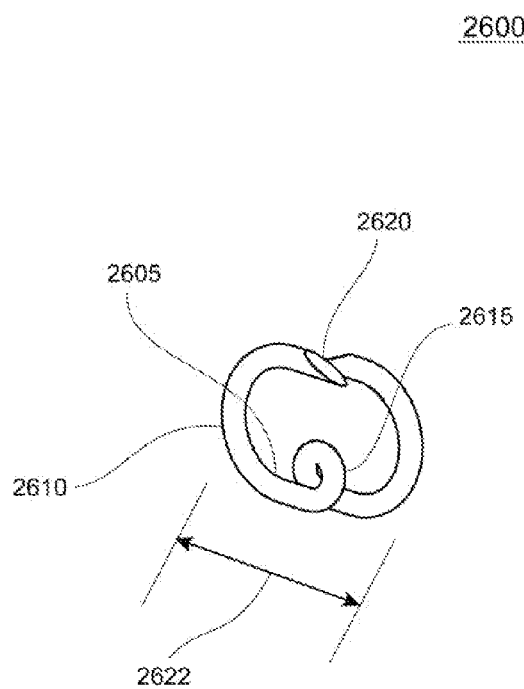
Figure 26B:
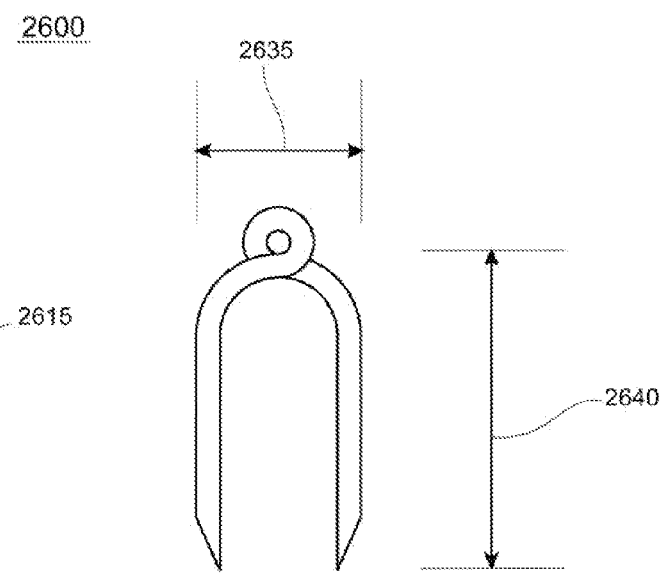

According to another embodiment of the present invention, tissue retaining fastener 2600 is shown in the deployed configuration in FIG. 26A and in the pre-deployed configuration in FIG. 26B. The fastener consists of a connecting member 2605 from which two or more self-actuating, reconfigurable tissue penetrating members 2610 extend. Fastener 2600 is produced from a highly flexible material capable of substantial elastic deformation, preferably a shape memory or superelastic material such as NiTi alloy or similar. Fastener 2600 may be produced from wire, ribbon, sheet, bar stock, and the like. Connecting member 2605 may optionally include spring element 2615, which can be a coil spring, leaf spring, flexible hinge, and the like, that may be incorporated to increase the deployment and/or retention forces of the fastener. Each of tissue penetrating members 2610 further incorporates a sharpened tip 2620 at its distal end, which are preferably designed and configured to reduce the required tissue insertion forces while simultaneously minimizing tissue damage. As shown in FIG. 26A, in the deployed configuration (i.e. the self-actuating reconfigured shape after implantation in tissue) fastener 2600 forms a loop having largest dimension 2622 that at least substantially encloses tissue. A variety of shapes may be used to form the loop, such as circular shapes, oval shapes, elliptical shapes, and so on. It is desirable that, after deployment, sharpened tips 2620 are positioned so as not to pose a risk of irritating tissue or causing tissue damage. In the example shown, sharpened tips 2620 are designed to at least partially overlap one another.

Figure 27A:
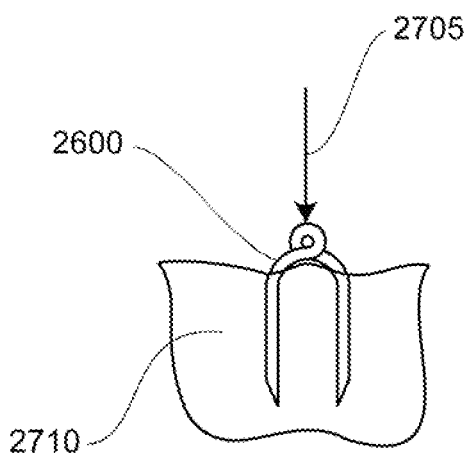
Figure 27B:
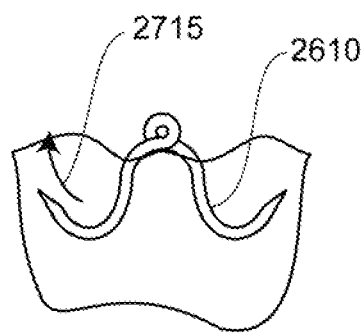
Figure 27C:
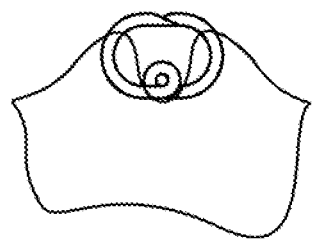

In the pre-deployed configuration, fastener 2600 is held within a suitable fastener applicator (described below) in the shape illustrated in FIG. 26B. The deployment sequence is illustrated in FIG. 27. By mechanically restraining fastener 2600 in the pre-deployed shape, elastic potential energy is stored in the reconfigurable tissue penetrating members 2610 that provides a driving force (i.e. spring bias) for the fastener to automatically return to the deployed shape (FIG. 26A). After being propelled forward 2705 into tissue 2710 by firing of the applicator (not shown) to produce initial tissue penetration (FIG. 27A), tissue penetrating members 2610 elastically deform in the proximal direction 2715 in a self actuating manner, (FIG. 27B), thereby engaging and substantially enclosing tissue (FIG. 27C). One unique aspect of fastener 2600 is the substantially backward (i.e. proximal) direction of motion 2715 in which the distal ends self-actuating tissue penetrating members 2610 move during reconfiguration to close the fastener, relative to the forward (i.e. distal) direction of motion 2705 of the fastener when penetrating tissue. In this reverse direction reconfiguration process, a loop shaped fastener is formed in the tissue (FIG. 27C), while having sharp tissue penetrating tips 2620 that are positioned, after reconfiguration, near or above the penetrated tissue surface.

For minimally invasive applications, fastener 2600 preferably has a relatively small width 2635 such that it can be held within the smallest possible fastener applicator. Width 2635 is therefore preferably less than about 12 mm, more preferably less than about 8 mm and most preferably less than about 5 mm. The length 2640 of tissue penetrating members 2610 limits the final size of the loop formed by the deployed fastener. Length 2640 is preferably between 5 and 50 mm, more preferably between 8 and 30 mm, and most preferably between 10 and 20 mm. An unique aspect of this self-expanding and self-actuating fastener design is that the size of the loop 2622 in the final deployed configuration (FIG. 26A) can be substantially larger than the diameter of the fastener applicator needed to deploy said fasteners. For example, in one embodiment that has been successfully tested, a fastener similar to fastener 2600 was produced from 0.38 mm diameter superelastic NiTi wire. The width 2635 of the fastener in the pre-deployed configuration was approximately 2.0 mm (easily deployed from a 5 mm applicator), the length 2640 of tissue penetrating members 2610 was approximately 10 mm, and the final loop size when deployed in tissue 2622 was approximately 7 mm. By engaging and enclosing a larger amount of tissue during fastener reconfiguration (FIG. 27), significantly increased tissue retention forces can be achieved using the smallest possible (i.e. a truly minimally invasive) delivery device.

Figure 28A:
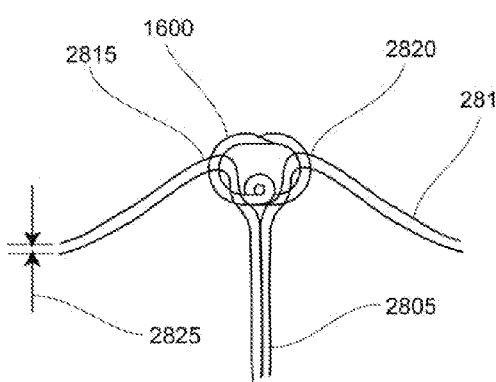

During the use of a fastener such as fastener 1600 for the purpose of extragastrically producing a plication by securing invaginated tissue folds created by approximating stomach tissue, according to the methods of the present invention, it is possible to place the fastener in either configuration shown in FIG. 28. In FIG. 28A, fastener 1600 is securing tissue fold 2805 created in gastrointestinal tissue layer 2810 by penetrating the adjacent shoulders 2815 and 2820, respectively, that were created during tissue approximation. Note, the dimensions of fastener 1600 are large relative to the thickness 2825 of tissue layer 2810, and the fastener therefore has penetrated completely through the tissue. Complete penetration of fasteners though the tissue is acceptable practice in current gastric surgeries when using deforming box-type staples of the prior art.

Figure 28B:
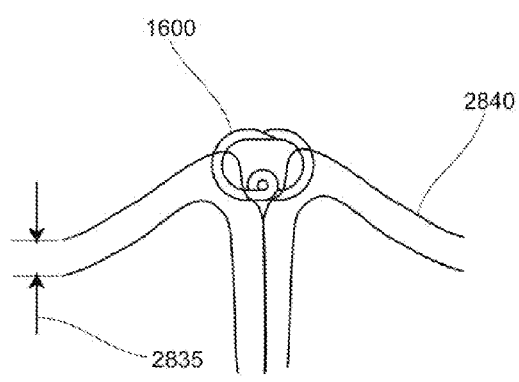

An alternative and preferred fastener configuration possible with fasteners of the present invention is shown in FIG. 28B. In this case, the dimensions of fastener 1600 are small relative to the thickness 2835 of tissue layer 2840, and the fastener therefore has penetrated through the outermost (serosal) tissue layer and only partially through the underlying muscularis tissue layers, avoiding full thickness through penetration of the tissue. Since most of the holding force for the fastener is provided by secure engagement with the thin yet tough serosal layer, this fastener configuration can be at least as strong as that shown in FIG. 28A, while avoiding any possible complications that may result from perforation of the gastrointestinal tract or damage to the internal (mucosal) layer involved in digestion. In fact, it is unexpectedly anticipated that the entirely extragastric fastener placement may be stronger than the full thickness through penetration placement since the muscularis and mucosal layers are inherently unstable with respect to retaining fasteners long-term. Fasteners may be placed according to the configuration of FIG. 28A, FIG. 28B, and combinations of the foregoing.

Figure 29A:
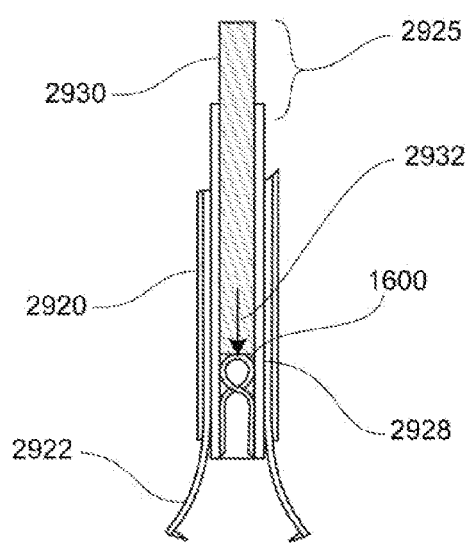
Figure 29B:
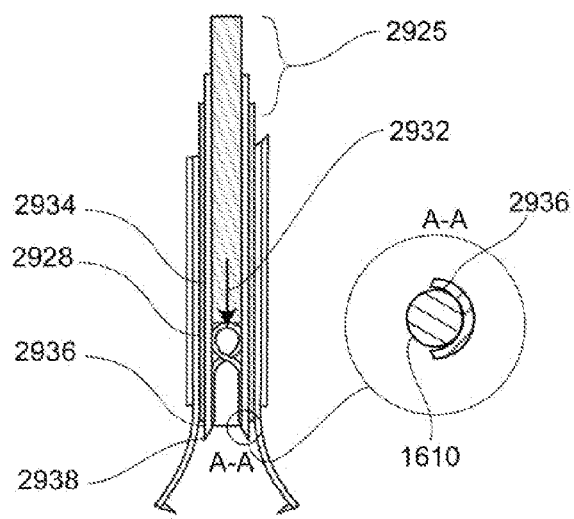

Detailed close up distal end views showing two different embodiments for deploying fasteners 1600 into approximated tissue are shown in FIGS. 29A and 29B, respectively. In FIG. 29A, outer tube 2920 and moveable arms 2922 of a tissue approximation device as described previously are shown, with moveable arms positioned in a partially deployed configuration. The distal tube assembly 2925 of the fastener applicator device is shown inserted into the working channel. One or more of fasteners 1600 are loaded into and constrained in the pre-deployed (spring-biased) configuration by applicator tube 2928. Pusher 2930 is operably connected to the applicator hand assembly (not shown), and is configured to move distally when the applicator hand assembly is actuated by the user. When in the ready-to-fire configuration, fastener 1600 is positioned just inside the distal end of applicator tube 2928, and pusher 2930 is positioned and configured to apply a longitudinal force 2932 against the proximal end of fastener 1600 when actuated. When the applicator handle assembly is actuated by the user, pusher 2930 will force fastener 1600 out of the distal end of the device, where it penetrates tissue and reconfigures in a self-actuating manner to securely engage and substantially enclose tissue, as described previously.

An alternative embodiment for distal tube assembly 2925 is shown in FIG. 29B. In this case, deployment tube 2934 is slidably positioned inside applicator tube 2928, and stores and retains fastener 1300 in the pre-deployed configuration. At the distal end of deployment tube 2934 are insertion guides 2936 that are configured with sharpened tips 2938 which are designed to penetrate tissue prior to deployment of fastener 1600 when deployment tube 2934 is actuated by the user and thereby moved distally out of applicator tube 2928. Insertion guides 2936 have a semicircular cross section designed to slidably engage the tissue penetrating members 1610 of fastener 1600, as shown in the magnified cross section view A-A. In this manner, the tissue penetrating members 1610 of fastener 1600 are retained in the pre-deployed configuration while insertion guides 2936 initially penetrate tissue to a pre-determined depth, before firing the fastener. When fastener 1600 is subsequently forced out of the device by the actuated distal movement of pusher 2930, the tissue penetrating members 1610 are released from the constrained (pre-deployed) configuration only after first reaching a prescribed tissue depth. By controlling the depth of penetration of the insertion guides 2936 prior to fastener deployment, relative to the size of the fastener, it is possible to ensure accurate and reproducible fastener placement, resulting in optimal engagement and enclosing of tissue upon reconfiguration of fastener 1600. This will be illustrated and described in greater detail below.

Figures 30A, 30B:
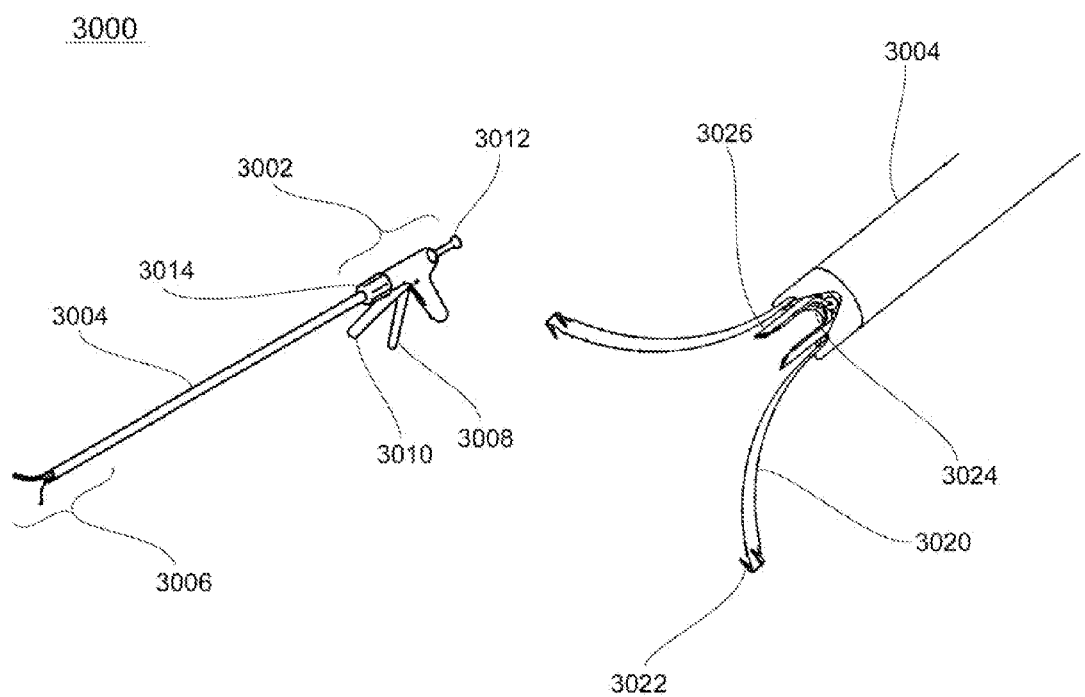

Although the tissue approximation devices, tissue fasteners and fastener applicator devices comprising the systems of the present invention are illustrated above (e.g. FIG. 29) as being separate devices, it should be recognized by those skilled in the art the these devices, having substantially independent yet complementary functions, may readily be combined and integrated into a single unitary device having substantially the same features, actuation mechanisms and operational characteristics. Accordingly, an example of such an integrated all-in-one device is illustrated in FIG. 30. FIG. 30A shows an overview of device 3000, having proximal handle assembly 3002, longitudinal tube assembly 3004 and distal tool assembly 3006, which incorporates both tissue approximation and tissue fastening mechanisms and is operably connected to actuating mechanisms in handle assembly 3002. Handle assembly 3002 is provided with first actuating means 3008 used for actuating the tissue approximation mechanism and second actuating means 3010 used for actuating the tissue fastening mechanism. Third actuating means 3012 is optionally included and may be used to actuate the optional serosal treatment mechanism. Rotating collar 3014 is provided to allow the longitudinal tube assembly to be oriented independently from the orientation of handle assembly 3002. A detailed close up view of distal tool assembly 3006 positioned at the distal end of longitudinal tube assembly 3004 is shown in FIG. 30B. Moveable arms 3020 are shown in the deployed configuration, each having tissue engagement means 3022 positioned at its distal end. Fastener 3024 (substantially similar to fastener 1600) is shown in the ready-to-fire position, being restrained in the pre-deployed (spring-biased) configuration by, and slidably within, insertion guides 3026.

Figure 31A:
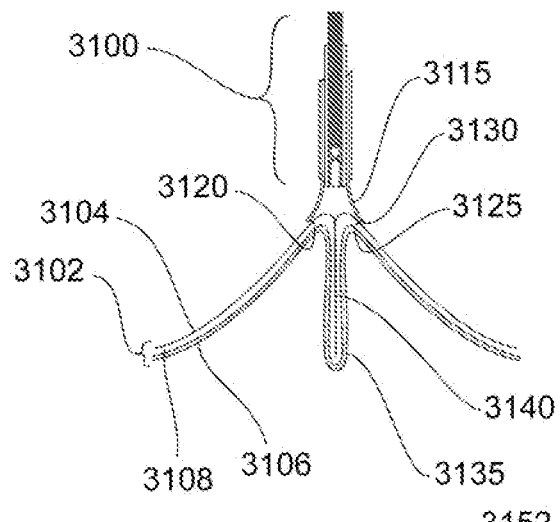
Figure 31B:
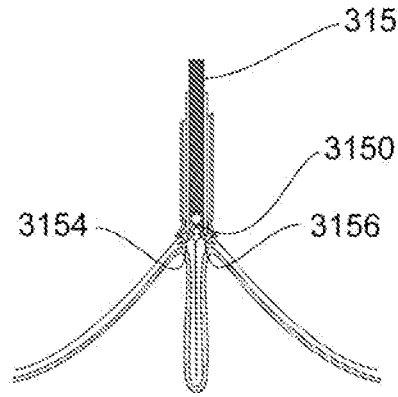
Figure 31C:
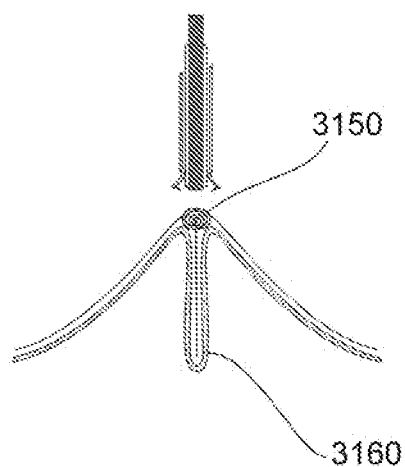

The use of the above described devices and systems for carrying out the surgical procedure of the present invention will now be described in greater detail. FIG. 31 schematically illustrates the use of system 3100. In FIG. 31, stomach tissue 3102 is shown, having exterior serosal tissue layer 3104, internal mucosal tissue layer 3106, with muscularis tissue 3108 positioned between. After obtaining minimally invasive surgical access to the stomach, a tissue fold is first created by the initial actuated deployment (not shown) of moveable arms 3115 and subsequent engagement of tissue at two separate locations (i.e. 3120 and 3125) by tissue engagement means 3130. During actuated retraction of moveable arms 3115 back into device 3100, as illustrated in FIG. 31A, tissue locations 3120 and 3125 become approximated near the distal end of device 3100. In this manner, an invaginated tissue fold 3135 is created whereby intimate serosa-to-serosa contact area 3140 is established inside said tissue fold. Prior to or during the above tissue approximation step, the tissue is optionally treated to promote a healing response across the serosa-to-serosa interface. After tissue approximation is completed, as illustrated in FIG. 31B, actuated deployment of tissue fastener 3150 (substantially similar to fastener 1300 of FIG. 13) occurs. In the example shown, the deployment mechanism is similar to that illustrated previously wherein deployment occurs as a result of the forward (distal) motion of pusher 3152, during which each of tissue penetrating members 3154 and 3156 penetrates tissue locations 3120 and 3125, respectively, and fastener 3150 reconfigures in a self-actuating manner to its deployed configuration. Upon completion of fastener deployment, as shown in FIG. 31C, fastener 3150 securely engages the approximated tissue, producing plication 3160 projecting into the gastrointestinal space. While complete penetration is acceptable, in the example shown, fastener 3150 penetrates and engages only serosal tissue layer 3104 and muscularis tissue 3108, without penetrating completely through the gut wall or otherwise disrupting mucosal tissue layer 3106. A strong serosa-to-serosa bond will form across contact area 3140 after approximately 7 days beyond surgery, thereby ensuring long-term durability to plication 3160.

Figure 32A:
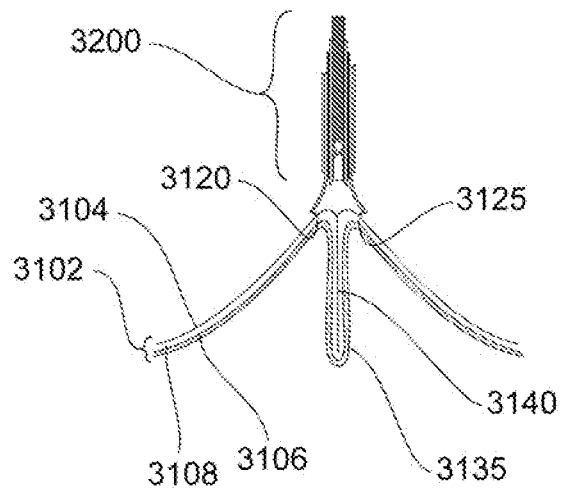
Figure 32B:
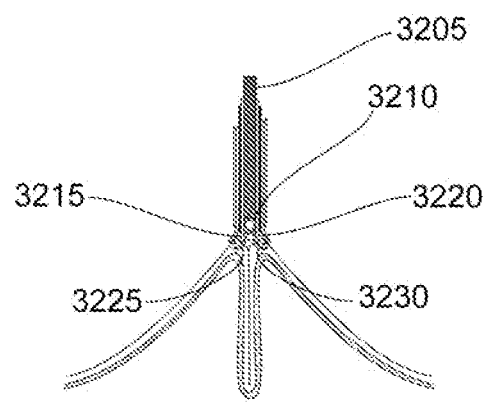
Figure 32C:
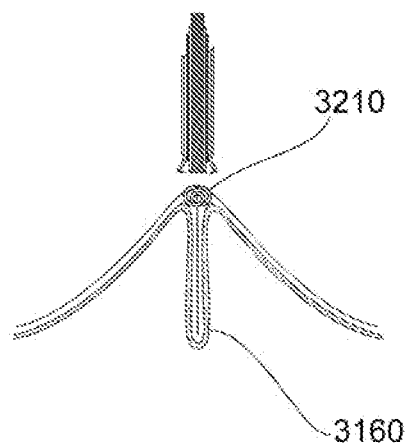

FIG. 32 illustrates substantially the same tissue and device configurations and operational sequence as in FIG. 31, however in the example of system 3200, the fastener deployment mechanism is substantially similar to that shown previously in FIG. 29B. Accordingly, in FIG. 32B, prior to the forward (distal) motion of pusher 3205 to deploy the fastener 3210 into tissue, insertion guides 3215 and 3220 are first extended distally from the end of the device, thereby penetrating tissue to a pre-determined depth, followed by the subsequent deployment of penetrating members 3225 and 3230. In this manner, the self-actuating reconfiguration of fastener 3210 is further controlled and optimized, producing more accurate and repeatable tissue engagement (FIG. 32C).

Figure 33A:
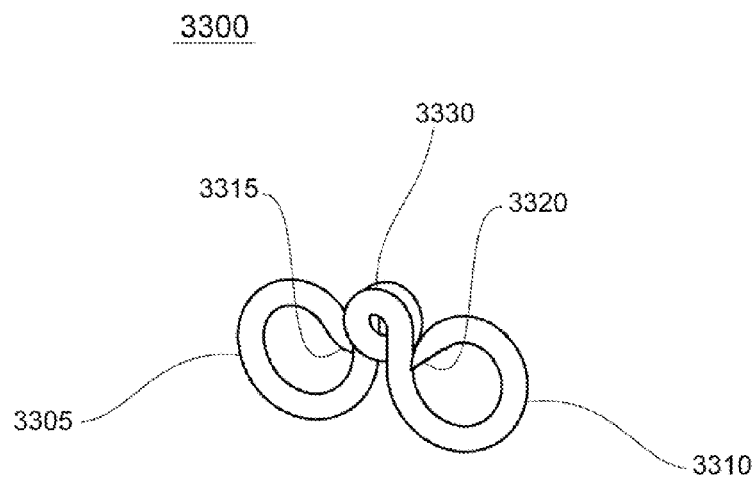
Figure 33B:
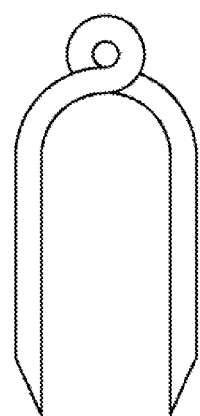

An alternative embodiment of a fastener of the present invention is illustrated in FIG. 33. Fastener 3300 is a self-actuating, backward (proximal direction) forming flexible-type fastener substantially similar to fastener 1600 (FIG. 16). However, the shape in the deployed configuration (FIG. 33A) has been modified to more effectively engage and securely hold the approximated tissue of the created tissue fold. As shown in FIG. 33A, each of the reconfigurable tissue penetrating members 3305 and 3310 forms a substantially closed loop on itself, with sharpened tips 3315 and 3320, respectively, positioned close to the proximal end of the penetrating members. Optional spring element 3330 positioned between the penetrating members may be used to provide additional force and/or holding strength to the fastener.

Figure 34A:
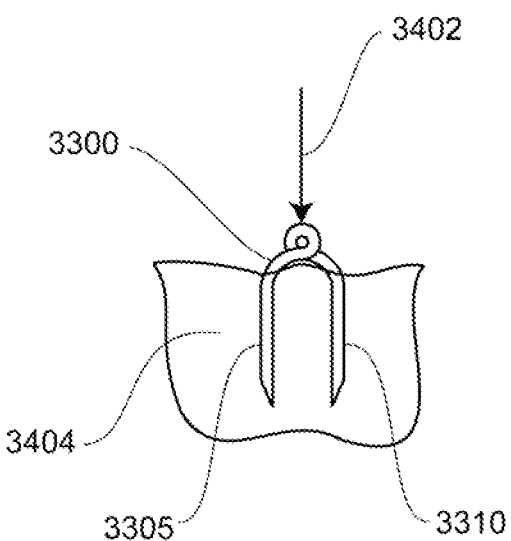
Figure 34B:
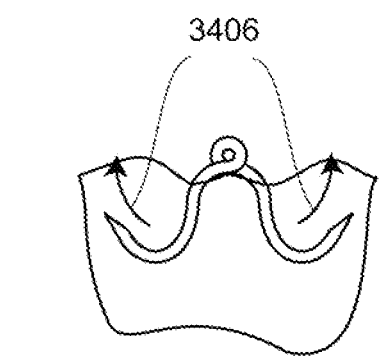
Figure 34C:
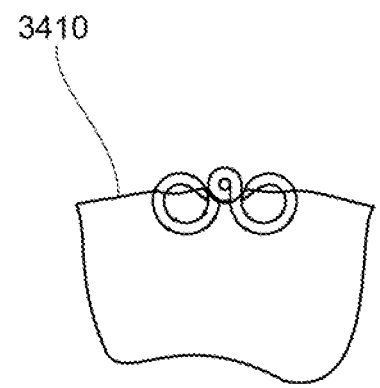

As shown in FIG. 34, the deployment sequence for fastener 3300 is substantially similar to that shown previously. By mechanically restraining fastener 3300 in the pre-deployed shape, elastic potential energy is stored in the reconfigurable tissue penetrating members 3305 and 3310 that provides a driving force (i.e. spring bias) for the fastener to automatically return to the deployed shape (FIG. 33A). After being propelled forward 3402 into tissue 3404 by firing of the applicator (not shown) to produce initial tissue penetration, tissue penetrating members 3305 and 3310 elastically deform in the proximal direction 3406 in a self actuating manner, (FIG. 34B), thereby engaging and substantially enclosing tissue (FIG. 34C). Similar to fastener 1600, a unique aspect of fastener 3300 is the substantially backward (i.e. proximal) direction of motion 3406 in which the distal ends self-actuating tissue penetrating members 3305 and 3310 move during reconfiguration to close the fastener, relative to the forward (i.e. distal) direction of motion 3402 of the fastener when penetrating tissue. In this reverse direction reconfiguration process, each tissue penetrating member independently forms a substantially closed loop in the tissue (FIG. 34C), while having sharp tissue penetrating tips 3315 and 3320 that are positioned, after reconfiguration, in such a manner so as not to produce tissue irritation or damage after fastener placement. Another unique aspect of this fastener that improves its holding strength when placed extragastrically in stomach tissue can be observed in FIG. 34C. Note that during reconfiguration the fastener actually passes through the thin, tough external serosal tissue layer 3410 two or more times (three times in the example shown), resulting in significantly greater holding force for the deployed fastener.

Figure 35A:
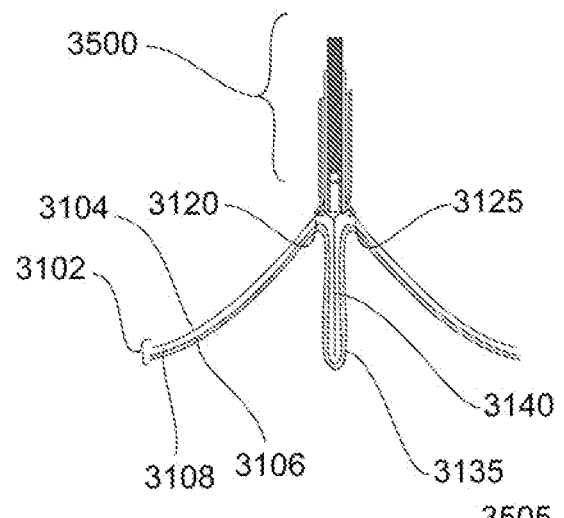
Figure 35B:
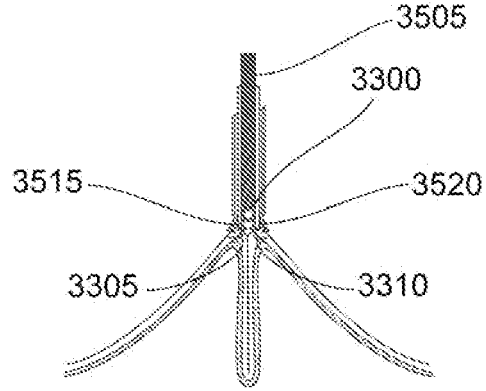
Figure 35C:
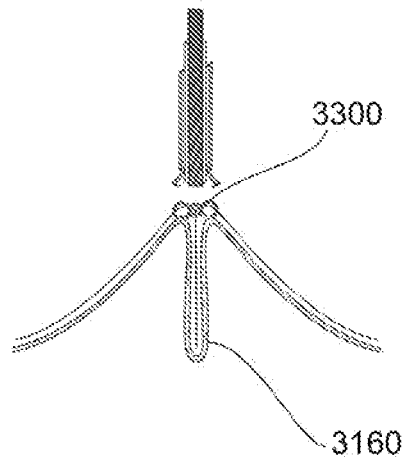

FIG. 35 illustrates the use of fastener 3300, along with integrated device system 3500, for the surgical method of the present invention. The tissue and device configurations and operational sequence are substantially similar to that described previously. Pusher 3505 propels fastener 3300 out of the distal end of the device, after insertion guides 3515 and 3520 have penetrated tissue. This allows tissue penetrating members 2205 and 2210 to reconfigure in a self-actuating manner, thereby accurately and controllably engaging and securing the tissue fold 2035 to produce a plication 2060 projecting into the gastrointestinal space. In the example shown, a completely extragastric fastener placement is shown, and a strong serosa-to-serosa bond will form across contact area 2040 after 7 days beyond surgery, thereby ensuring long-term durability of plication 2060.

We claim:
1. A device for engaging, approximating and fastening tissue comprising: a tool assembly adapted for insertion into a body cavity and having a working channel and at least two extendible members adjustable between an insertion condition and an extended condition, each of the extendible members comprising at least one associated tissue engagement mechanism at its distal end for piercing tissue; an actuating mechanism adapted to move at least one tissue engagement mechanism relative to another tissue engagement mechanism to approximate tissue engaged by the tissue engagement mechanisms; a plurality of box-type staples positioned in a pre-deployed state and movable into a pre-fire position in the working channel, each of the staples having at least two staple legs and, in the pre-fire position, each of the staple legs being located peripherally with respect to the tissue engagement mechanisms as positioned in the insertion condition; and an integrated tool for reconfiguring the staples and fastening approximated tissue comprising movable pistons positioned at the distal end of the tool assembly and a stationary anvil positioned centrally of the pistons.

2. The device of claim 1, wherein each of the at least two extendible members is movable axially and/or radially away from a distal end of the device.

3. The device of claim 1, wherein each of the tissue engagement mechanisms is selected from the group consisting of: hooks; barbs, teeth, clips, t-tags, and combinations thereof.

4. The device of claim 1, wherein each of the tissue engagement mechanisms comprises at least one sharpened tip.

5. The device of claim 1, wherein each of the at least two extendible members comprises a substantially rigid structure.

6. The device of claim 1, wherein each of the at least two extendible members comprises a substantially flexible structure.

7. The device of claim 1, wherein each of the tissue engagement mechanisms is mounted on a flexible tether.

8. The device of claim 7, wherein the flexible tethers comprise a suture or a wire.

9. The device of claim 7, additionally comprising an actuating mechanism for retrieval of flexible tethers.

10. The device of claim 9, wherein the actuating mechanism retrieves the flexible tethers to approximate tissue engaged by the tissue engagement mechanisms.

11. The device of claim 9, additionally comprising as cinching member, and wherein the actuating mechanism slides to cinching member through which the flexible tethers pass down the length of the tethers to approximate tissue engaged by the tissue engagement mechanisms.

12. The device of claim 7, additionally comprising a cinching member through which the flexible tethers pass.

13. The device of claim 1, wherein the extendible, members have a predetermined shape when in the expanded state that includes at least two bends having radii of curvature in substantially opposing directions.

14. A device for engaging, approximating and fastening tissue comprising; a tool assembly adapted for insertion into a body cavity and having at least two extendible members adjustable between a pre-deployed, biased insertion condition and a deployed extended condition in which the extendible members form a pre-determined shape, each of the extendible members comprising at least one associated tissue engagement mechanism having a pointed and sharp tissue hook for penetrating tissue; an actuating mechanism adapted for positioning at least one of the two tissue engagement mechanisms spaced apart from another tissue engagement mechanism; an integrated tool having a spring loaded, impact driver mechanism configured to deploy a plurality of tissue retaining fasteners sequentially for fastening approximated tissue; and a plurality of tissue retaining fasteners retained in the tool assembly.

15. The device of claim 14, wherein the integrated tool is configured to deploy individual fasteners by propelling the fasteners from the distal end of the device at a pre-determined speed and force.

16. The device of claim 14, wherein the integrated tool is configured to deploy multiple fasteners sequentially without reloading.

17. The device of claim 14, wherein the at least one tissue retaining fastener is selected from the group consisting of: sutures, staples, screws, tacks, clips, hooks, clamps, t-tags, helical fasteners, and combinations thereof.

18. The device of claim 14, wherein the at least one tissue retaining fastener is bioabsorbable or dissolvable.

19. The device of claim 14, wherein the at least one tissue retaining fastener is made from a biocompatible material selected from the group consisting of stainless steel, titanium, NiTi, and structural polymers.

20. The device of claim 14, wherein the at least one tissue retaining fastener comprises a tack having a cross member and at least two tissue penetrating projections.

21. The device of claim 20, Wherein the tissue penetrating, projections are configured to penetrate fewer than all of the layers of the tissue being engaged, approximated and fastened.

22. A device of claim 20, wherein the tissue penetrating projections are configured to penetrate at least the external serosal layer of the gastrointestinal tract while penetrating fewer than all the layers of the gastrointestinal wall.

23. The device of claim 20, wherein the tissue penetrating projections further comprise at least one tissue retention feature.

24. The device of claim 23, wherein the tissue retention feature is selected from the group consisting of: points, barbs, hooks, tines, and sharpened edges.

25. The device of claim 23, wherein the tissue retention feature is adapted to reconfigure in a self-actuating manner from a collapsed condition to an extended condition.

26. A device of claim 23, wherein the tissue retention feature is positioned at a location along the tissue penetrating projection that is proximal to its distal end.

27. The device of claim 23, wherein the tissue retention feature is partially or substantially elastically deformable.

28. The device of claim 20, wherein the tissue retaining fastener further comprises at least one feature configured to promote tissue ingrowth through and around the fastener after surgery.

29. The device of claim 20, wherein the distal ends of the tissue penetrating projections are at least partially blunted.

30. The device of claim 14, wherein the tissue retaining fastener comprises a connecting member and at least two tissue penetrating members, wherein at least a portion of each tissue penetrating member comprises a flexible material.

31. The device of claim 14, wherein the tissue retaining fastener comprises a superelastic material.

32. The device of claim 14, wherein the tissue retaining fastener comprises a U-shaped fastener having a cross member and elastically deformable arms extending from the cross member.

33. A device of claim 14, wherein the tissue retaining fastener comprises a connecting member and at least two tissue penetrating members, wherein each tissue penetrating member is flexible and is adapted to reconfigure in a self-actuating manner from a first pre-deployed configuration to a different second deployed configuration.

34. The device of claim 33, wherein a tissue penetrating member elastically deforms in a proximal direction during the reconfiguration between the first pre-deployed and the different second deployed configuration.

35. The device of claim 33, wherein, in the deployed configuration, the tissue penetrating member forms one or more closed-loop shapes.

36. The device of claim 33, wherein the width of the fastener in the deployed configuration exceeds the width of the fastener in the pre-deployed configuration.

37. The device of claim 33, wherein the width of the fastener in the deployed configuration is larger than the diameter of the device.

38. The device of claim 14, additionally comprising a spring-loaded trigger mechanism operable to initiate deployment of tissue retaining fasteners.

* * * * *

UNITED STATES PATENT AND TRADEMARK OFFICE
CERTIFICATE OF CORRECTION

| | | |
|---|---|---|
| PATENT NO. | : 8,979,872 B2 | Page 1 of 1 |
| APPLICATION NO. | : 12/184173 | |
| DATED | : March 17, 2015 | |
| INVENTOR(S) | : Peter S. Harris and Barry Hal Rabin | |

It is certified that error appears in the above-identified patent and that said Letters Patent is hereby corrected as shown below:

In the claims:

Column 51, line 23, replace "comprising as" with --comprising a--

Signed and Sealed this
Eighth Day of September, 2015

Michelle K. Lee
*Director of the United States Patent and Trademark Office*